US008022193B2

(12) United States Patent
Seth et al.

(10) Patent No.: US 8,022,193 B2
(45) Date of Patent: *Sep. 20, 2011

(54) 6-MODIFIED BICYCLIC NUCLEIC ACID ANALOGS

(75) Inventors: Punit P. Seth, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/774,527

(22) Filed: May 5, 2010

(65) Prior Publication Data

US 2010/0216979 A1 Aug. 26, 2010

Related U.S. Application Data

(63) Continuation of application No. 12/129,154, filed on May 29, 2008, now Pat. No. 7,741,457, which is a continuation of application No. 11/627,964, filed on Jan. 27, 2007, now Pat. No. 7,399,845.

(60) Provisional application No. 60/762,722, filed on Jan. 27, 2006, provisional application No. 60/805,660, filed on Jun. 23, 2006.

(51) Int. Cl.
*C07H 19/00* (2006.01)
*C07H 21/00* (2006.01)

(52) U.S. Cl. ............... 536/22.1; 536/23.1; 514/43

(58) Field of Classification Search ............ None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederspn et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |

(Continued)

FOREIGN PATENT DOCUMENTS

WO     WO 94/02499     2/1994

(Continued)

OTHER PUBLICATIONS

Altschul et al., "Basic Local Alignment Search Tool" J. Mol. Biol. (1990) 215:403-410.
Babu et al., "" J. Chem. Soc. (2002) Perkin Trans. 1, pp. 2509-2519.
Barany et al., "A New Amino Protecting Group Removable by Reduction. Chemistry of the Dithiasuccinoyl (Dts) Function" J. Am. Chem. Soc. (1977) 99:7363-7365.
Barany et al., "Kinetics and Mechanisms of the Thiolytic Removal of the Dithiasuccinoyl (Dts) Amino Protecting Group" J. Am. Chem. Soc. (1980) 102:3084-3095.
Bass, "Double-stranded RNA as a template for gene silencing" Cell (2000) 101:235-238.

(Continued)

*Primary Examiner* — Patrick Lewis
(74) *Attorney, Agent, or Firm* — Jones Day

(57) ABSTRACT

The present invention provides 6-modified bicyclic nucleoside analogs and oligomeric compounds comprising these nucleoside analogs. In preferred embodiments the nucleoside analogs have either (R) or (S)-chirality at the 6-position. These bicyclicnucleoside analogs are useful for enhancing properties of oligomeric compounds including nuclease resistance.

19 Claims, No Drawings

U.S. PATENT DOCUMENTS

| | | | |
|---|---|---|---|
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,607,922 | A | 3/1997 | De Clercq et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,792,608 | A | 8/1998 | Swaminathan et al. |
| 5,792,747 | A | 8/1998 | Schally et al. |
| 5,830,653 | A | 11/1998 | Froehler et al. |
| 6,005,096 | A | 12/1999 | Matteucci et al. |
| 6,043,060 | A | 3/2000 | Imanishi |
| 6,268,490 | B1 | 7/2001 | Imanishi et al. |
| 6,426,220 | B1 | 7/2002 | Bennett et al. |
| 6,436,640 | B1 | 8/2002 | Simmons et al. |
| 6,600,032 | B1 | 7/2003 | Manoharan et al. |
| 6,770,748 | B2 | 8/2004 | Imanishi et al. |
| 6,794,499 | B2 | 9/2004 | Wengel et al. |
| 7,053,207 | B2 | 5/2006 | Wengel |
| 7,399,845 | B2 | 7/2008 | Seth et al. |
| 2003/0082807 | A1 | 5/2003 | Wengel |
| 2003/0087230 | A1 | 5/2003 | Wengel |
| 2003/0105309 | A1 | 6/2003 | Imanishi et al. |
| 2003/0207841 | A1 | 11/2003 | Kaneko et al. |
| 2003/0224377 | A1 | 12/2003 | Wengel et al. |
| 2004/0014959 | A1 | 1/2004 | Sorensen et al. |
| 2004/0143114 | A1 | 7/2004 | Imanishi et al. |
| 2004/0192918 | A1 | 9/2004 | Imanishi et al. |
| 2004/0219565 | A1 | 11/2004 | Kauppinen et al. |

FOREIGN PATENT DOCUMENTS

| | | |
|---|---|---|
| WO | WO 94/17093 | 8/1994 |
| WO | WO 94/22890 | 10/1994 |
| WO | WO 98/39352 | 9/1998 |
| WO | WO 99/14226 | 3/1999 |
| WO | WO 02/36743 | 5/2002 |
| WO | WO 05/12371 | 12/2005 |
| WO | WO 05/12372 | 12/2005 |
| WO | WO 2007090071 | 8/2007 |

OTHER PUBLICATIONS

Beaucage et al., "The Functionalization of Oligonucleotides via Phosphoramidite Derivatives" Tetrahedron (1993) 49:1925-1963.

Beaucage et al., "The Synthesis of Specific Ribonucleotides and Unrelated Phosphorylated Biomolecules by the Phosphoramidite Method" Tetrahedron (1993) 49:10441-10488.

Beaucage et al., "Advances in the Synthesis of Oligonucleotides by the Phosphoramidite Approach" Tetrahedron (1992) 48:2223-2311.

Beigelman et al., "Synthesis of 5'-C-Methyl-D-Allo- & L-Talo-Ribonucleoside 3'-O-Phosphoramidies and Their Incorporation into Hammerhead Ribozymes" Nucleoside Nucleotides (1995) 14:901-905.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Englisch et al., "Chemically Modified Oligonucleotides as Probes and Inhibitors" Agnew Chem. Int. Ed. Engl. (1991) 30:613-629.

Fire et al., "Potent and Specific Genetic Interference by Double-Stranded RNA in Caenorhabditis Elegans" Nature (1998) 391:806-811.

Fuchs et al., "Identification of Differentially Expressed Genes by Mutually Subtracted RNA Fingerprinting" Anal. Biochem. (2000) 286:91-98.

Gait, "Oligoribonucleotides" Antisense Research and Applications (1993), CRC Press, Boca Raton, pp. 289-301.

Gait et al., "Application of chemically syntesized RNA" RNA: Protein Interactions (1998) 1-36.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999)35:1895-1904.

Hari et al., "Synthesis and properties of oligonucleotides containing novel 2',4'-BNA analogues (2',4'- BNAcoc)" *Nucleic Acids Research Supplement No. 2* (2002) 147-148.

Hornbeck et al., "Enzyme-Linked Immunosorbet Assays (ELISA)" Curr. Protocols Mol. Biol. (1991) John Wiley & Sons 11.2.1-11.2.22.

International Search Report for PCT/US2007/061183 dated Jan. 27, 2007.

International Search Report for PCT/US2007/068690 dated Nov. 30, 2007.

Jungblut et al., "Proteomics in human disease: Cancer, heart and infections diseases" Electrophoresis (1999) 20:2100-2110.

Jurecic et al., "Long-distance DD-PCR and cDNA microarrays" Curr. Opin. Microbiol. (2000) 3:316-321.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Lane et al., "NMR assignments and solution conformation of the DNA:RNA hybrid duplex d(GTGAACTT)r(AAGUUCAC)" Eur. J. Biochem. (1993) 215:297-306.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotech. (2000) 80:143-157.

Madden et al., "Serial analysis of gene expression: from gene discovery to target identification" DDT (2000) 5:415-425.

Mikhailov et al., "Substrate Properties of C'-Methylnucleoside and C'-Methyl-2'-Deoxynucleoside 5'- Triphosphates in RNA and DNA Synthesis Reactions Catalysed by RNA and DNA Polymerase" Nucleosides Nucleotides (1991) 10:339-343.

Montgomery et al., "RNA as a target of double-stranded RNA-mediated genetic interference in *Caenorhabditis elegans*" Proc Natl. Acad. Sci. (1998) 95:15502-7.

Nishikura, "A Short Primer on RNAi: RNA-Directed RNA Polymerase Acts as a Key Catalyst" Cell (2001) 107:415-418.

Prashar et al., "READS: A Method for Display of 3'-End Fragment of Restriction Enzyme-Digested cDNAs for Analysis of Differential Gene Expression" Methods Enzymol. (1999) 303:258-272.

Saha et al., "5'-Me-DNA—A New Oligonucleotide Analog: Synthesis and Biochemical Properties" J. Org. Chem. (1995) 60:788-789.

Sanghvi, Chapter 15, Antisense Research and Applications, pp. 289-302, Crooke and Lebleu ed., CRC Press (1993).

Scaringe, "RNA Oligonucleotide Synthesis via 5'-Sily1-2'-Orthoester Chemistry" Methods (2001) 23:206-217.

Singh et al., "Synthesis of 2'-amino-LNA: A novel conformationally restricted high-affinity oligonucleotide analogue with a handle" J. Org. Chem. (1998) 63: 10035-10039.

Singh et al., "LNA (locked nucleic acids): synthesis and high-affinity nucleic acid recognition" Chem. Commun. (1998) 455-456.

Sonveaux, "Protecting Groups in Oligonucleotide Synthesis" Protocols for Oligonucleotide Conjugates (1994) 26:1-71.

Sutcliffe et al., "TOGA: An automated parsing technology for analyzing expression of nearly all genes" PNAS (2000) 97:1976-1981.

Swayze et al., "Antisense oligonucleotides containing locked nucleic acid improve potency but cause significant hepatotoxicity in animals" Nucleic Acids Res. (2007)35:687-700.

Tabara et al., "RNAi in *C. elegans*: Soaking in the Genome Sequence" Science (1998) 282:430-431.

Tijsterman et al., "RNA hellcase MUT-14-dependent gene silencing triggered in *C. elegans* by short antisense RNAs" Science (2002) 295:694-7.

Timmons et al., "Specific Interference by Ingested dsRNA" Nature (1998)395:854.

Timmons et al., "Ingestion of bacterially expressed dsRNAs can produce specific and potent genetic interference in *Caenorhabditis elegans*" Gene (2001) 263:103-112.

To "Identification of Differential Gene Expression by High Throughput Analysis" Comb. Chem. High Throughput Screen (2000) 3:235-241.

Tuschl et al., "Targeted mRNA degradation by double-stranded RNA in vitro" Genes Dev. (1999) 13:3191-7.

Wahlestedt et al., "Potent and nontoxic antisense oligonucleotide containing locked nucleic acids" Proc. Natl. Acad. Sci. USA(2000) 97: 5633-5638.

Wang et al., "5'-C-Branched Thymidines: Synthesis, Sterochemistry, and Incorporation into Oligodeoxynucleotides" Tetrahedron Letters (1996) 37:2739-2742.

Wang et al., "Biophysical and Biochemical Properties of Oligodeoxynucleotides Containing 4'-C- and 5'-C-Substituted Thymidines" Bioorg. Med. Chem. Lett. (1999) 9:885-890.

Youssefyeh et al., "4'-Substituted Nucleosides. 4. Synthesis of some 4'-Hydroxymethyl Nucleosides" J. Org. Chem. (1979) 44:1301-1309.

Zhang et al., "PowerBLAST: A New Network BLAST Application for Interactive or Automated Sequence Analysis and Annotation" Genome Res. (1997) 7:649-656.

6-MODIFIED BICYCLIC NUCLEIC ACID ANALOGS

CROSS-REFERENCE TO RELATED APPLICATIONS

This application is a continuation of U.S. patent application Ser. No. 12/129,154, filed May 29, 2008, which is a continuation of U.S. patent application Ser. No. 11/627,964, filed Jan. 27, 2007; which claims benefit under 35 USC 119(e) to U.S. Provisional Application No. 60/762,722, filed Jan. 27, 2006 and U.S. Provisional Application No. 60/805,660, filed Jun. 23, 2006, the entirety of each of these disclosures are incorporated herein by reference.

SEQUENCE LISTING

The present application is being filed along with a Sequence Listing in electronic format. The Sequence Listing is provided as a file entitled CHEM0027USC2SEQ.txt, created on May 5, 2010 which is 8 Kb in size. The information in the electronic format of the sequence listing is incorporated herein by reference in its entirety.

FIELD OF THE INVENTION

The present invention provides 6-modified bicyclic nucleosides and oligomeric compounds and compositions prepared therefrom. More particularly, the present invention provides nucleosides having a 2'-O—C(H)(R)-4' bridge and oligomers and compositions prepared therefrom. In a preferred embodiment, R is in a particular configuration providing either the (R) or (S) isomer. In some embodiments, the oligomeric compounds and compositions of the present invention hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

Many LNA's are toxic. See, e.g., Swayze, E. E.; Siwkowski, A. M.; Wancewicz, E. V.; Migawa, M. T.; Wyrzykiewicz, T. K.; Hung, G.; Monia, B. P.; Bennett, C. F., Antisense oligonucleotides containing locked nucleic acid improve potency but cause significant hepatotoxicity in animals. Nucl. Acids Res., doi: 10.1093/nar/gkl1071 (December 2006, advanced online publication).

Consequently, there remains a long-felt need for agents that specifically regulate gene expression via antisense mechanisms. Disclosed herein are 6-substituted BNA's and antisense compounds prepared therefrom useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

The present invention provides a bicyclic nucleoside having the formula:

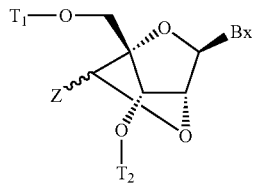

wherein:
Bx is a heterocyclic base moiety;
$T_1$ is H or a hydroxylprotecting group;
$T_2$ is H, a hydroxylprotecting group or a reactive phosphorus group;
Z is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, or substituted amide.

In one embodiment, each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In one embodiment, each of the substituted groups, is, independently, mono or poly substituted with substituent groups independently selected from halogen, oxo, hydroxyl, $OJ_1$, $NJ_1J_2$, $SJ_1$, $N_3$, $OC(=X)J_1$, and $NJ_3C(=X)NJ_1J_2$, wherein each $J_1$, $J_2$ and $J_3$ is, independently, H, $C_1$-$C_6$ alkyl, or substituted $C_1$-$C_6$ alkyl and X is O or $NJ_1$.

In one embodiment, Z is $C_1$-$C_6$ alkyl or substituted $C_1$-$C_6$ alkyl. In another embodiment, Z is $C_1$-$C_6$ alkyl. In another embodiment, Z is methyl ($CH_3$—). In another embodiment, Z is ethyl ($CH_3CH_2$—). In another embodiment, Z is substituted $C_1$-$C_6$ alkyl. In another embodiment, Z is substituted methyl. In another embodiment, Z is substituted ethyl.

In one embodiment, the substituent group is $C_1$-$C_6$ alkoxy (e.g., Z is $C_1$-$C_6$ alkyl substituted with one or more $C_1$-$C_6$ alkoxy). In another embodiment, the $C_1$-$C_6$ alkoxy substituent group is $CH_3O$— (e.g., Z is $CH_3OCH_2$—). In another embodiment, the $C_1$-$C_6$ alkoxy substituent group can be further substituted such as $N(J_1J_2)CH_2O$— (e.g., Z is $N(J_1J_2)CH_2OCH_2$—).

In another embodiment, the substituent group is halogen (e.g., Z is $C_1$-$C_6$ alkyl substituted with one or more halogen). In another embodiment, the halogen substituent group is fluoro (e.g., Z is $CH_2FCH_2$—, $CHF_2CH_2$— or $CF_3CH_2$—). In another embodiment, the substituent group is hydroxyl (e.g., Z is $C_1$-$C_6$ alkyl substituted with one or more hydroxyl). In another embodiment, Z is $HOCH_2$—. In another embodiment, Z is $CH_3$—, $CH_3CH_2$—, —$CH_2OCH_3$, —$CH_2F$ or $HOCH_2$—.

In one embodiment, the Z group is $C_1$-$C_6$ alkyl substituted with one or more $X^x$, wherein each $X^x$ is independently $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, the Z group is $C_1$-$C_6$ alkyl substituted with one or more $X^x$, wherein each $X^x$ is independently halo (e.g., fluoro), hydroxyl, alkoxy (e.g., $CH_3O$—), substituted alkoxy or azido.

In one embodiment, the Z group is —$CH_2X^x$, wherein $X^x$ is $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, the Z group is —$CH_2X^x$, wherein r is halo (e.g., fluoro), hydroxyl, alkoxy (e.g., $CH_3O$—) or azido.

In one embodiment, the Z group is in the (R)-configuration:

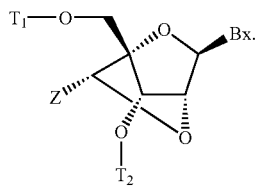

In another embodiment, the Z group is in the (S)-configuration:

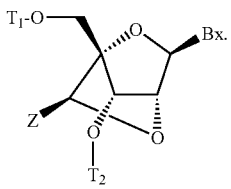

In one embodiment, each $T_1$ and $T_2$ is a hydroxyl protecting group. A preferred list of hydroxyl protecting groups includes benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In one embodiment $T_1$ is a hydroxyl protecting group selected from acetyl, benzyl, t-butyldimethylsilyl, t-butyldiphenylsilyl and dimethoxytrityl wherein a more preferred hydroxyl protecting group is $T_1$ is 4,4'-dimethoxytrityl.

In one embodiment, $T_2$ is a reactive phosphorus group wherein preferred reactive phosphorus groups include diisopropylcyanoethoxy phosphoramidite and H-phosphonate. In one preferred embodiment $T_1$ is 4,4'-dimethoxytrityl and $T_2$ is diisopropylcyanoethoxy phosphoramidite.

The present invention also provides oligomeric compounds having at least one monomer of the formula:

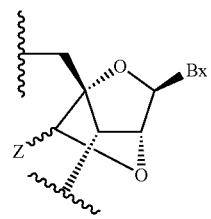

or of the formula:

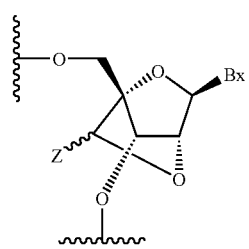

or of the formula:

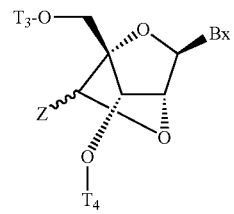

wherein
  Bx is a heterocyclic base moiety;
  $T_3$ is H, a hydroxyl protecting group, a linked conjugate group or an internucleoside linking group attached to a nucleoside, a nucleotide, an oligonucleoside, an oligonucleotide, a monomeric subunit or an oligomeric compound;
  $T_4$ is H, a hydroxyl protecting group, a linked conjugate group or an internucleoside linking group attached to a nucleoside, a nucleotide, an oligonucleoside, an oligonucleotide, a monomeric subunit or an oligomeric compound;
  wherein at least one of $T_3$ and $T_4$ is an internucleoside linking group attached to a nucleoside, a nucleotide, an oligonucleoside, an oligonucleotide, a monomeric subunit or an oligomeric compound; and
  Z is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, or substituted amide.

In one embodiment, each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In one embodiment, each of the substituted groups, is, independently, mono or poly substituted with substituent groups independently selected from halogen, oxo, hydroxyl, $OJ_1$, $NJ_1J_2$, $SJ_1$, $N_3$, $OC(=X)J_1$, and $NJ_3C(=X)NJ_1J_2$, wherein each $J_1$, $J_2$ and $J_3$ is, independently, H or $C_1$-$C_6$ alkyl, and X is O or $NJ_1$.

In one embodiment, at least one Z is $C_1$-$C_6$ alkyl or substituted $C_1$-$C_6$ alkyl. In another embodiment, each Z is, independently, $C_1$-$C_6$ alkyl or substituted $C_1$-$C_6$ alkyl. In another embodiment, at least one Z is $C_1$-$C_6$ alkyl. In another embodiment, each Z is, independently, $C_1$-$C_6$ alkyl. In another embodiment, at least one Z is methyl. In another embodiment, each Z is methyl. In another embodiment, at least one Z is ethyl. In another embodiment, each Z is ethyl.

In another embodiment, at least one Z is substituted $C_1$-$C_6$ alkyl. In another embodiment, each Z is, independently, substituted $C_1$-$C_6$ alkyl. In another embodiment, at least one Z is substituted methyl. In another embodiment, each Z is substituted methyl. In another embodiment, at least one Z is substituted ethyl. In another embodiment, each Z is substituted ethyl.

In one embodiment, at least one substituent group is $C_1$-$C_6$ alkoxy (e.g., at least one Z is $C_1$-$C_6$ alkyl substituted with one or more $C_1$-$C_6$ alkoxy). In another embodiment, each substituent group is, independently, $C_1$-$C_6$ alkoxy (e.g., each Z is, independently, $C_1$-$C_6$ alkyl substituted with one or more $C_1$-$C_6$ alkoxy).

In one embodiment, at least one $C_1$-$C_6$ alkoxy substituent group is $CH_3O$— (e.g., at least one Z is $CH_3OCH_2$—). In another embodiment, each $C_1$-$C_6$ alkoxy substituent group is $CH_3O$— (e.g., each Z is $CH_3OCH_2$—).

In one embodiment, at least one substituent group is halogen (e.g., at least one Z is $C_1$-$C_6$ alkyl substituted with one or more halogen). In another embodiment, each substituent group is, independently, halogen (e.g., each Z is, independently, $C_1$-$C_6$ alkyl substituted with one or more halogen). In another embodiment, at least one halogen substituent group is fluoro (e.g., at least one Z is $CH_2FCH_2$—, $CHF_2CH_2$— or $CF_3CH_2$—). In another embodiment, each halo substituent group is fluoro (e.g., each Z is, independently, $CH_2FCH_2$—, $CHF_2CH_2$— or $CF_3CH_2$—).

In one embodiment, at least one substituent group is hydroxyl (e.g., at least one Z is $C_1$-$C_6$ alkyl substituted with one or more hydroxyl). In another embodiment, each substituent group is, independently, hydroxyl (e.g., each Z is, independently, $C_1$-$C_6$ alkyl substituted with one or more hydroxyl). In another embodiment, at least one Z is $HOCH_2$—. In another embodiment, each Z is $HOCH_2$—.

In one embodiment, at least one Z is $CH_3$—, $CH_3CH_2$—, $CH_2OCH_3$—, $CH_2F$— or $HOCH_2$—. In another embodiment, each Z is, independently, $CH_3$—, $CH_3CH_2$—, $CH_2OCH_3$—, $CH_2F$— or $HOCH_2$—.

In one embodiment, at least one Z group is $C_1$-$C_6$ alkyl substituted with one or more $X^x$, wherein each $X^x$ is, independently, $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, at least one Z group is $C_1$-$C_6$ alkyl substituted with one or more $X^x$, wherein each $X^x$ is, independently, halo (e.g., fluoro), hydroxyl, alkoxy (e.g., $CH_3O$—) or azido.

In one embodiment, each Z group is, independently, $C_1$-$C_6$ alkyl substituted with one or more $X^x$, wherein each $X^x$ is independently $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, each Z group is, independently, $C_1$-$C_6$ alkyl substituted with one or more $X^x$, wherein each $X^x$ is independently halo (e.g., fluoro), hydroxyl, alkoxy (e.g., $CH_3O$—) or azido.

In one embodiment, at least one Z group is —$CH_2X^x$, wherein $X^x$ is $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, at least one Z group is —$CH_2X^x$, wherein $X^x$ is halo (e.g., fluoro), hydroxyl, alkoxy (e.g., $CH_3O$—) or azido.

In one embodiment, each Z group is, independently, —$CH_2X^x$, wherein each $X^x$ is, independently, $OJ_1$, $NJ_1J_2$, $SJ_1$, $N_3$, $OC(=X)J_1$, $OC(=X)NJ_1J_2$, $NJ_3C(=X)NJ_1J_2$ or CN; wherein each $J_1$, $J_2$ and $J_3$ is, independently, H or $C_1$-$C_6$ alkyl, and X is O, S or $NJ_1$. In another embodiment, each Z group is, independently, —$CH_2X^x$, wherein each $X^x$ is, independently, halo (e.g., fluoro), hydroxyl, alkoxy (e.g., $CH_3O$—) or azido.

In one embodiment, at least one Z is $CH_3$—. In another embodiment, each Z is, $CH_3$—.

In one embodiment, the Z group of at least one monomer is in the (R)-configuration represented by the formula:

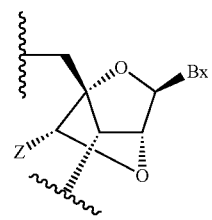

or the formula:

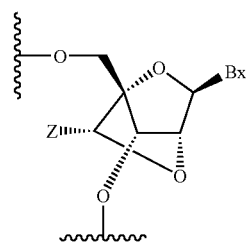

or the formula:

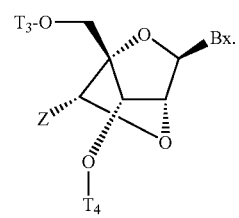

In another embodiment, the Z group of each monomer of the formula is in the (R)-configuration.

In one embodiment, the Z group of at least one monomer is in the (S)-configuration represented by the formula:

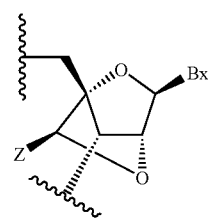

or the formula:

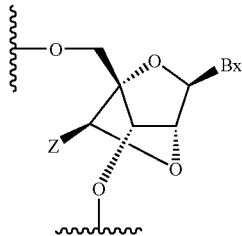

or the formula:

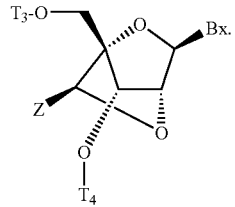

In another embodiment, the Z group of each monomer of the formula is in the (S)-configuration.

In one embodiment, $T_3$ is H or a hydroxyl protecting group. In another embodiment $T_4$ is H or a hydroxyl protecting group. In a further embodiment $T_3$ is an internucleoside linking group attached to a nucleoside, a nucleotide or a monomeric subunit. In another embodiment $T_4$ is an internucleoside linking group attached to a nucleoside, a nucleotide or a monomeric subunit. In another embodiment $T_3$ is an internucleoside linking group attached to an oligonucleoside or an oligonucleotide. In a further embodiment $T_4$ is an internucleoside linking group attached to an oligonucleoside or an oligonucleotide. In one embodiment $T_3$ is an internucleoside linking group attached to an oligomeric compound. In a further embodiment $T_4$ is an internucleoside linking group attached to an oligomeric compound. In an even further embodiment at least one of $T_3$ and $T_4$ comprises an internucleoside linking group selected from phosphodiester or phosphorothioate.

In one embodiment, oligomeric compounds have at least one region of at least two contiguous monomers of the formula:

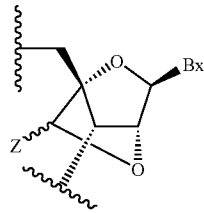

or of the formula:

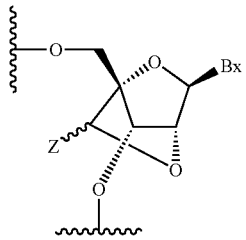

or of the formula:

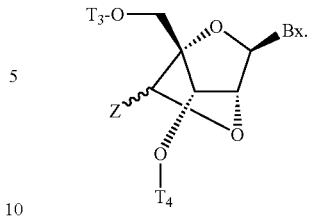

to

In another embodiment, the oligomeric compound comprises at least two regions of at least two contiguous monomers of the above formula. In a further embodiment the oligomeric compound comprises a gapped oligomeric compound. In another embodiment the oligomeric compound comprises at least one region of from about 8 to about 14 contiguous β-D-2'-deoxyribofuranosyl nucleosides. In a further embodiment the oligomeric compound comprises at least one region of from about 9 to about 12 contiguous β-D-2'-deoxyribofuranosyl nucleosides.

In one embodiment, the oligomeric compound comprises at least one region of from 2 to three contiguous monomers of the above formula, an optional second region of 1 or 2 contiguous monomers of the above formula and a third region of from 8 to 1413-D-2'-deoxyribofuranosyl nucleosides wherein the third region is located between the first and the second regions. In another embodiment the oligomeric compound comprises from 8 to 10 β-D-2'-deoxyribofuranosyl nucleosides.

In another embodiment of the present invention oligomeric compounds are provided having from about 8 to about 40 nucleosides and/or modified nucleosides or mimetics in length. In a further embodiment oligomeric compound comprise from about 8 to about 20 nucleosides and/or modified nucleosides or mimetics in length. In an even further embodiment oligomeric compounds comprise from about 10 to about 16 nucleosides and/or modified nucleosides or mimetics in length. In another embodiment oligomeric compounds comprise from about 10 to about 14 nucleosides and/or modified nucleosides or mimetics in length.

Also provided are methods of inhibiting gene expression comprising contacting one or more cells, a tissue or an animal with an oligomeric compound of the invention.

DETAILED DESCRIPTION OF THE INVENTION

The present invention provides 6-modified bicyclic nucleosides, oligomeric compounds and compositions prepared therefrom, novel synthetic intermediates, and methods of preparing the nucleosides, oligomeric compounds, compositions, and novel synthetic intermediates. More particularly, the present invention provides nucleosides having a bridge between the 4' and 2'-positions of the ribose portion having the formula: 2'-O—C(H)(Z)-4' and oligomers and compositions prepared therefrom. In a preferred embodiment, Z is in a particular configuration providing either the (R) or (S) isomer. In some embodiments, the oligomeric compounds and compositions of the present invention are designed to hybridize to a portion of a target RNA. In another embodiment, the oligomeric compounds of the present invention can be used in the design of aptamers which are oligomeric compounds capable of binding to aberrant proteins in an in vivo setting.

Bicyclic nucleosides of the present invention are useful for enhancing desired properties of oligomeric compounds in which they are incorporated. The oligomers of the present invention may also be useful as primers and probes in diagnostic applications. In a preferred embodiment the 6-modified bicyclic nucleosides of the present invention have the structure shown below:

In one aspect the present invention provides bicyclic nucleosides having formula I:

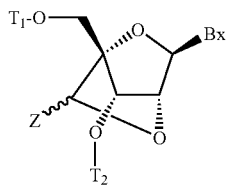

I wherein:
Bx is a heterocyclic base moiety;
$T_1$ is H or a hydroxyl protecting group;
$T_2$ is H, a hydroxyl protecting group or a reactive phosphorus group; and
Z is $C_1$-$C_6$ alkyl, $C_2$-$C_6$ alkenyl, $C_2$-$C_6$ alkynyl, $C_1$-$C_6$ alkylidenyl, $C_3$-$C_6$ alkenylidenyl, substituted $C_1$-$C_6$ alkyl, substituted $C_2$-$C_6$ alkenyl, substituted $C_2$-$C_6$ alkynyl, substituted $C_1$-$C_6$ alkylidenyl, substituted $C_3$-$C_6$ alkenylidenyl, acyl, substituted acyl, substituted amide, thiol, or substituted thio.

In one embodiment, each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In one aspect of the present invention bicyclic nucleosides are prepared having reactive groups orthogonally protected and further comprising a reactive phosphorus group. Such bicyclic nucleosides are useful as monomers for oligomer synthesis. One illustrative example of such a bicyclic nucleoside monomer has the formula:

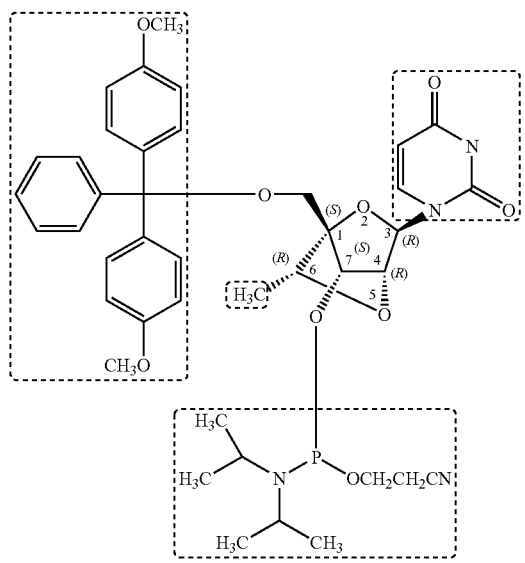

wherein the groups surrounded by broken lined boxes are variable. The group at the 6 position can also be prepared in the S configuration (note that the R and S designations may vary dependent on the groups at the variable positions). The bicyclic nucleoside monomer shown is generically referred to as a dimethoxytrityl phosphoramidite or more formally using IUPAC naming nomenclature as (1S,3R,4R,6R,7S)-7-[2-cyanoethoxy(diisopropylamino)phosphinoxy]-1-(4,4'-dimethoxytrityloxymethyl)-3-(uracil-1-yl)-6-methyl-2,5-dioxa-bicyclo[2.2.1]heptane.

The 6-modified bicyclic nucleosides of the present invention are useful for modifying otherwise unmodified oligomeric compounds at one or more positions. Such modified oligomeric compounds can be described as having a particular motif. Motifs amenable to the present invention include but are not limited to a gapped motif, a hemimer motif, a blockmer motif, a fully modified motif, a positionally modified motif and an alternating motif. In conjunction with these motifs a wide variety of linkages can also be used including but not limited to phosphodiester and phosphorothioate linkages used uniformly or in combinations. The positioning of 6-modified bicyclic nucleosides and the use of linkage strategies can be easily optimized for the best activity for a particular target. Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interupted with one or more heteroatoms that include nitrogen, oxygen, sulfur and phosphorus. Such aliphatic groups interupted by heteroatoms include without limitation polyalkoxys, such as polyalkylene glycols, polyamines, and polyimines. Aliphatic groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

The term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino (—N$R_{bb}R_{cc}$), imino(=N$R_{bb}$), amido (—C(O)N—$R_{bb}R_{cc}$ or —N($R_{bb}$)C(O)$R_{aa}$), azido (—$N_3$), nitro (—$NO_2$), cyano (—CN), carbamido (—OC(O)N$R_{bb}R_{cc}$ or —N($R_{bb}$)C(O)O$R_{aa}$), ureido (—N($R_{bb}$)C(O)N$R_{bb}R_{cc}$), thioureido (—N($R_{bb}$)C(S)N$R_{bb}R_{cc}$), guanidinyl (—N($R_{bb}$)C(=N$R_{bb}$)N$R_{bb}R_{cc}$), amidinyl (—C(=N$R_{bb}$)N$R_{bb}R_{cc}$ or —N($R_{bb}$)C(N$R_{bb}$)$R_{aa}$), thiol (—S$R_{bb}$), sulfinyl (—S(O)$R_{bb}$), sulfonyl (—S(O)$_2R_{bb}$), sulfonamidyl (—S(O)$_2$N$R_{bb}R_{cc}$ or —N($R_{bb}$)—S(O)$_2R_{bb}$) and conjugate groups. Wherein each $R_{aa}$, $R_{bb}$ and $R_{cc}$ is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl.

The term "oxo" refers to the group (=O).

The compounds (e.g., bicyclic nucleosides) described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

In one aspect of the present invention oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Linking groups or bifunctional linking moieties such as those known in the art are amenable to the present invention. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl(FPMP), 9-phenylxanthine-9-yl (Pixyl) and 9-(p-methoxyphenyl)xanthine-9-yl(MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In some preferred embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, 8-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. No. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

As used herein, the term "orthogonally protected" refers to functional groups which are protected with different classes of protecting groups, wherein each class of protecting group can be removed in any order and in the presence of all other classes (see, Barany, G. and Merrifield, R. B., J. Am. Chem. Soc., 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

The present invention provides compounds having reactive phosphorus groups useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites.

The intermediate phosphite compounds are subsequently oxidized to the $P^V$ state using known methods to yield, in preferred embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

Specific examples of oligomeric compounds useful in this invention include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938;

5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In the context of the present invention, the term "oligomeric compound" refers to a polymer having at least a region that is capable of hybridizing to a nucleic acid molecule. The term "oligomeric compound" includes oligonucleotides, oligonucleotide analogs and oligonucleosides as well as nucleotide mimetics and/or mixed polymers comprising nucleic acid and non-nucleic acid components. Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof." In general, a nucleobase is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Oligomeric compounds of the present invention may also contain one or more nucleosides having modified sugar moieties. The furanosyl sugar ring can be modified in a number of ways including substitution with a substituent group, bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-0(CH$_2$)$_2$—OCH$_3$ substituent group; 4'-thio modified sugars and bicyclic modified sugars.

As used herein the term "nucleoside mimetic" is intended to include those structures used to replace the sugar or the sugar and the base not the linkage at one or more positions of an oligomeric compound such as for example nucleoside mimetics having morpholino or bicyclo[3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

The oligomeric compounds in accordance with the present invention can comprise from about 8 to about 80 nucleosides and/or modified nucleosides or mimetics in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides and/or modified nucleosides or mimetics in length, or any range therewithin.

In another embodiment, the oligomeric compounds of the invention are 8 to 40 nucleosides and/or modified nucleosides or mimetics in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleosides and/or modified nucleosides or mimetics in length, or any range therewithin.

In another embodiment, the oligomeric compounds of the invention are 8 to 20 nucleosides and/or modified nucleosides or mimetics in length. One having ordinary skill in the art will appreciate that this embodies oligomeric compounds of 8, 9, 10, 11, 12, 13, 14, 15, 16, 17, 18, 19 or 20 nucleosides and/or modified nucleosides or mimetics in length, or any range therewithin.

In another embodiment, the oligomeric compounds of the invention are 10 to 16 nucleosides and/or modified nucleosides or mimetics in length. One having ordinary skill in the art will appreciate that this embodies oligomeric compounds of 10, 11, 12, 13, 14, 15 or 16 nucleosides and/or modified nucleosides or mimetics in length, or any range therewithin.

In another embodiment, the oligomeric compounds of the invention are 10 to 14 nucleosides and/or modified nucleosides or mimetics in length. One having ordinary skill in the art will appreciate that this embodies oligomeric compounds of 10, 11, 12, 13 or 14 nucleosides and/or modified nucleosides or mimetics in length, or any range therewithin.

Chimeric oligomeric compounds have differentially modified nucleosides at two or more positions and are generally defined as having a motif. Chimeric oligomeric compounds of the invention may be formed as composite structures of two or more oligonucleotides, oligonucleotide analogs, oligonucleosides and/or oligonucleotide mimetics as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Oligomerization of modified and unmodified nucleosides and mimetics thereof, in one aspect of the present invention, is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. No. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The oligomeric compounds of the present invention can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included in the present invention are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The suitable target segments of the present invention may also be combined with their respective complementary antisense oligomeric compounds of the present invention to form stabilized double-stranded (duplexed) oligonucleotides. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds of the present invention can also be applied in the areas of drug discovery and target validation. The present invention comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

The oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligomeric compounds of the present invention, either alone or in combination with other oligomeric compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904)

and mass spectrometry methods (To, Comb. Chem. High Throughput Screen, 2000, 3, 235-41).

The oligomeric compounds of the invention are useful for research and diagnostics, because these oligomeric compounds hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

While the present invention has been described with specificity in accordance with certain of its embodiments, the following examples serve only to illustrate the invention and are not intended to limit the same.

Example 1

Preparation of uridine 6-(R)-methyl BNA phosphoramidite, (1S,3R,4R,6R,7S)-7-[2-cyanoethoxy(diisopropylamino)phosphin oxy]-1-(4,4'-dimethoxytrityloxymethyl)-3-(uracil-1-yl)-6-methyl-2,5-dioxa-bicyclo[2.2.1]heptane (15)

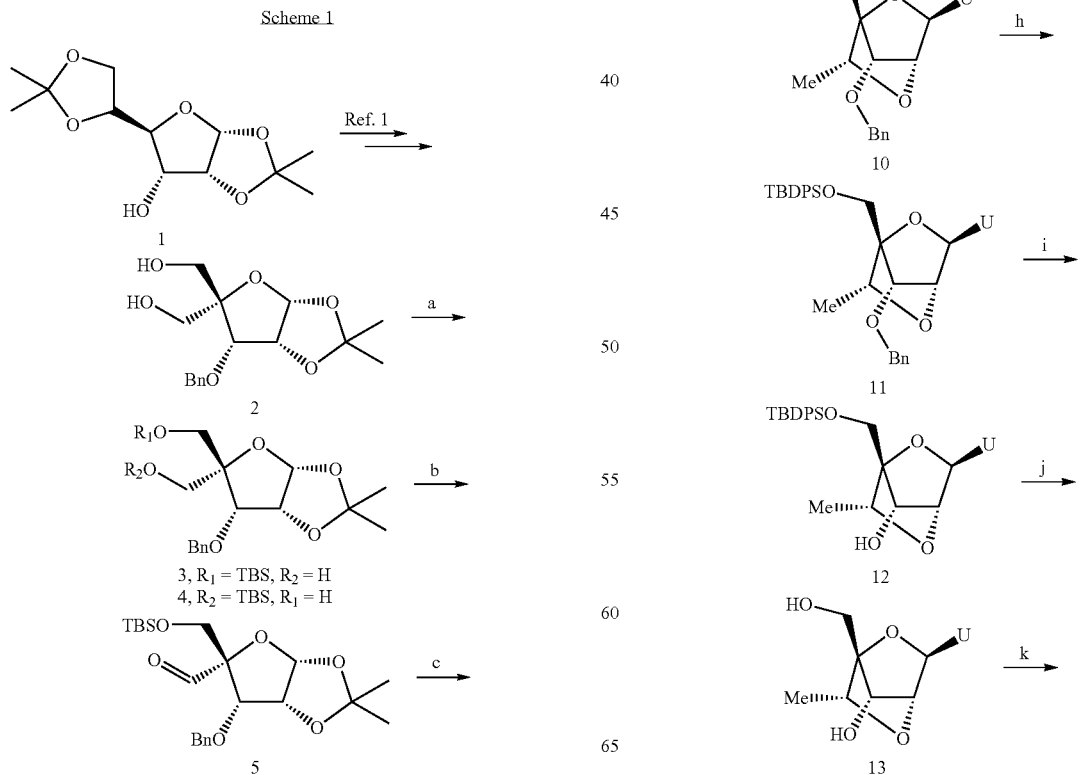

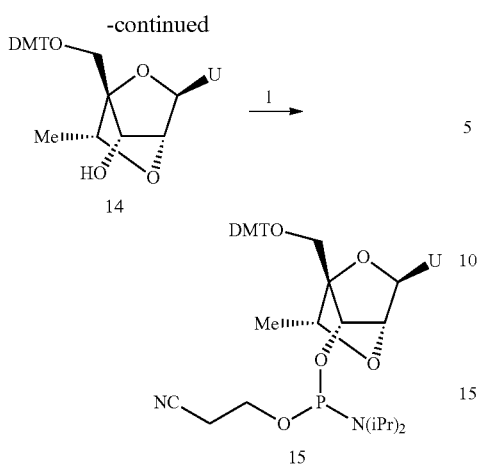

(a) TBSCl, Et₃N, DMAP, CH₂Cl₂, rt, 16 h, 59% for 3;
(b) Swern Oxidation
(c) MeMgBr, CeCl₃, THF, -78° C. 80% from 3;
(d) MsCl, Et₃N, DMAP, CH₂Cl₂, rt, 16 h, 91%;
(e) AcOH, Ac₂O, H₂SO₄, rt, 16 h, 88%;
(f) Uracil, BSA, TMSOTf, CH₃CN, reflux, 2 h;
(g) K₂CO₃, MeOH, rt, 16 h;
(h) TBDPSCl, Et₃N, DMAP, CH₂Cl₂, rt, 16 h, 79% from 8;
(i) BCl₃, CH₂Cl₂, -15° C., 60%;
(j) Et₃N·3HF, Et₃N, THF, rt, 16 h;
(k) DMTCl, Pyridine, rt, 16 h 89% from 12;
(l) CNCH₂CH₂OP(N-iPr₂)₂, Tetrazole, NMI, DMF.

A) 5-O-(tert-Butyldimethylsilyl)-3-O-benzyl-1,2-O-isopropylidene-4-C-hydroxymethyl-α-D-erythro-pentofuranose (3)

A solution of tert-Butyldimethylsilylchloride (6.24 g, 40.7 mmol) in dichloromethane (10 mL) was added over 10 min, via an addition funnel, to a cold (0° C.) solution of diol 2 (12 g, 38.8 mmol, prepared according to the procedure of Moffatt et al, *J. Org. Chem.* 1979, 44, 1301, Ref. 1), triethylamine (11.44 mL, 81.5 mmol) and 4-dimethylaminoethylpyridine (0.47 g, 3.9 mmol) in CH₂Cl₂ (184 mL). After the addition was complete, the reaction was gradually warmed to rt and stirred for an additional 16 h. The reaction was diluted with CH₂Cl₂ and sequentially washed with 5% aqueous HCl, saturated NaHCO₃, brine, dried (Na₂SO₄) and concentrated under vacuum. Purification by column chromatography (SiO₂, eluting with 10% to 30% EtOAc/hexanes) provided alcohol 3 (11.53 g, 59%) and alcohol 4 (3.93 g, 22%) as white solids.

B) Alcohol (6)

Dimethylsulfoxide (3.36 mL, 47.5 mmol) was added dropwise to a cold (-78° C.) solution of oxalyl chloride (2.08 mL, 23.7 mmol) in CH₂Cl₂ (130 mL). After stirring for 30 min, a solution of alcohol 3 (6.7 g, 15.8 mmol) in CH₂Cl₂ (20 mL) was added to the reaction. The stirring was continued for 45 min at -78° C. and triethylamine (10.0 mL, 71.2 mmol) was added to the reaction. The reaction was stirred at -78° C. for 15 min after which the ice bath was removed and the reaction was allowed to gradually warm over 45 min. The reaction was then poured into CH₂Cl₂ and the organic phase was sequentially washed with 5% aqueous HCl, saturated NaHCO₃, brine, dried (Na₂SO₄) and concentrated under vacuum to provide aldehyde 5, which was used without any further purification.

A suspension of cerium III chloride (5.84 g, 23.7 mmol) in THF (130 mL) was stirred at rt for 90 min. The reaction was cooled in an ice bath and methyl magnesium bromide (17.0 mL of a 1M solution in THF) was added over 5 min and the stirring continued for another 90 min. A solution of crude aldehyde 5 (from above) in THF (20 mL) was added to the reaction. After stirring for another 90 min, the reaction was quenched with sat NH₄Cl solution and poured into EtOAc. The organic layer was sequentially washed with 5% aqueous HCl, saturated NaHCO₃, brine, dried (Na₂SO₄) and concentrated under vacuum. Purification by column chromatography (SiO₂, eluting with 15% EtOAc/hexanes) provided alcohol 6 (5.52 g, 80% from 3).

C) Mesylate (7)

Methanesulfonyl chloride (0.55 mL, 7.0 mmol) was added to a cold (0° C.) solution of alcohol 6 (2.77 g, 6.4 mmol), triethylamine (1.1 mL, 7.7 mmol) and 4-dimethylaminopyridine (84 mg, 0.7 mmol) in CH₂Cl₂ (14 mL). After stirring at rt for 1 h, the reaction was poured into CHCl₃ and the organic layer was sequentially washed with 5% aqueous HCl, saturated NaHCO₃, brine, dried (Na₂SO₄) and concentrated under vacuum. Purification by column chromatography (SiO₂, eluting with 15% EtOAc/hexanes) provided mesylate 7 (2.97 g, 91%).

D) Triacetate (8)

Concentrated H₂SO₄ (3 drops) was added to a solution of mesylate 7 (2.97 g, 5.8 mmol) in glacial acetic acid (29 mL) and acetic anhydride (5.8 mL). After stirring at it for 1 h, the reaction was poured into EtOAc and the organic layer was washed with water, saturated NaHCO₃, brine, dried (Na₂SO₄) and concentrated under vacuum. Purification by column chromatography (SiO₂, eluting with 33% to 50% EtOAc/hexanes) provided triacetate 8 (2.48 g, 88%). ¹H NMR (CDCl₃, β anomer): δ 7.39-7.30 (m, 5H), 6.23 (s, 1H), 5.37 (d, 1H), 5.19 (q, 1H), 4.62 (d, 1H), 4.52 (d, 1H), 4.38 (s, 1H), 4.34 (d, 1H), 3.98 (d, 1H), 2.91 (s, 3H), 2.12 (s, 3H), 2.08 (s, 3H), 2.06 (s, 3H), 1.55 (d, 3H). LCMS: retention time 1.35 min; M+23 calcd. 511.1, found 511.0.

E) Nucleoside (11)

N,O-Bis(trimethylsilyl)acetamide (4.9 mL, 20.0 mmol) was added to a suspension of triacetate 8 (2.47 g, 5.0 mmol) and uracil (0.70 g, 6.3 mmol) in CH₃CN (15 mL). After heating at 40° C. for 15 min to get a clear solution, trimethylsilyl triflate (1.18 mL, 6.5 mmol) was added to the reaction. After refluxing for 2 h, the reaction was cooled to rt and poured into EtOAc. The organic layer was washed with saturated NaHCO₃, brine, dried (Na₂SO₄) and concentrated under vacuum to provide crude nucleoside 9, which was used without any purification.

K₂CO₃ (2.07 g, 15 mmol) was added to a solution of nucleoside 9 (from above) in MeOH (50 mL). After stirring for 16 h at it, the solvent was removed under vacuum and the residue was partitioned between 25% pyridine/EtOAc and brine. The organic phase was collected, dried (Na₂SO₄) and concentrated under vacuum to provide 10, which was used without any further purification. ¹H NMR (MeOD): δ 7.74 (d, 2H), 7.29-7.14 (m, 5H), 5.53 (d, 1H), 5.38 (s, 1H), 4.48 (s, 2H), 4.18 (s, 1H), 4.14 (sm, 1H), 3.92 (s, 1H), 3.66 (s, 2H), 1.08 (d, 3H). LCMS: retention time 2.40 min; M+H calcd. 360.1, found 361.0.

tert-Butyldiphenylsilyl chloride (1.73 mL, 6.7 mmol) was added to a cold (0° C.) solution of nucleoside 10 (from above), triethylamine (1.4 mL, 10.0 mmol) and 4-dimethylaminopyridine (80 mg, 0.7 mmol) in CH$_2$Cl$_2$ (9 mL). After stirring for 16 h at rt, the reaction was poured into EtOAc and the organic phase was sequentially washed with 5% aqueous HCl, saturated NaHCO$_3$, dried (Na$_2$SO$_4$) and concentrated under vacuum. Purification by column chromatography (SiO$_2$, eluting with 50% EtOAc/hexanes) provided nucleoside 11 (2.02 g, 79% from 8) as a white solid.

F) Nucleoside (12)

Boron trichloride (16.7 mL of a 1M solution in CH$_2$Cl$_2$) was carefully added to a cold (−15° C.) solution of nucleoside 11 (2.0 g, 3.3 mmol) in CH$_2$Cl$_2$ (40 mL). After stirring at −15° C. for 1 h, the reaction was cooled to −78° C. and carefully quenched by the addition of MeOH/CH$_2$Cl$_2$ (1:1, 10 mL). After stirring for an additional 10 min, the reaction was poured into CH$_2$Cl$_2$ and the organic phase was sequentially washed with 5% aqueous HCl, saturated NaHCO$_3$, brine, dried (Na$_2$SO$_4$) and concentrated under vacuum. Purification by column chromatography (SiO$_2$, eluting with 50% to 80% EtOAc/hexanes) provided nucleoside 12 as a white solid (1.02 g, 60%).

G) Nucleoside (13)

Triethylamine trihydrofluoride (2.98 mL, 18.3 mmol) was added to a solution of nucleoside 12 (1.86 g, 3.7 mmol) and triethylamine (1.03 mL, 7.3 mmol) in THF (36 mL), in a polypropylene tube. After stirring at rt for 16 h, the reaction was concentrated under vacuum and the residue dissolved in EtOAc. The organic layer was sequentially washed with water, saturated NaHCO$_3$, brine, dried (Na$_2$SO$_4$) and concentrated under vacuum. Purification by column chromatography (SiO$_2$, 15% MeOH/CHCl$_3$) provided nucleoside 13 (1.31 g, product contaminated with triethylamine) as a white solid.

H) Nucleoside (14)

4,4'-Dimethoxytrityl chloride (DMTCl) (1.23 g, 3.7 mmol) was added to a solution of nucleoside 13 (from above) in pyridine (18 mL). After stirring for 16 h at rt, additional DMTCl (0.12 g) was added to the reaction and the stirring was continued for another 8 h. The reaction was then poured into EtOAc and the organic layer was sequentially extracted with brine, dried (Na$_2$SO$_4$) and concentrated. Purification by column chromatography (SiO$_2$, eluting with 15% acetone/CHCl$_3$) provided nucleoside 14 (1.85 g, 89%) as a white foam. $^1$H NMR (CDCl$_3$): δ 8.03 (d, 1H), 7.44-2.28 (m, 14H), 6.86 (d, 4H), 5.63 (d, 1H), 5.60 (s, 1H), 4.32 (m, 1H), 4.13 (s, 1H), 3.81 (s, 6H), 3.49 (d, 1H), 3.37 (d, 1H), 1.18 (d, 3H).

I) Preparation of the phosphoramidite, (1S,3R,4R,6R,7S)-7-[2-cyanoethoxy-(diisopropylamino)phosphin oxy]-1-(4,4'-dimethoxytrityloxymethyl)-3-(uracil-1-yl)-6-methyl-2,5-dioxa-bicyclo[2.2.1]heptane (15)

2-Cyanoethyl tetraisopropylphorodiamidite (0.69 mL, 2.2 mmol) was added to a solution of nucleoside 14 (0.83 g, 1.4 mmol), tetrazole (80 mg, 1.2 mmol) and N-methylimidazole (29 μL, 0.36 mmol) in DMF (7.2 mL). After stirring at rt for 8 h, the reaction was poured into EtOAc and the organic layer was washed with 90% brine, brine, dried (Na$_2$SO$_4$) and concentrated. The residue was dissolved in minimum amount of EtOAc and this solution was added to hexanes. The resulting precipitate was collected and further purified by column chromatography (SiO$_2$, eluting with 66% to 75% EtOAc/hexanes) to provide phosphoramidite 15 as a white solid (1.04 g, 94%). $^{31}$P NMR (CDCl$_3$) δ: 149.21, 149.79.

Example 2

Preparation of uridine N-Bz-cytosine-6-(R)-methyl BNA phosphoramidite, (1S,3R,4R,6R,7S)-7-[2-cyanoethoxy(diisopropylamino)phosphin oxy]-1-(4,4'-dimethoxytrityloxymethyl)-3-(4-N-benzoylcytosin-1-yl)-6-methyl-2,5-dioxa-bicyclo[2.2.1]heptane (21)

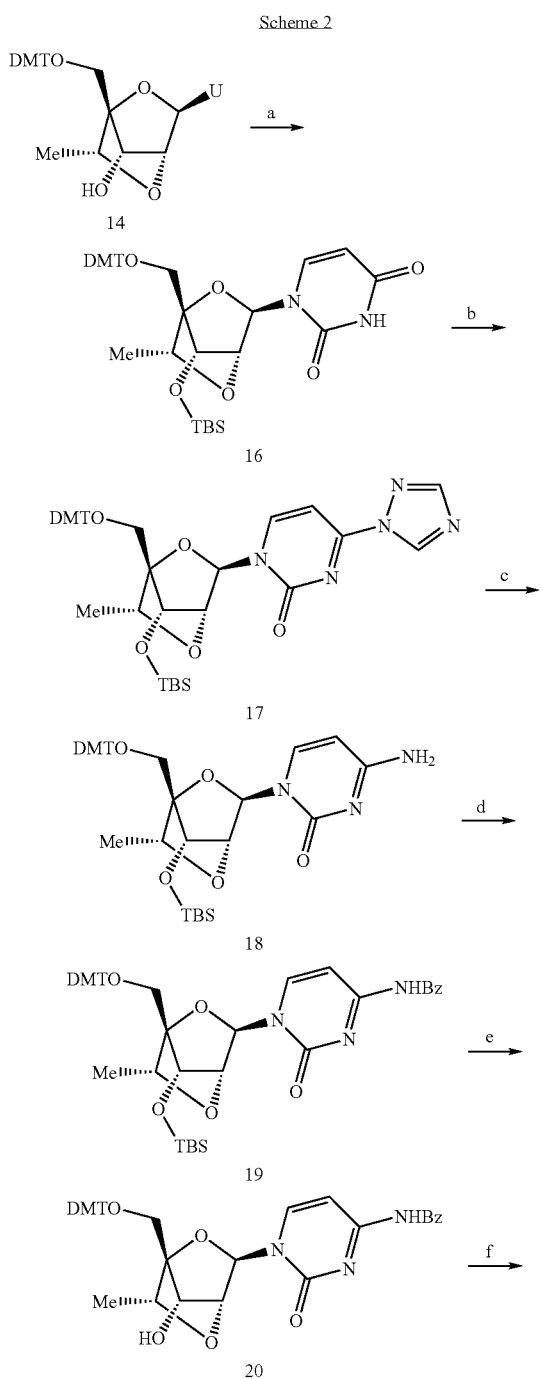

Scheme 2

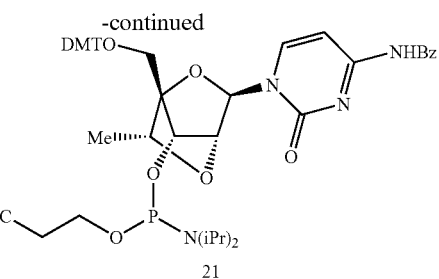

(a) TBSCl, Imidazole, DMF, rt, 16 h 99%;
(b) POCl$_3$, 1,2,4-Triazole, Et$_3$N, CH$_3$CN, rt, 4 h;
(c) Aqueous NH$_3$, 1,4-dioxane, rt, 16 h;
(d) Bz$_2$O, DMF, rt, 16 h, 90% from 15;
(e) Et$_3$N·3HF, Et$_3$N, THF, rt, 16 h, 93%;
(f) CNCH$_2$CH$_2$OP(N-iPr$_2$)$_2$, Tetrazole, NMI, DMF, 95%.

A) Nucleoside (16)

tert-Butyldimethylsilyl chloride (0.79 g, 5.2 mmol) was added to a solution of nucleoside 14 (1.0 g, 1.7 mmol) and imidazole (0.70 g, 10.4 mmol) in DMF (3.5 mL). After stirring at rt for 16 h, the reaction was poured into EtOAc and the organic phase was sequentially extracted with brine, dried (Na$_2$SO$_4$) and concentrated under vacuum. Purification by column chromatpography (SiO$_2$, eluting with 50% EtOAc/hexanes) provided nucleoside 16 (1.17 g, 99%) as a white solid.

B) Nucleoside (19)

Phosphorus oxychloride (1.27 mL, 13.6 mmol) was added to a cold (0° C.) suspension of 1,2,4-triazole (4.0 g, 58.0 mmol) in CH$_3$CN (21 mL). After stirring for 15 min, triethylamine (9.57 mL, 68 mmol) was added to the reaction and the stirring continued for 30 min. A solution of nucleoside 16 (1.17 g, 1.7 mmol) in CH$_3$CN (10 mL) was added to the reaction at 0° C. After stirring for 10 min, the ice bath was removed and the reaction was stirred at rt for 4 h. The solvent was then removed under vacuum and the residue was partitioned between EtOAc and water. The organic layer was then washed with saturated NaHCO$_3$, brine, dried (Na$_2$SO$_4$) and concentrated under vacuum to provide crude 17, which was used without any further purification.

Aqueous ammonia (4 mL) was added to a solution of nucleoside 17 (from above) in dioxane (20 mL). After stirring at rt for 16 h, the reaction was concentrated under vacuum and dried over high vacuum for 8 h to provide nucleoside 18, which was used without any further purification.

Benzoic anhydride (0.65 g, 2.9 mmol) was added to a solution of nucleoside 18 (from above) in DMF (3 mL). After stirring at rt for 16 h, the reaction was poured into EtOAc and the organic layer was extracted with saturated NaHCO$_3$, brine, dried (Na$_2$SO$_4$) and concentrated under vacuum. Purification by column chromatography (SiO$_2$, eluting with 50% EtOAc/hexanes) provided nucleoside 19 (1.2 g, 90% from 16) as a white solid.

C) Nucleoside (20)

Triethylamine trihydrofluoride (1.48 mL, 9.1 mmol) was added to a solution of nucleoside 19 (1.86 g, 3.7 mmol) and triethylamine (1.03 mL, 7.3 mmol) in THF (15 mL) a polypropylene tube. After stirring at rt for 16 h, the reaction was concentrated under vacuum and the residue was dissolved in EtOAc and the organic layer was sequentially washed with water, saturated NaHCO$_3$, brine, dried (Na$_2$SO$_4$) and concentrated under vacuum. Purification by column chromatography (SiO$_2$, eluting with 5% MeOH/CHCl$_3$) provided nucleoside 20 (0.91 g, 90%) as a white solid. $^1$H NMR (MeOD) δ: 8.62 (d, 1H), 8.02 (d. 1H), 7.63 (m, 6H), 7.38 (m, 7H), 6.96 (d, 4H), 6.65 s, 1H), 4.49 (s, 1H), 4.36 (s, 1H), 4.25 (m, 1H), 3.53 (d, 1H), 3.41 (d, 1H), 1.18 (d, 3H).

D) (1S,3R,4R,6R,7S)-7-[2-Cyanoethoxy(diisopropylamino)phosphinoxy]-1-(4,4% dimethoxytrityloxymethyl)-3-(4-N-benzoylcytosin-1-yl)-6-methyl-2,5-dioxa-bicyclo-[2.2.1]heptane (21)

2-Cyanoethyl tetraisopropylphorodiamidite (0.63 mL, 2.0 mmol) was added to a solution of nucleoside 20 (0.89 g, 1.3 mmol), tetrazole (73 mg, 1.1 mmol) and N-methylimidazole (26 μL, 0.33 mmol) in DMF (6.6 mL). After stirring at rt for 8 h, the reaction was poured into EtOAc and the organic layer was washed with 90% brine, brine, dried (Na$_2$SO$_4$) and concentrated. The residue was dissolved in minimum amount of EtOAc and this solution was added to hexanes. The resulting precipitate was collected and further purified by column chromatography (SiO$_2$, eluting with 75% to 90% EtOAc/hexanes) to provide phosphoramidite 21 as a white solid (1.1 g, 95%). $^{31}$P NMR (CDCl$_3$) δ: 149.34, 149.77.

Example 3

Preparation of uridine-6-(S)-methyl BNA phosphoramidite, (1S,3R,4R,6S,7S)-7-[2-cyanoethoxy(diisopropylamino)phosphin oxy]-1-(4,4'-dimethoxytrityloxymethyl)-3-(uracil-1-yl)-6-methyl-2,5-dioxa-bicyclo[2.2.1]heptane (38)

Scheme 3

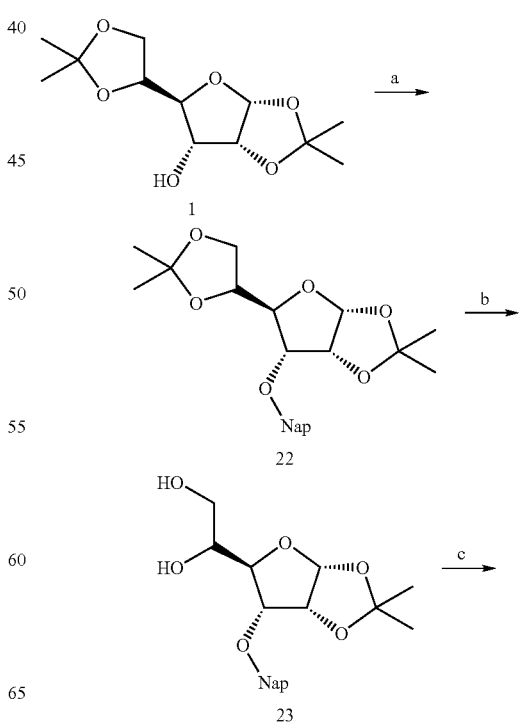

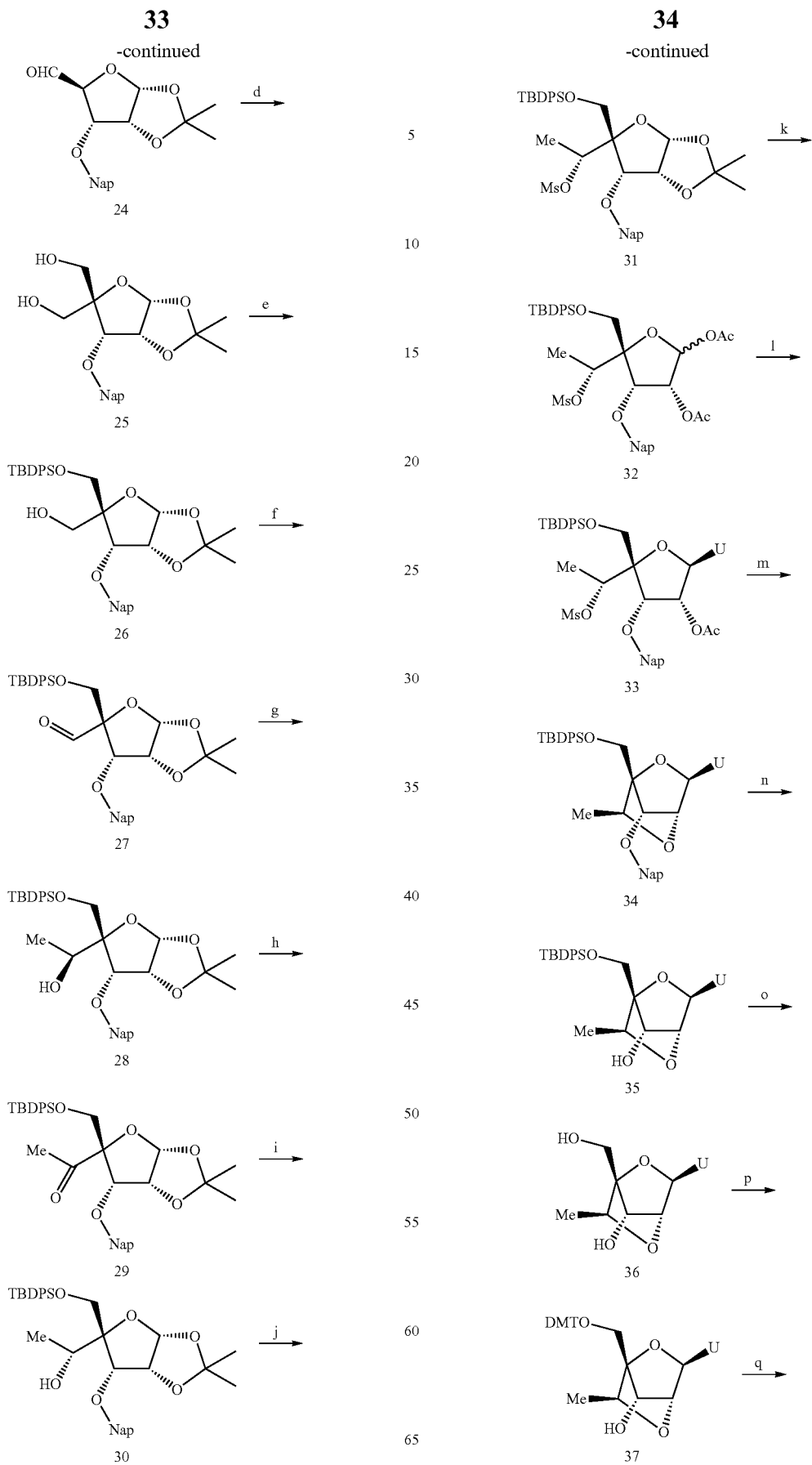

-continued

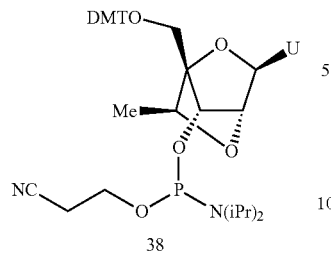

(a) NaH, naphthyl bromide, DMF, rt, 2 h, 98%;
(b) Acetic acid, H₂O, rt, 16 h;
(c) NaIO₄, dioxane, H₂O, rt, 90 minutes;
(d) HCHO, NaOH, THF, H₂O, rt, 16 h, 80% from 22;
(e) TBDPSCl, Et₃N, DMAP, CH₂Cl₂, rt, 16 h, 61%;
(f) Oxalyl chloride, DMSO, Et₃N, -78° C.;
(g) MeMgBr, CeCl₃, 89% from 26;
(h) Oxalyl Chloride, DMSO, Et₃N, -78° C.;
(i) DiBAL, CH₂Cl₂, -78° C.;
(j) MsCl, Et₃N, DMAP, CH₂Cl₂, rt, 1 h;
(k) Ac₂O, AcOH, H₂SO₄, 58% from 28;
(l) BSA, Uracil, TMSOTf, MeCN, reflux, 2 h;
(m) K₂CO₃, MeOH, rt, 16 h, 76% from 34;
(n) DDQ, CH₂Cl₂, H₂O, rt 8 h, 80%;
(o) Et₃N•3HF, Et₃N, THF, quant.;
(p) DMTCl, pyridine, rt, 16 h, 86%;
(q) CN(CH₂)₂OP(NiPr₂)₂, tetrazole, NMI, DMF, 97%.

A) Alcohol (22)

Sodium hydride (2.39 g, 59.8 mmol) was added carefully to a cold (0° C.) solution of commercially available 1,2:5,6-Di-O-isopropylidene-α-D-allofuranose 1 (12.0 g, 46 mmol) in DMF (75 mL). After stirring for 20 minutes, napthyl bromide (11.12 g, 50.8 mmol) was added to the reaction and the stirring was continued for another 2 h. The reaction was carefully quenched with H₂O and then poured into EtOAc and the organic layer was washed with water, brine, dried and concentrated. Purification by column chromatography (SiO₂, 10% to 33% EtOAc/hexanes) provided alcohol 22 as a white solid (18.1 g, 98%).

B) Diol (25)

Alcohol 22 (18 g, 46 mmol) was dissolved in glacial acetic acid (150 mL) and H₂O (60 mL). The reaction was stirred at rt for 16 h after which it was concentrated under vacuum. The residue was then dissolved in EtOAc and the organic layer was washed with saturated NaHCO₃, brine, dried and concentrated to provide crude 23, which was used without any further purification.

A solution of sodium periodate (48 mmol, 10 g) in water (350 mL) was added to a solution of the crude diol 23 obtained above, in 1,4-dioxane (140 mL). After stirring at rt for 90 minutes, the reaction was extracted with EtOAc and the organic layer was further washed with water, brine, dried (Na₂SO₄) and concentrated to provide aldehyde 24, which was used without any further purification.

The crude aldehyde 24 from above, was dissolved in a mixture of THF:H₂O (1:1, 100 mL) and the reaction was cooled in an ice bath. Formaldehyde (25 mL, 35% w/w) and 1N NaOH (100 mL) were added to the reaction. After stirring at rt for 16 h, formaldehyde (5 mL) was added to the reaction and the stirring was continued for an additional 32 h. The reaction was then concentrated to dryness and the residue was partitioned between EtOAc and water. The layers were separated and the organic layer was washed with additional 1N NaOH, water, brine, dried and concentrated to provide diol 25 (12.96 g, 80%, three steps) as a white solid.

C) Alcohol (26)

tert-Butyldiphenylsilyl chloride (0.75 mL, 2.9 mmol) was added to a cold (0° C.) solution of diol 25 (1 g, 2.8 mmol) and triethylamine (0.45 mL, 3.2 mmol). After stirring at rt for 16 h, the reaction was poured into EtOAc and sequentially washed with 5% HCl, saturated NaHCO₃, brine, dried (Na₂SO₄) and concentrated. Purification by column chromatography (SiO₂, eluting with 10% to 40% EtOAc/hexanes) provided alcohol 26 (1.02 g, 61%) as an oil (0.42 g of the regioisomeric silyl protected diol was also isolated).

D) Alcohol (28)

Dimethylsulfoxide (1.6 mL, 22.4 mmol) was added dropwise to a cold (-78° C.) solution of oxalyl chloride (0.98 mL, 11.2 mmol) in CH₂Cl₂ (70 mL). After stirring for 30 min, a solution of alcohol 26 (4.8 g, 8.0 mmol) in CH₂Cl₂ (20 mL) was added to the reaction. The stirring was continued for 45 min at -78° C. and triethylamine (4.72 mL, 33.7 mmol) was added to the reaction. The reaction was stirred at ~78° C. for 15 min after which the ice bath was removed and the reaction was allowed to gradually warm over 45 min. The reaction was then poured into CH₂Cl₂ and the organic phase was sequentially washed with 5% aqueous HCl, saturated NaHCO₃, brine, dried (Na₂SO₄) and concentrated under vacuum to provide aldehyde 27, which was used without any further purification.

A suspension of cerium III chloride (2.96 g, 12.0 mmol) in THF (50 mL) was stirred at rt for 90 min. The reaction was cooled in an ice bath and methyl magnesium bromide (8.6 mL of a 1.4 M solution in THF, 12 mmol) was added over 5 min and the stirring continued for another 90 min after which the reaction was cooled to -78° C. A solution of crude aldehyde 27 (from above) in THF (20 mL) was added to the reaction. After stirring for another 90 min, the reaction was quenched with sat NH₄Cl solution and poured into EtOAc. The organic layer was sequentially washed with 5% aqueous HCl, saturated NaHCO₃, brine, dried (Na₂SO₄) and concentrated under vacuum. Purification by column chromatography (SiO₂, eluting with 20% EtOAc/hexanes) provided alcohol 28 (4.37 g, 89% from 26).

E) Diacetate (32)

Dimethylsulfoxide (1.41 mL, 19.9 mmol) was added dropwise to a cold (-78° C.) solution of oxalyl chloride (0.87 mL, 10.0 mmol) in CH₂Cl₂ (70 mL). After stirring for 30 min, a solution of alcohol 28 (4.35 g, 7.1 mmol) in CH₂Cl₂ (20 mL) was added to the reaction. The stirring was continued for 45 min at -78° C. and triethylamine (4.20 mL, 30.0 mmol) was added to the reaction. The reaction was stirred at -78° C. for 15 min after which the ice bath was removed and the reaction was allowed to gradually warm over 45 min. The reaction was then poured into CH₂Cl₂ and the organic phase was sequentially washed with 5% aqueous HCl, saturated NaHCO₃, brine, dried (Na₂SO₄) and concentrated under vacuum to provide ketone 29, which was used without any further purification.

Diisobutyl aluminum hydride (13.7 mL of a 1M solution in CH₂Cl₂, 13.7 mmol) was added to a cold solution of ketone 29 (from above) in CH₂Cl₂ (15 mL). After stirring for 2 h at -78° C., the reaction was quenched by the addition of saturated NH₄Cl and poured into CHCl₃. The organic layer was then sequentially washed with 5% aqueous HCl, saturated NaHCO₃, brine, dried (Na₂SO₄) and concentrated under vacuum to provide alcohol 30 which was used without any further purification.

Methanesulfonyl chloride (0.11 mL, 1.4 mmol) was added to a cold (0° C.) solution of alcohol 30 (from above), triethylamine (1.77 mL, 10.5 mmol) and 4-dimethylaminopyridine (85 mg, 0.7 mmol) in CH₂Cl₂ (21 mL). After stirring at rt for 1 h, the reaction was poured into CHCl₃ and the organic layer was sequentially washed with 5% aqueous HCl, saturated NaHCO₃, brine, dried (Na₂SO₄) and concentrated under vacuum to provide mesylate 31, which was used without any purification.

Concentrated H₂SO₄ (2 drops) was added to a solution of mesylate 31 (from above) in glacial acetic acid (15 mL) and acetic anhydride (3.0 mL). After stirring at rt for 1 h, the reaction was poured into EtOAc and the organic layer was washed with water, saturated NaHCO₃, brine, dried (Na₂SO₄) and concentrated under vacuum. Purification by column chromatography (SiO₂, eluting with 20% to 33% EtOAc/hexanes) provided diacetate 32 (3.0 g, 58% from 28).

F) Nucleoside (34)

N,O-Bis(trimethylsilyl)acetamide (3.45 mL, 14.0 mmol) was added to a suspension of diacetate 32 (3.0 g, 4.1 mmol) and uracil (0.57 g, 5.1 mmol) in CH₃CN (20 mL). After heating at 40° C. for 15 min to get a clear solution, trimethylsilyl triflate (0.95 mL, 5.3 mmol) was added to the reaction. After refluxing for 2 h, the reaction was cooled to rt and poured into EtOAc. The organic layer was washed with saturated NaHCO₃, brine, dried (Na₂SO₄) and concentrated under vacuum to provide crude nucleoside 33, which was used without any purification.

K₂CO₃ (1.66 g, 12.0 mmol) was added to a solution of nucleoside 33 (from above) in MeOH (40 mL). After stirring at rt for 16 h, the reaction was concentrated under vacuum and the residue was dissolved in 25% pyridine/EtOAc and extracted with brine, dried (Na₂SO₄) and concentrated under vacuum. Purification by column chromatography (SiO₂, eluting with 40% EtOAc/hexanes) provided nucleoside 34 (2.0 g, 76% from 32) as a white solid.

G) Nucleoside (35)

2,3-dichloro-5,6-dicyano-1,4-benzoquinone (DDQ) (1.4 g, 6.2 mmol) was added to a solution of nucleoside 34 (2.0 g, 3.1 mmol) in dichloromethane (30 mL) and H₂O (1.5 mL). After stirring for 3 h at rt, additional DDQ (0.5 g) was added to the reaction. After stirring for another 10 minutes, the reaction was concentrated under vacuum and the residue was dissolved in EtOAc. The organic layer was then sequentially washed with water, water:saturated NaHCO₃ (1:1), brine, dried (Na₂SO₄) and concentrated. Purification by column chromatography (SiO₂, 80% EtOAc/hexanes) provided nucleoside 35 (1.25 g, 80%) as a white solid.

H) Nucleoside (36)

Triethylamine trihydroflouride (2.4 mL, 14.7 mmol) was added to a solution of nucleoside 35 (1.25 g, 2.5 mmol) and triethlyamine (1.0 mL, 7.4 mmol) in THF (25 mL) in a polypropylene tube. After stirring at rt for 24 h, the reaction was concentrated under vacuum and the residue was dissolved in EtOAc. The organic layer was then washed with water, saturated NaHCO₃, brine, dried and concentrated (Na₂SO₄). Purification by column chromatography (SiO₂, eluting with 5% to 10% MeOH/CHCl₃) provided nucleoside 36 (0.88 g) as a white solid (product contaminated with Et₃N).

I) Nucleoside (37)

Dimethoxytrityl chloride (0.91 g, 2.7 mmol) was added to a solution of nucleoside 36 (from above) in pyridine (12 mL). After stirring at rt for 16 h, the reaction was poured into EtOAc and the organic layer was washed with brine, dried and concentrated. Purification by column chromatography (SiO₂, eluting with 90% EtOAc/hexanes) provided nucleoside 37 (1.28 g, 86% from 36) as a white solid.

J) (1S,3R,4R,6S,7S)-7-[2-Cyanoethoxy(diisopropylamino)phosphin oxy]-1-(4,4'-dimethoxytrityloxymethyl)-3-(uracil-1-yl)-6-methyl-2,5-dioxa-bicyclo [2.2.1]heptane (38)

2-Cyanoethyl tetraisopropylphorodiamidite (0.46 mL, 1.5 mmol) was added to a solution of nucleoside 37 (0.59 g, 1.0 mmol), tetrazole (57 mg, 0.82 mmol) and N-methylimidazole (20 μL, 0.25 mmol) in DMF (5 mL). After stirring at it for 8 h, the reaction was poured into EtOAc and the organic layer was washed with 90% brine, brine, dried (Na₂SO₄) and concentrated. Purification by column chromatography (SiO₂, eluting with 66% to 75% EtOAc/hexanes) provided phosphoramidite 38 as a white solid (0.75 g, 97%). ³¹P NMR (CDCl₃) δ: 149.36, 149.53.

Example 4

Preparation of N-Bz-cytosine-6-(S)-methyl BNA phosphoramidite, 2.2 Preparation of (1S,3R,4R,6S, 7S)-7-[2-cyanoethoxy(diisopropylamino)phosphin oxy]-1-(4,4'-dimethoxytrityloxymethyl)-3-(4-N-benzoylcytosin-1-yl)-6-methyl-2,5-dioxa-bicyclo[2.2.1] heptane (44)

Scheme 4

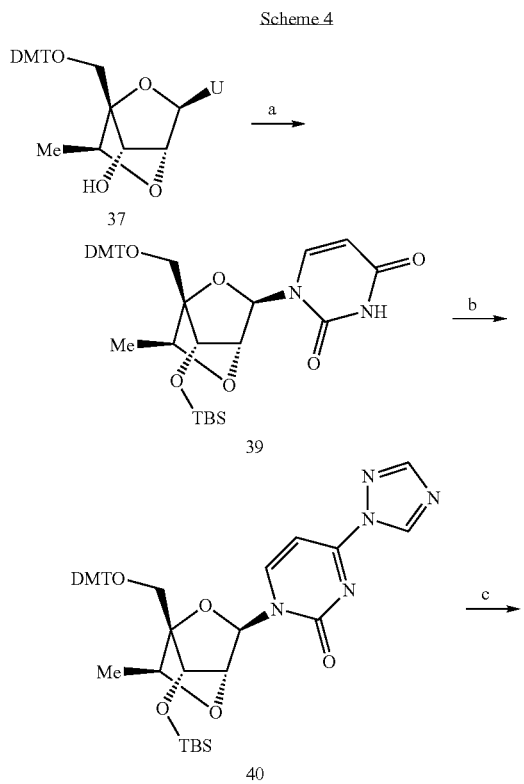

-continued

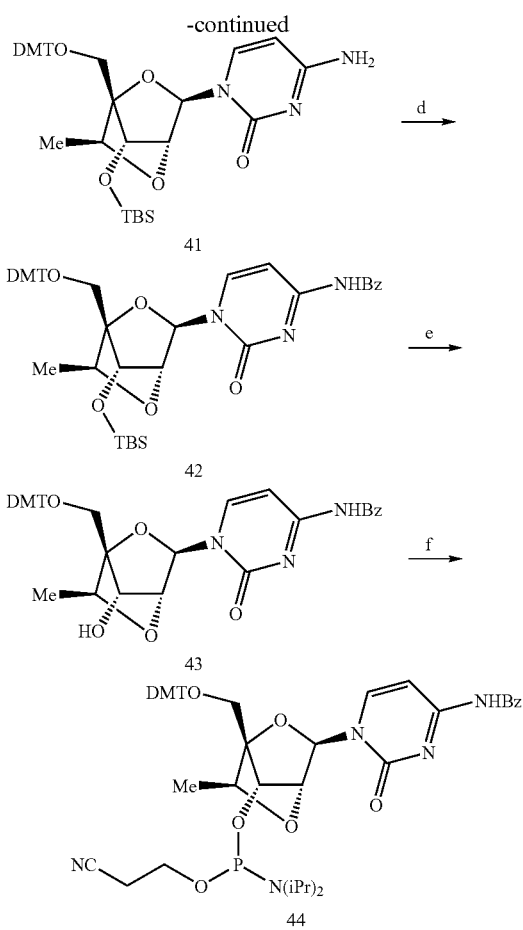

(a) TBSCl, Et₃N, DMAP, CH₂Cl₂, rt, 16 h 97%;
(b) POCl₃, 1,2,4-Triazole, Et₃N, CH₃CN, rt, 4 h;
(c) Aqueous NH₃, 1,4-dioxane, rt, 16 h;
(d) Bz₂O, DMF, rt, 16 h, 91% from 39;
(e) Et₃N·3HF, Et₃N, THF, rt, 16 h, 87%;
(f) CNCH₂CH₂OP(N-iPr₂)₂, Tetrazole, NMI, DMF, 90%.

A) Nucleoside (39)

tert-Butyldimethylsilyl chloride (0.45 g, 3.0 mmol) was added to a solution of nucleoside 37 (0.59 g, 1.0 mmol) and imidazole (0.41 g, 6.0 mmol) in DMF (2 mL). After stirring at rt for 16 h, the reaction was poured into EtOAc and the organic phase was sequentially extracted with brine, dried (Na₂SO₄) and concentrated under vacuum. Purification by column chromatpography (SiO₂, eluting with 50% EtOAc/hexanes) provided nucleoside 39 (0.68 g, 97%) as a white solid.

B) Nucleoside (42)

Phosphorus oxychloride (0.74 mL, 8.0 mmol) was added to a cold (0° C.) suspension of 1,2,4-triazole (2.35 g, 34.0 mmol) in CH₃CN (16 mL). After stirring for 15 min, triethylamine (5.6 mL, 40 mmol) was added to the reaction and the stirring continued for 30 min. A solution of nucleoside 39 (0.68 g, 1.0 mmol) in CH₃CN (7 mL) was added to the reaction at 0° C. After stirring for 10 min, the ice bath was removed and the reaction was stirred at rt for 4 h. The solvent was then removed under vacuum and the residue was partitioned between EtOAc and water. The organic layer was then washed with saturated NaHCO₃, brine, dried (Na₂SO₄) and concentrated under vacuum to provide crude 40, which was used without any further purification.

Aqueous ammonia (2.5 mL) was added to a solution of nucleoside 40 (from above) in dioxane (12 mL). After stirring at it for 16 h, the reaction was concentrated under vacuum and dried over high vacuum for 8 h to provide nucleoside 41, which was used without any further purification.

Benzoic anhydride (0.38 g, 1.7 mmol) was added to a solution of nucleoside 41 (from above) in DMF (2 mL). After stirring at it for 16 h, the reaction was poured into EtOAc and the organic layer was extracted with saturated NaHCO₃, brine, dried (Na₂SO₄) and concentrated under vacuum. Purification by column chromatography (SiO₂, eluting with 50% EtOAc/hexanes) provided nucleoside 42 (0.72 g, 91% from 39) as a white solid.

C) Nucleoside (43)

Triethylamine trihydrofluoride (0.89 mL, 5.5 mmol) was added to a solution of nucleoside 42 (0.72 g, 0.91 mmol) and triethylamine (0.30 mL, 2.2 mmol) in THF (9 mL) a polypropylene tube. After stirring at it for 16 h, the reaction was concentrated under vacuum and the residue was dissolved in EtOAc and the organic layer was sequentially washed with water, saturated NaHCO₃, brine, dried (Na₂SO₄) and concentrated under vacuum. Purification by column chromatography (SiO₂, eluting with 25% to 40% acetone/CHCl₃) provided nucleoside 43 (0.53 g, 87%) as a white solid. ¹H NMR (CDCl₃): δ 8.34 (s, br, 1H), 8.33 (d, 1H), 7.83 (d, 1H), 7.57-7.26 (m, 16H), 6.89 (d, 4H), 5.72 (s, 1H), 4.75 (s, 1H), 4.22 (s, 1H), 4.14 (m, 1H), 3.83 (s, 6H), 3.63 (d, 1H), 3.46 (s, 1H), 1.20 (d, 3H).

D) (1S,3R,4R,6S,7S)-7-[2-Cyanoethoxy(diisopropylamino)phosphin oxy]-1-(4,4% dimethoxytrityloxymethyl)-3-(4-N-Benzoylcytosin-1-yl)-6-methyl-2,5-dioxa-bicyclo[2.2.1]heptane (44)

2-Cyanoethyl tetraisopropylphorodiamidite (0.37 mL, 1.2 mmol) was added to a solution of nucleoside 43 (0.89 g, 1.3 mmol), tetrazole (43 mg, 0.63 mmol) and N-methylimidazole (16 μL, 0.20 mmol) in DMF (4 mL). After stirring at it for 8 h, the reaction was poured into EtOAc and the organic layer was washed with 90% brine, brine, dried (Na₂SO₄) and concentrated. Purification by column chromatography (SiO₂, eluting with 75% to 90% EtOAc/hexanes) provided phosphoramidite 44 as a white solid (0.61 g, 90%).

Example 5

(1S,3R,4R,6S,7S)-7-[2-Cyanoethoxy(diisopropylamino)phosphin oxy]-1-(4,4'-dimethoxytrityloxymethyl)-3-(6-N-benzoyladenin-9-yl)-6-methyl-2,5-dioxa-bicyclo[2.2.1]heptane (51)

Scheme 5

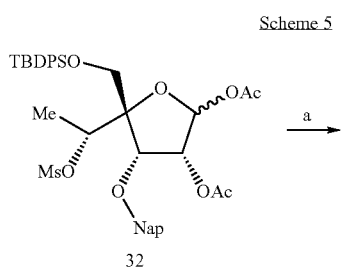

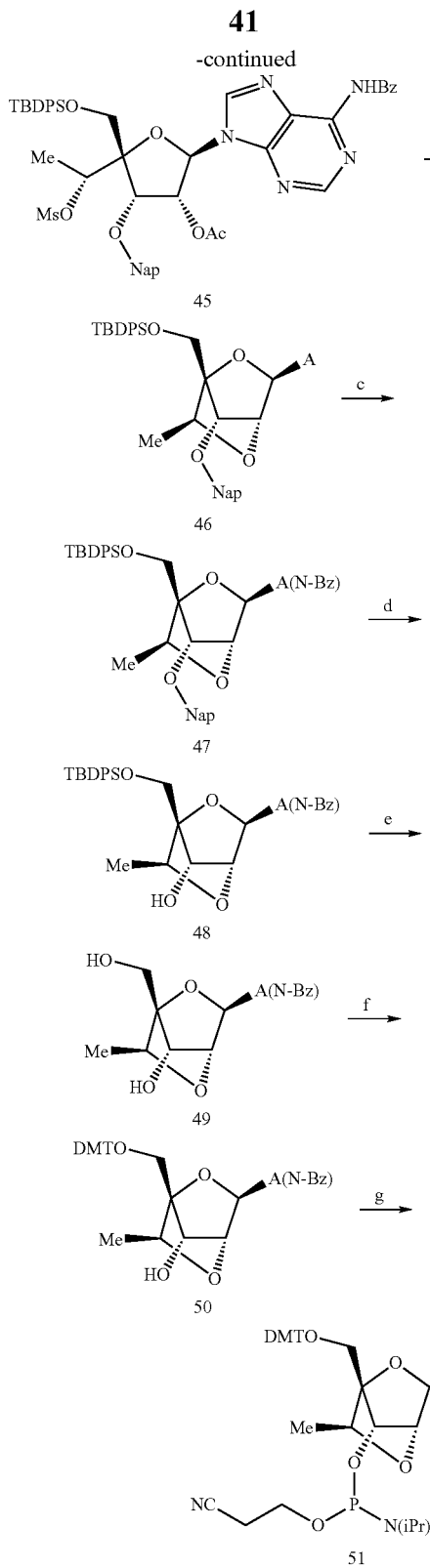

(a) 6-N-Benzoyladenine, BSA, TMSOTf, DCE, reflux, 8 h;
(b) K₂CO₃, MeOH, rt, 16 h, 73% from 32;
(c) Bz₂O, DMF, rt;
(d) DDQ, CH₂Cl₂, H₂O, rt;
(e) Et₃N•3HF, Et₃N, THF, rt, 16 h;
(f) DMTCl, Pyridine, rt, 16 h;
(g) CNCH₂CH₂OP(N-iPr₂)₂, Tetrazole, NMI, DMF.

A) Nucleoside (46)

N,O-Bis(trimethylsilyl)acetamide (1.1 mL, 4.50 mmol) was added to a suspension of diacetate 32 (1.0 g, 1.4 mmol) and 6-N-benzoyladenine (0.48 g, 2.0 mmol) in dichloroethane (14 mL). The reaction mixture turned clear after refluxing 45 minutes and was cooled in an ice bath and trimethylsilyl triflate (0.49 mL, 2.7 mmol) was added. After refluxing for 8 hours the reaction was cooled to room temperature and poured into EtOAc. The organic layer was washed with saturated NaHCO₃ and brine then dried (Na₂SO₄) and concentrated under vacuum to provide crude nucleoside 45, which was used without purification.

K₂CO₃ (0.38 g, 2.7 mmol) was added to a solution of nucleoside 45 (from above) in MeOH (14 mL). After stirring at room temperature for 24 hours the reaction was concentrated under vacuum. The residue was suspended in EtOAc, extracted with water and brine then dried (Na₂SO₄) and concentrated under vacuum. Purification by column chromatography (SiO₂, eluting with 1 to 2.5% MeOH/CHCl₃) provided nucleoside 46 as a white solid (0.69 g, 73% from 32).

B) Nucleoside 47

Nucleoside 47 is prepared from nucleoside 46 by reaction with benzoic anhydride (1.5-2 eq) in dry DMF.

C) Phosphoramidite 51

Phosphoramidite 51 is prepared from nucleoside 47 using the procedures illustrated in Example 3 for the phosphoramidite 38 from nucleoside 34.

Example 6

(1S,3R,4R,6R,7S)-7-[2-Cyanoethoxy(diisopropylamino)phosphin oxy]-1-(4,4'-dimethoxytrityloxymethyl)-3-(6-N-benzoyladenin-9-yl)-6-methyl-2,5-dioxa-bicyclo[2.2.1]heptane (60)

Scheme 6

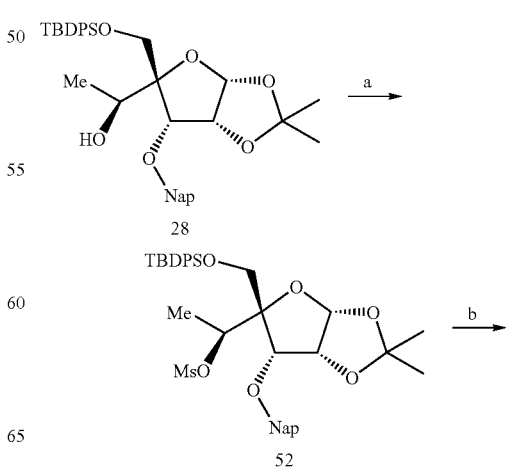

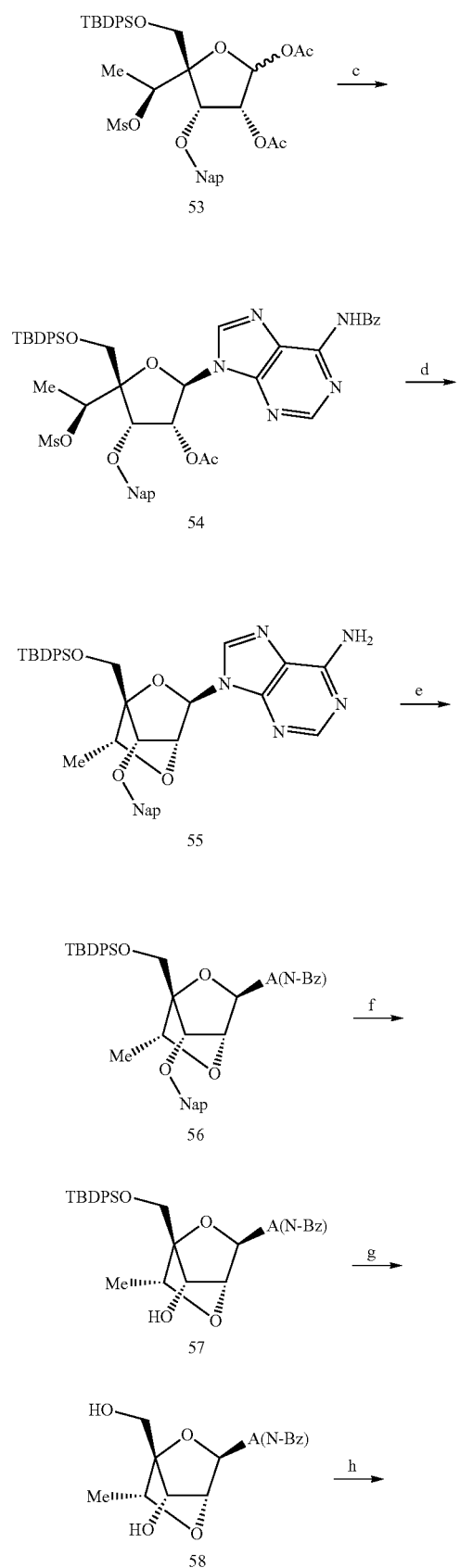

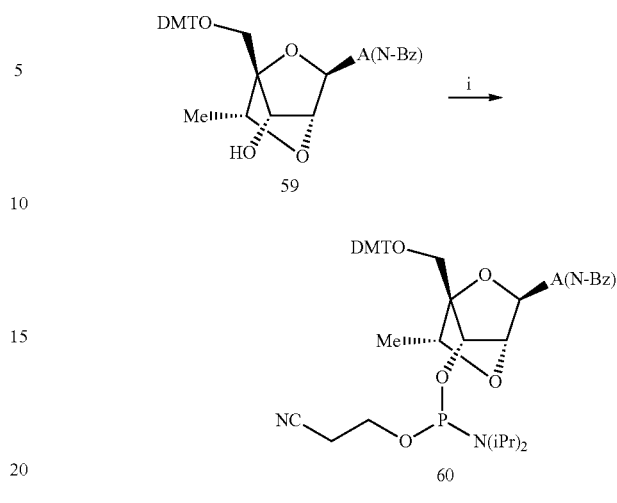

(a) MsCl, Et$_3$N, DMAP, CH$_2$Cl$_2$, rt, 4 h;
(b) Ac$_2$O, AcOH, cat. H$_2$SO$_4$, rt, 3 h, 87% from 28;
(c) 6-N-Benzoyladenine, BSA, TMSOTf, DCE, reflux, 2 h;
(d) K$_2$CO$_3$, MeOH, rt, 16 h;
(e) Bz$_2$O, DMF, rt; (f) DDQ, CH$_2$Cl$_2$, H$_2$O, rt;
(g) Et$_3$N•3HF, Et$_3$N, THF, rt, 16 h;
(h) DMTCl, Pyridine, rt, 16 h;
(i) CNCH$_2$CH$_2$OP(N-iPr$_2$)$_2$, Tetrazole, NMI, DMF.

A) Diacetate (52)

Methanesulfonyl chloride (1.33 mL, 16.8 mmol) was added dropwise to a cold (0° C.) solution of alcohol 28 (7.37 g, 12.0 mmol), triethylamine (2.82 mL, 20.2 mmol) and DMAP (0.20 g, 1.1 mmol) in dichloromethane (25 mL). After stirring for 2 hours at room temperature, the reaction was diluted with dichloromethane and the organic layer was washed with 5% HCl, saturated sodium bicarbonate solution, brine, dried (Na$_2$SO$_4$) and concentrated. The crude mesylate 52 thus obtained was used without further purification.

B) Diacetate (53)

Concentrated sulfuric acid (10 drops) was added to a solution of mesylate 52 (from above) in acetic anhydride (7.2 mL) and acetic acid (36 mL). After stirring at room temperature for 2 hours the reaction was concentrated under high vacuum. The residue was dissolved in ethyl acetate and the organic layer was carefully washed with water, saturated sodium bicarbonate solution (until pH>8) and brine then dried (Na$_2$SO$_4$) and concentrated. The residue was purified by column chromatography (SiO$_2$, eluting with 25 to 35% EtOAc/hexanes) to provide diacetate 53 (7.66 g, 87% from 28) as a viscous oil.

C) Phosphoramidite (60)

Phosphoramidite 60 is prepared from diacetate 53 using the procedures illustrated in Example 3 for the phosphoramidite 51 from diacetate 32.

Example 7

(1S,3R,4R,6S,7S)-7-[2-Cyanoethoxy(diisopropylamino)phosphin oxy]-1-(4,4'-dimethoxytrityloxymethyl)-3-(2-N-Isobutyrylguanin-9-yl)-6-methyl-2,5-dioxa-bicyclo[2.2.1]heptane (67)

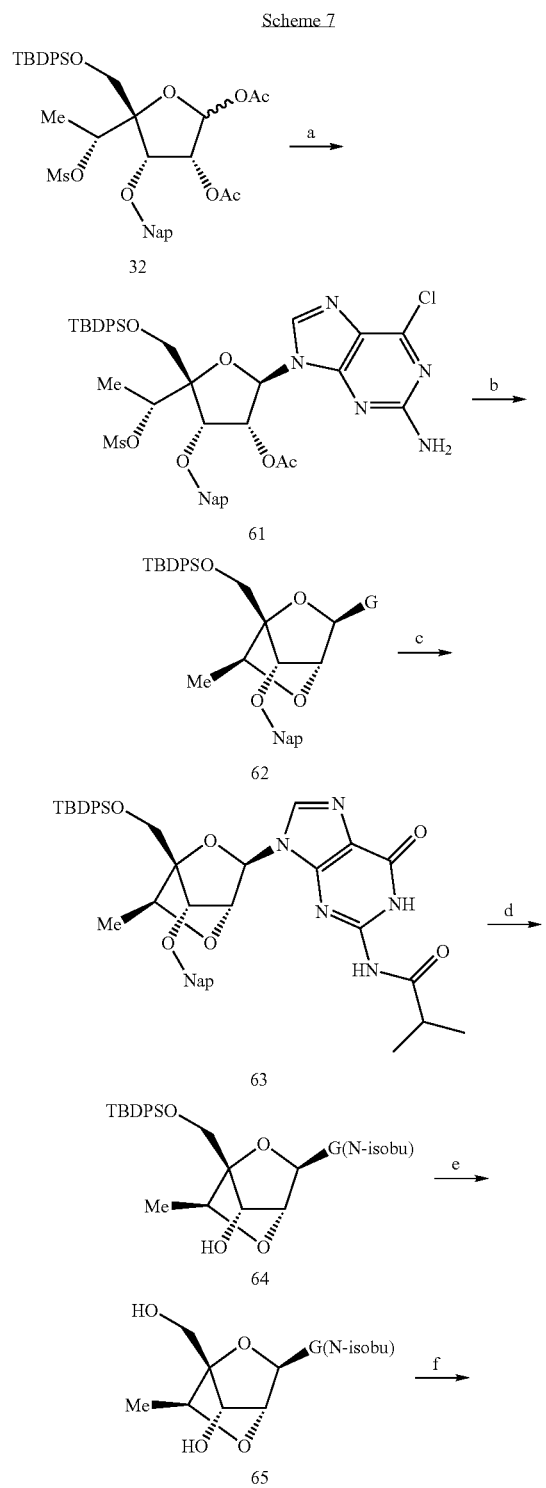

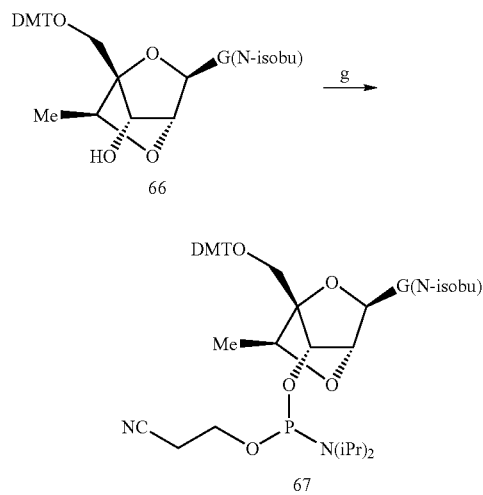

(a) 2-amino-6-chloropurine, BSA, TMSOTf, DCE, reflux, 2 h;
(b) 3-Hydroxypropionitrile, NaH, THF, 4 h, 82% from 32;
(c) Isobutyric anhydride, DMAP, DMF, 60C, 24 h, 71%;
(d) DDQ, CH$_2$Cl$_2$, H$_2$O, rt, 16 h, 91%;
(e) Et$_3$N.3HF, Et$_3$N, THF, rt, 16 h 97%;
(f) DMTCl, Pyridine, rt, 16 h, 85%;
(g) CNCH$_2$CH$_2$OP(N-iPr$_2$)$_2$, Tetrazole, NMI, DMF.

A) Nucleoside (61)

N,O-Bis(trimethylsilyl)acetamide (3.8 mL, 15.5 mmol) was added to a suspension of diacetate 32 (3.44 g, 4.7 mmol) and 2-amino-6-chloropurine (1.18 g, 7.0 mmol) in dichloroethane (46 mL). After refluxing 45 minutes to get a clear solution, the reaction was cooled in an ice bath and trimethylsilyl triflate (1.69 mL, 9.4 mmol) was added. After refluxing for 8 hours the reaction was cooled to room temperature and poured into chloroform. The organic layer was washed with saturated NaHCO$_3$ and brine then dried (Na$_2$SO$_4$) and concentrated under vacuum to provide crude nucleoside 61, which was used without purification.

B) Nucleoside (62)

3-Hydroxypropionitrile (1.67 mL, 24.5 mmol) was added dropwise to a stirring suspension of sodium hydride (1.07 g, 27.0 mmol, 60% w/w) in dry THF (10 mL). After stirring for 20 minutes, a solution of crude nucleoside 61 (from above) in dry THF (25 mL) was added. The stirring was continued for 5 hours at room temperature after which, the reaction was carefully quenched by the addition of a solution of saturated ammonium chloride. The reaction was poured into ethyl acetate and the organic layer was extracted with brine, dried (Na$_2$SO$_4$) and concentrated. Purification of the residue by column chromatography (SiO$_2$, eluting with CHCl$_3$ to 2.5% MeOH/CHCl$_3$) provided nucleoside 62 (3.18 g, 82% from 32) as a light brown solid.

C) Nucleoside (63)

Isobutyric anhydride (1.5 mL, 9.3 mmol) was added to a solution of nucleoside 62 (3.19 g, 4.6 mmol) and 4-dimethylaminomethylpyridine (0.11 g, 0.93 mmol) in DMF (27 mL). After stirring at 60° C. for 14 hours an additional amount of isobutyric anhydride (1.5 mL, 9.3 mmol) was added to the reaction and the stirring was continued at 60° C. for another 12 hours. The reaction was the cooled to room temperature, diluted with EtOAc and the organic layer was washed with water, saturated sodium bicarbonate solution, brine, dried (Na$_2$SO$_4$) and concentrated. Purification by column chromatography (SiO$_2$, 5% to 10% acetone/CHCl$_3$) provided nucleoside 63 (2.5 g, 71%) as a yellowish foam.

D) Nucleoside (64)

DDQ (1.12 g, 5.0 mmol) was added to a solution of nucleoside 63 (2.5 g, 3.3 mmol) in dichloromethane (33 mL) and H$_2$O (1.7 mL). After stirring for 2 hours at room temperature additional DDQ (1.0 g) was added. Stirring was continued at room temperature for another 6 hours after which, the reaction was stored in the refrigerator (4° C.) for 16 hours. The reaction was then concentrated under vacuum and the residue was dissolved in ethyl acetate. The organic layer was washed with water, 10% sodium bisulfite solution (2×), saturated sodium bicarbonate solution and brine then dried (Na$_2$SO$_4$) and concentrated. Purification by column chromatography (SiO$_2$, eluting with 5% MeOH/CHCl$_3$) provided nucleoside 64 (1.84 g, 91%).

E) Nucleoside (65)

Triethylamine trihydroflouride (2.88 mL, 17.9 mmol) was added to a solution of nucleoside 64 (1.84 g, 3.0 mmol) and triethylamine (1.25 mL, 8.9 mmol) in THF (30 mL) in a polypropylene tube. After stirring at room temperature for 24 hours the reaction was concentrated under vacuum and the residue was dissolved in EtOAc. The organic layer was then washed with water, saturated NaHCO$_3$ and brine then dried (Na$_2$SO$_4$) and concentrated. Purification by column chromatography (SiO$_2$, eluting with 5% to 10% MeOH/CHCl$_3$) provided nucleoside 65 (1.05 g, 97%) as a white solid.

F) Nucleoside (66)

Dimethoxytrityl chloride (1.07 g, 3.2 mmol) was added to a solution of nucleoside 65 (1.00 g, 2.7 mmol) in pyridine (13 mL). After stirring at room temperature for 16 hours the reaction was poured into EtOAc and the organic layer was washed with brine, dried and concentrated. Purification by column chromatography (SiO$_2$, eluting with 2.5 to 5% MeOH/CHCl$_3$) provided nucleoside 66 (1.52 g, 85%) as a white foam.

G) (1S,3R,4R,6S,7S)-7-[2-Cyanoethoxy(diisopropylamino)phosphin oxy]-1-(4,4'-dimethoxytrityloxymethyl)-3-(2-N-Isobutyrylguanin-9-yl)-6-methyl-2,5-dioxa-bicyclo[2.2.1]heptane (67)

2-Cyanoethyl tetraisopropylphosphordiamidite (1.06 mL, 3.4 mmol) was added to a solution of nucleoside 66 (1.52 g, 2.2 mmol), tetrazole (0.12 g, 1.7 mmol) and N-methylimidazole (45 µL, 0.56 mmol) in DMF (11 mL). After stirring at room temperature for 8 hours the reaction was poured into EtOAc and the organic layer was washed with 90% brine, brine, dried (Na$_2$SO$_4$) and concentrated. Purification by column chromatography (SiO$_2$, eluting with 2.5% MeOH/ CHCl$_3$) provided phosphoramidite 67 as a white solid (1.65 g, 84%). $^{31}$P NMR (CDCl$_3$) δ: 148.70, 145.81.

Example 8

(1S,3R,4R,6R,7S)-7-[2-Cyanoethoxy(diisopropylamino)phosphin oxy]-1-(4,4'-dimethoxytrityloxymethyl)-3-(2-N-Isobutyrylguanin-9-yl)-6-methyl-2,5-dioxa-bicyclo[2.2.1]heptane (74)

Scheme 8

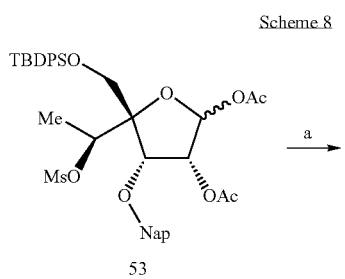

53

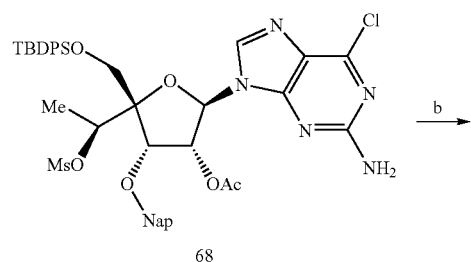

68

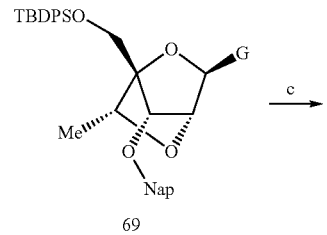

69

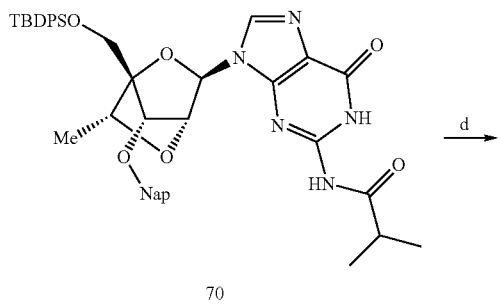

70

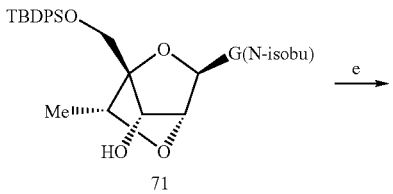

71

49

-continued

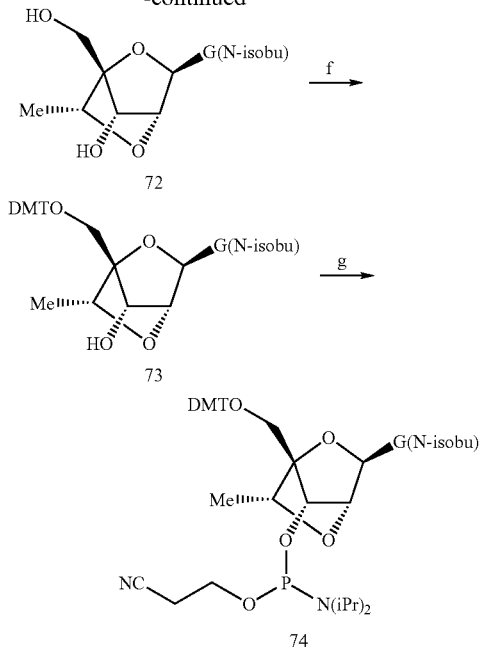

(a) 2-amino-6-chloropurine, BSA, TMSOTf, DCE, reflux, 2 h;
(b) 3-Hydroxypropionitrile, NaH, THF, 4 h;
(c) Isobutyric anhydride, DMAP, DMF, 60C, 24 h;
(d) DDQ, CH$_2$Cl$_2$, H$_2$O, rt, 16 h;
(e) Et$_3$N.3HF, Et$_3$N, THF, rt, 16 h;
(f) DMTCl, Pyridine, rt, 16 h;
(g) CNCH$_2$CH$_2$OP(N-iPr$_2$)$_2$, Tetrazole, NMI, DMF.

The phosphoramidite 74 is prepared from diacetate 53 using the same procedures illustrated for the phosphoramidite 67 from diacetate 32.

Example 9

(1S,3R,4R,6R,7S)-7-[2-Cyanoethoxy(diisopropylamino)phosphin oxy]-1-(4,4'-dimethoxytrityloxymethyl)-3-(uracil-1-yl)-6-methoxymethyl-2,5-dioxabicyclo[2.2.1]heptane (83)

50

-continued

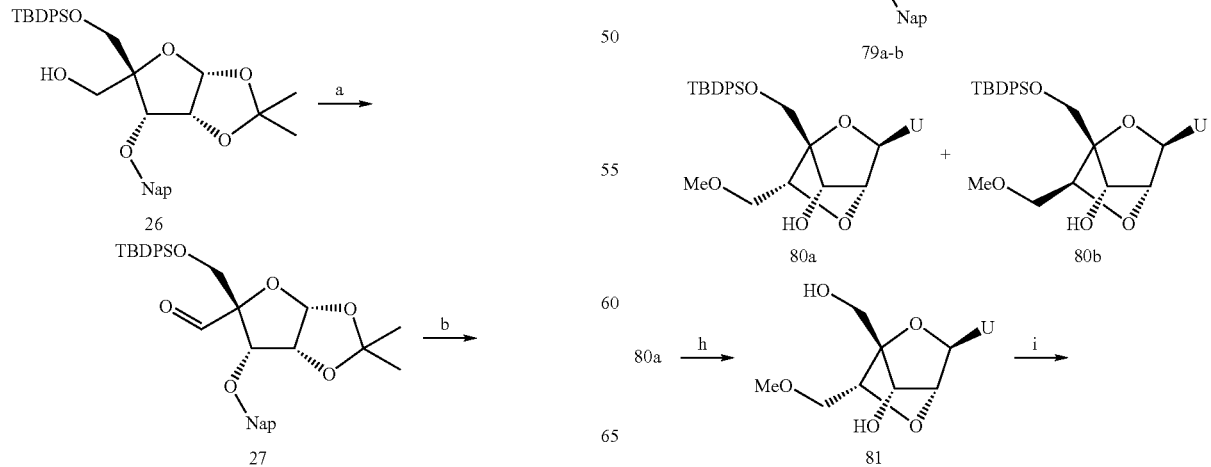

-continued

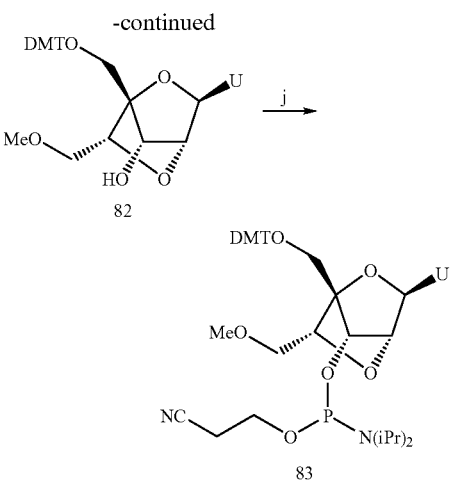

(a) Oxalyl chloride, DMSO, Et₃N, CH₂Cl₂, -78° C.;
(b) MeOCH₂Br, Mg, HgCl₂, THF, -20° C., >95% from 26;
(c) MsCl, Et₃N, DMAP, CH₂Cl₂, 85%;
(d) Ac₂O, AcOH, H₂SO₄, rt, 3 h, 84%;
(e) Uracil BSA, TMSOTf, MeCN, reflux 2 h;
(f) K₂CO₃, MeOH, 89% from 77a-b;
(g) DDQ, CH₂Cl₂, H₂O, 8 h, rt, 98% combined yield for 80a and 80b;
(h) Et₃N.3HF, Et₃N, THF, rt, 16 h;
(i) DMTCL, pyridine, 16 h, rt, 90%;
(j) CN(CH₂)₂OP(N-iPr₂)₂, Tetrazole, NMI, DMF, 96%.

A) Alcohols (75a-b)

Dimethylsulfoxide (3.5 mL, 50.0 mmol) was added to a solution of oxalyl chloride (2.2 mL, 25.0 mmol) in dichloromethane (130 mL) at −78° C. After stirring for 30 minutes a solution of alcohol 26 (10.0 g, 16.7 mmol) in dichloromethane (30 mL) was added to the reaction over 10 minutes. After stirring for another 45 minutes, triethylamine (10.5 mL, 75.0 mmol) was slowly added to the reaction. After the addition was complete, the ice bath was removed and the reaction was gradually allowed to warm up to 0° C. (ca. 1 hour) and transferred to a separatory funnel. The organic layer was sequentially washed with 5% HCl, a solution of saturated sodium bicarbonate and brine then dried (Na₂SO₄) and concentrated to provide aldehyde 27, which was dried under high vacuum (18 hours) and used without further purification.

A mixture of magnesium turnings (2.5 g, 102.8 mmol) and mercury (II) chloride (93 mg, 0.34 mmol) were covered with dry THF (5 mL) and the reaction was cooled to −20° C. A few drops of neat methoxymethyl bromide were added to initiate the reaction. After waiting for a few minutes, a solution of methoxymethyl bromide (9.33 mL, 102.8 mmol) in THF (12 mL) was added (1 mL/10 minutes via a syringe) to the reaction over approximately 3 hours. The temperature of the external bath was very carefully maintained between −20 and −25° C. during the addition. A small volume of dry THF (5 mL) was added intermittently (over 3 hours) to the reaction to facilitate stirring. After the addition of the bromide was complete, the reaction was stirred at −25° C. for 100 minutes and a solution of crude aldehyde (27) in THF (30 mL) was added. After stirring at −20° C. for 45 minutes, no starting aldehyde 27 was detected by TLC. The reaction was carefully quenched with a solution of saturated ammonium chloride and diluted with ethyl acetate. The organic layer was washed with 5% HCl, a saturated solution of sodium bicarbonate and brine then dried (Na₂SO₄) and concentrated. Purification by column chromatography (SiO₂, eluting with 25 to 30% EtOAc/hexanes) provided alcohols 75a-b (quantitative) as a mixture (ca 1:1 of isomers).

B) Mesylates (76a-b)

Methanesulfonyl chloride (2.3 mL, 29.2 mmol) was added to a cold (0° C.) solution of alcohols 75a-b (13.38 g, 20.8 mmol) dissolved in triethylamine (5.3 mL, 37.9 mmol) and DMAP (0.36 g, 2.9 mmol) in dichloromethane (42 mL). After stirring for 2 hours additional methanesulfonyl chloride (0.5 mL) was added. Stirring was continued for 1 hour and the reaction was diluted with chloroform. The organic layer was sequentially washed with 5% HCl, a saturated solution of sodium bicarbonate and brine then dried (Na₂SO₄) and concentrated. Purification by column chromatography (SiO₂, eluting with 20% EtOAc/hexanes) provide mesylates 76a-b (12.8 g, 85%) as viscous oil C) Diacetates (77a-b)

Concentrated sulfuric acid (6 drops) was added to a solution of mesylates 76a-b (12.8 g, 17.8 mmol), acetic acid (50 mL) and acetic anhydride (10 mL). After stirring for 3 hours at room temperature the reaction was judged complete by LCMS and the majority of the solvent was evaporated under high vacuum. The concentrated mixture was diluted with ethyl acetate and the organic layer was washed with water, a saturated solution of sodium bicarbonate (until pH>10) and brine then dried (Na₂SO₄) and concentrated. Purification by column chromatography (SiO₂, eluting with 20% EtOAc/hexanes) provided an anomeric mixture of diacetates 77a-b (11.44 g, 84%) as a viscous oil.

D) Nucleosides (79a-b)

N,O-Bis(trimethylsilyl)acetamide (14.76 mL, 59.9 mmol) was added to a suspension of diacetates 77a-b (11.44 g, 15.0 mmol) and uracil (3.35 g, 29.9 mmol) in CH₃CN (75 mL). After heating at 40° C. for 15 minutes to get a clear solution, the reaction was cooled in an ice bath and trimethylsilyltriflate (4.06 mL, 22.5 mmol) was added. After refluxing for 2 hours the reaction was cooled to room temperature and poured into EtOAc. The organic layer was washed with half saturated sodium bicarbonate solution and brine then dried (Na₂SO₄) and concentrated under vacuum to provide crude nucleosides 78a-b, which were used without purification.

Potassium carbonate (5.30 g, 38.4 mmol) was added to a solution of nucleosides 78a-b (from above) in methanol (130 mL). After stirring at room temperature for 16 hours the reaction was concentrated under vacuum. The residue was dissolved in ethyl acetate and extracted with water and brine then dried (Na₂SO₄) and concentrated under vacuum. Purification by column chromatography (SiO₂, eluting with 5 to 7.5% acetone/chloroform) provided nucleoside 79a-b (9.0 g, 89% from 77a-b) as a white solid.

E) Nucleosides (80a and 80b)

DDQ (20.0 mmol, 4.5 g) was added to a solution of nucleosides 79a-b (9.0 g, 13.3 mmol) in dichloromethane (130 mL) and water (6.5 mL). The biphasic reaction was stirred at room temperature for 2 hours after which additional DDQ (2.75 g was added to the reaction). After another 2 hours additional DDQ (1.1 g) was added to the reaction and the stirring was continued for another 4 hours after which the reaction was stored in a refrigerator for 16 hours. The next morning, LCMS showed traces of nucleosides 79a-b, so additional DDQ (0.9 g) was added to the reaction and the stirring was continued for 2 hours at which point no more nucleosides 79a-b were detected by TLC and LCMS. The solvent was evaporated under vacuum and the residue was partitioned between ethyl acetate and water. The organic layer was washed with sodium bisulfite solution (2×), saturated sodium bicarbonate solution and brine then dried (Na₂SO₄) and concentrated. Purification by column chromatography (SiO₂, eluting 10 to 20% acetone/ chloroform) provided nucleosides 80a (slower running spot) and 80b (faster running spot) respectively (7.0 g combined yield, 98%).

F) Nucleoside (81)

Triethylamine trihydrofluoride (12.2 mL, 74.8 mmol) was added to a solution of nucleoside 80a (6.7 g, 12.5 mmol) and triethylamine (5.2 mL, 37.4 mmol) in THF (120 mL). After stirring at room temperature for 16 hours the reaction was concentrated to dryness under vacuum. The residue was purified by column chromatography (SiO$_2$, eluting with 7.5% to 12.5% MeOH/CHCl$_3$) to provide nucleoside 81 (contaminated with triethylamine.hydrofluoride salt, yield >100%), which was used without further purification.

G) Nucleoside (82)

4,4'-Dimethoxytrityl chloride (DMTCl, 4.8 g, 14.3 mmol) was added to a solution of nucleoside 81 (~12.5 mmol) in pyridine (75 mL). After stirring for 16 hours at room temperature, additional DMTCl (2.4 g) was added to the reaction. After stirring for another 4 hours MeOH (10 mL) was added. After stirring for 30 minutes, the reaction was diluted with ethyl acetate and the organic layer was washed with water and brine then dried (Na$_2$SO$_4$) and concentrated. Purification by column chromatography (SiO$_2$, 60 to 75% EtOAc/hexanes) provided nucleoside 82 (6.73 g, 90%) as a white foam.

H) (1S,3R,4R,6R,7S)-7-[2-Cyanoethoxy(diisopropylamino)phosphin oxy]-1-(4,4'-dimethoxytrityloxymethyl)-3-(uracil-1-yl)-6-methoxymethyl-2,5-dioxabicyclo[2.2.1]heptane (83)

2-Cyanoethyl tetraisopropylphosphordiamidite (1.58 mL, 5.0 mmol) was added to a solution of nucleoside 82 (2.0 g, 3.3 mmol), tetrazole (0.19 g, 2.6 mmol) and N-methylimidazole (68 µL, 0.83 mmol) in DMF (16 mL). After stirring at room temperature for 8 hours the reaction was poured into EtOAc. The organic layer was washed with 90% brine followed by brine then dried (Na$_2$SO$_4$) and concentrated. Purification by column chromatography (SiO$_2$, eluting with 66% to 75% EtOAc/hexanes) provided phosphoramidite 83 as a white solid (2.54 g, 96%). $^{31}$P NMR (CDCl$_3$) δ: 149.78, 149.44.

Example 10

(1S,3R,4R,6S,7S)-7-[2-Cyanoethoxy(diisopropylamino)phosphin oxy]-1-(4,4'-dimethoxytrityloxymethyl)-3-(uracil-1-yl)-6-methoxymethyl-2,5-dioxabicyclo-[2.2.1]heptane (86)

Scheme 10

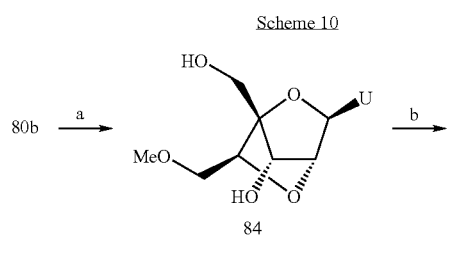

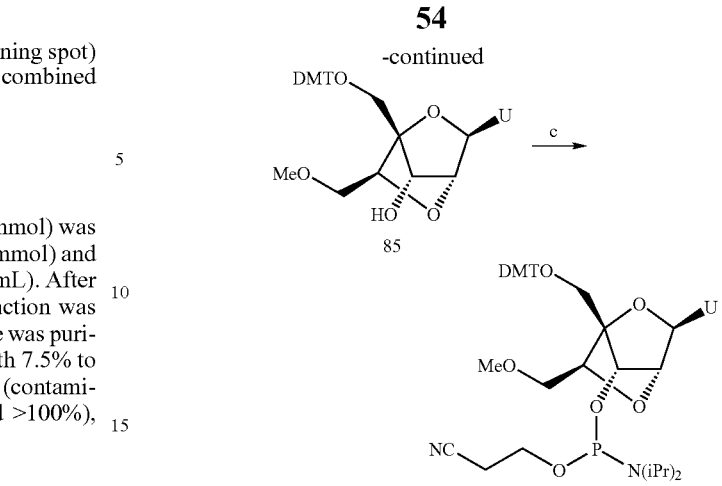

(a) Et$_3$N.3HF, Et$_3$N, THF, rt, 16 h;
(i) DMTCl, pyridine, 16 h, rt, 91%;
(j) CN(CH$_2$)$_2$OP(N-iPr$_2$)$_2$, Tetrazole, NMI, DMF, 96%.

A) Nucleoside (84)

Triethylamine.trihydrofluoride (11.6 mL, 71.5 mmol) was added to a solution of nucleoside 80b (6.43 g, 12.0 mmol) and triethylamine (5.0 mL, 35.7 mmol) in THF (125 mL). After stirring at room temperature for 16 hours the reaction was concentrated to dryness under vacuum. The residue was purified by column chromatography (SiO$_2$, eluting with 7.5% to 12.5% MeOH/CHCl$_3$) to provide nucleoside 84 (contaminated with triethylamine.hydroflouride salt, yield >100%), which was used without further purification.

B) Nucleoside (85)

4,4'-Dimethoxytrityl chloride (DMTCl, 4.6 g, 13.8 mmol) was added to a solution of nucleoside 84 (~12.0 mmol) in pyridine (72 mL). After stirring for 16 hours at room temperature additional DMTCl (2.3 g) was added to the reaction. After stirring for another 4 hours MeOH (10 mL) was added. After stirring for 30 minutes, the reaction was diluted with ethyl acetate and the organic layer was washed with water and brine then dried (Na$_2$SO$_4$) and concentrated. Purification by column chromatography (SiO$_2$, 60 to 75% EtOAc/hexanes) provided nucleoside 85 (6.52 g, 91%) as a white foam.

C) (1S,3R,4R,6S,7S)-7-[2-Cyanoethoxy(diisopropylamino)phosphin oxy]-1-(4,4'-dimethoxytrityloxymethyl)-3-(uracil-1-yl)-6-methoxymethyl-2,5-dioxabicyclo[2.2.1]heptane (86)

2-Cyanoethyl tetraisopropylphosphordiamidite (1.58 mL, 5.0 mmol) was added to a solution of nucleoside 85 (2.0 g, 3.3 mmol), tetrazole (0.19 g, 2.7 mmol) and N-methylimidazole (68 µL, 0.83 mmol) in DMF (17 mL). After stirring at room temperature for 8 hours the reaction was poured into EtOAc. The organic layer was washed with 90% brine then brine and dried (Na$_2$SO$_4$) and concentrated. Purification by column chromatography (SiO$_2$, eluting with 66% to 75% EtOAc/hexanes) provided phosphoramidite 86 as a white solid (2.55 g, 96%). $^{31}$P NMR (CDCl$_3$) δ: 149.97, 149.78.

Example 11

(1S,3R,4R,6R,7S)-7-[2-Cyanoethoxy(diisopropylamino)phosphin oxy]-1-(4,4'-dimethoxytrityloxymethyl)-3-(4-N-Benzoylcytosin-1-yl)-6-methoxymethyl-2,5-dioxa-bicyclo[2.2.1]heptane (92)

Scheme 11

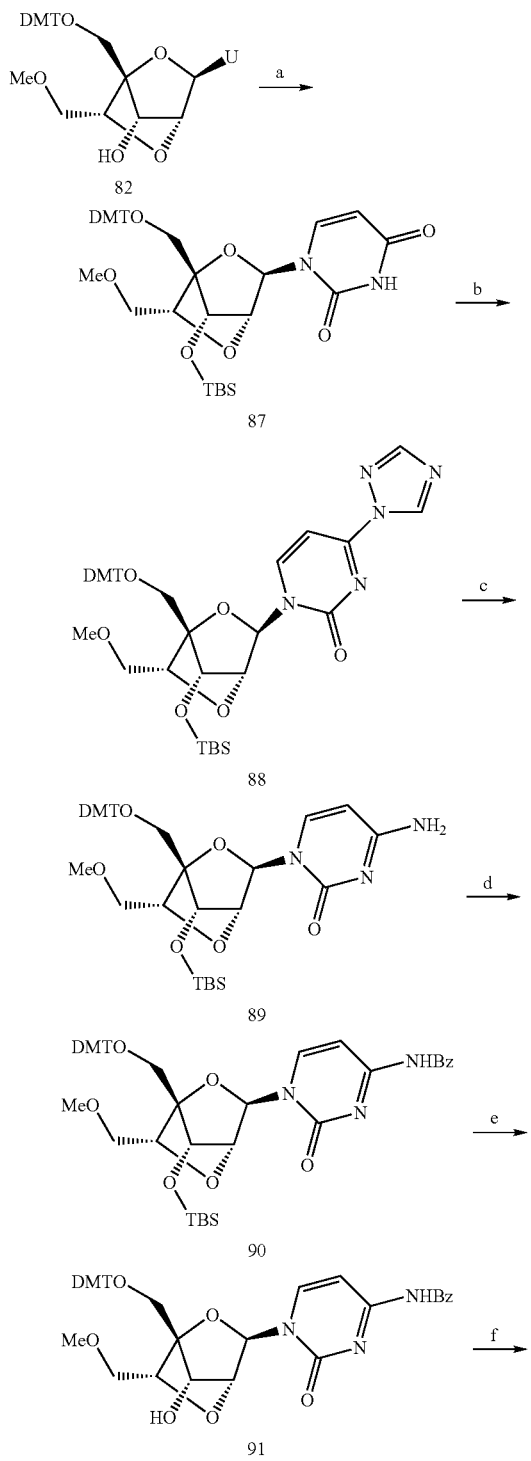

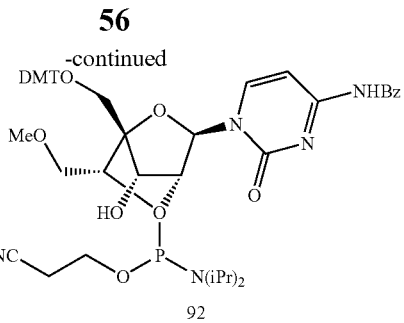

(a) TBSCl, Et₃N, DMAP, CH₂Cl₂, rt, 16 h 98%;
(b) POCl₃, 1,2,4-Triazole, Et₃N, CH₃CN, rt, 4 h;
(c) Aqueous NH₃, 1,4-dioxane, rt, 16 h;
(d) Bz₂O, DMF, rt, 16 h, 91% from 82;
(e) Et₃N·3HF, Et₃N, THF, rt 16 h, 94%;
(f) CNCH₂CH₂OP(N-iPr₂)₂, Tetrazole, NMI, DMF, 84%.

(A) Nucleoside (87)

tert-Butyldimethylsilyl chloride (2.40 g, 15.9 mmol) was added to a solution of nucleoside 82 (3.20 g, 5.3 mmol) and imidazole (2.16 g, 31.8 mmol) in DMF (10.6 mL). After stirring at room temperature for 16 hours the reaction was poured into EtOAc. The organic phase was sequentially extracted with brine, dried (Na₂SO₄) and concentrated under vacuum. Purification by column chromatography (SiO₂, eluting with 50% EtOAc/hexanes) provided nucleoside 87 (3.70 g, 98%) as a white solid.

B) Nucleoside (90)

Phosphorus oxychloride (3.86 mL, 41.4 mmol) was added to a cold (0° C.) suspension of 1,2,4-triazole (12.15 g, 176.1 mmol) in CH₃CN (80 mL). After stirring for 15 minutes triethylamine (29.0 mL, 207.2 mmol) was added and the stirring was continued for 30 minutes. A solution of nucleoside 87 (3.70 g, 5.2 mmol) in CH₃CN (20 mL) was added to the reaction mixture at 0° C. After stirring for 10 minutes the ice bath was removed and the reaction was stirred at room temperature for 4 hours. The solvent was removed under vacuum and the residue was partitioned between EtOAc and water. The organic layer was then washed with saturated NaHCO₃ and brine then dried (Na₂SO₄) and concentrated under vacuum to provide crude 88, which was used without further purification.

Aqueous ammonia (10 mL) was added to a solution of nucleoside 88 (from above) in dioxane (50 mL). After stirring at room temperature for 16 hours the reaction was concentrated under vacuum and dried over high vacuum for 8 hours to provide nucleoside 89, which was used without further purification.

Benzoic anhydride (1.99 g, 8.8 mmol) was added to a solution of nucleoside 89 (from above) in DMF (10 mL). After stirring at room temperature for 16 hours the reaction was poured into EtOAc. The organic layer was extracted with saturated NaHCO₃ and brine then dried (Na₂SO₄) and concentrated under vacuum. Purification by column chromatography (SiO₂, eluting with 50% EtOAc/hexanes) provided nucleoside 90 (3.86 g, 91% from 87) as a white solid.

C) Nucleoside (91)

Triethylamine trihydrofluoride (4.54 mL, 27.9 mmol) was added to a solution of nucleoside 90 (3.81 g, 4.7 mmol) and triethylamine (1.56 mL, 11.2 mmol) in THF (46 mL) a polypropylene tube. After stirring at room temperature for 16 hours the reaction was dried under vacuum and the residue was dissolved in EtOAc. The organic layer was sequentially washed with water, saturated NaHCO₃ and brine then dried (Na₂SO₄) and concentrated under vacuum. Purification by column chromatography (SiO₂, eluting with 5% MeOH/CHCl₃) provided nucleoside 91 (3.07 g, 94%) as a white solid.

D) (1S,3R,4R,6R,7S)-7-[2-Cyanoethoxy(diisopropylamino)phosphin oxy]-1-(4,4'-dimethoxytrityloxymethyl)-3-(4-N-Benzoylcytosin-1-yl)-6-methyl-2,5-dioxa-bicyclo[2.2.1]heptane (92)

2-Cyanoethyl tetraisopropylphosphordiamidite (0.90 mL, 4.3 mmol) was added to a solution of nucleoside 91 (2.0 g, 2.8 mmol), tetrazole (0.16 g, 2.3 mmol) and N-methylimidazole (58 µL, 0.71 mmol) in DMF (14 mL). After stirring at room temperature for 8 hours the reaction was poured into EtOAc. The organic layer was washed with 90% brine followed by brine then dried (Na₂SO₄) and concentrated. The residue was dissolved in minimum amount of EtOAc and this solution was added to hexanes. The resulting precipitate was collected and further purified by column chromatography (SiO₂, eluting with 75% to 90% EtOAc/hexanes) to provide phosphoramidite 92 as a white solid (2.14 g, 84%). ³¹P NMR (CDCl₃) δ: 149.82.

Example 12

(1S,3R,4R,6S,7S)-7-[2-Cyanoethoxy(diisopropylamino)phosphin oxy]-1-(4,4'-dimethoxytrityloxymethyl)-3-(4-N-Benzoylcytosin-1-yl)-6-methoxymethyl-2,5-dioxa-bicyclo[2.2.1]heptane (98)

Scheme 12

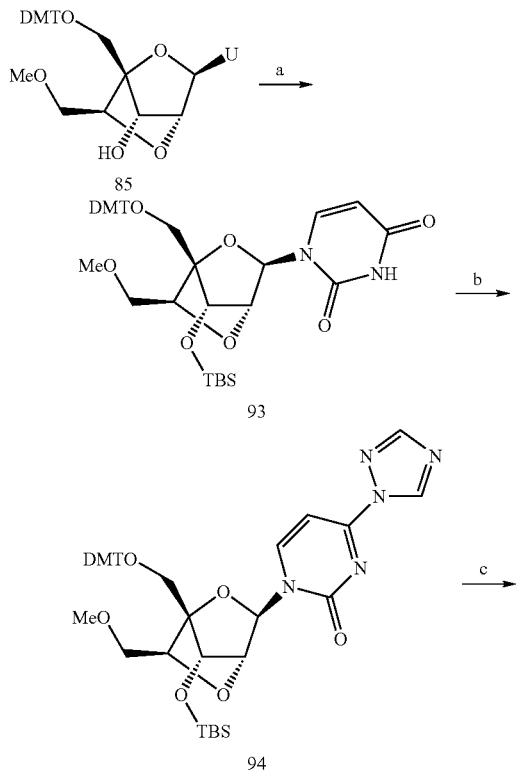

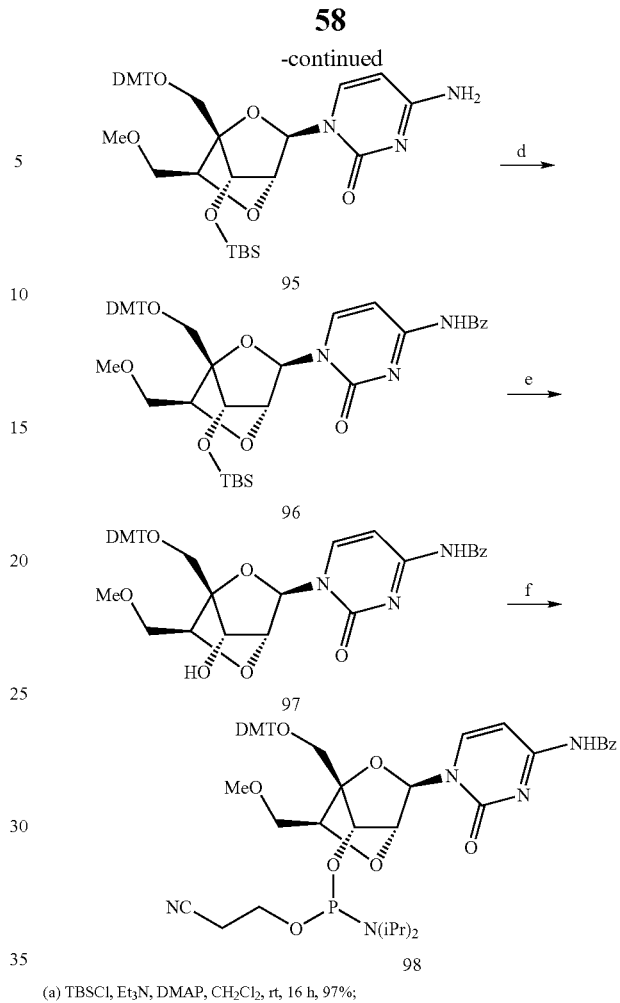

(a) TBSCl, Et₃N, DMAP, CH₂Cl₂, rt, 16 h, 97%;
(b) POCl₃, 1,2,4-Triazole, Et₃N, CH₃CN, rt, 4 h;
(c) Aqueous NH₃, 1,4-dioxane, rt, 16 h;
(d) Bz₂O, DMF, rt, 16 h, 89% from 93;
(e) Et₃N.3HF, Et₃N, THF, rt, 16 h, 89%;
(f) CNCH₂CH₂OP(N-iPr₂)₂, Tetrazole, NMI, DMF, 84%.

A) Nucleoside (93)

tert-Butyldimethylsilyl chloride (2.25 g, 15.0 mmol) was added to a solution of nucleoside 85 (3.0 g, 5.0 mmol) and imidazole (2.03 g, 29.9 mmol) in DMF (10 mL). After stirring at room temperature for 16 hours the reaction was poured into EtOAc. The organic phase was sequentially extracted with brine, dried (Na₂SO₄) and concentrated under vacuum. Purification by column chromatography (SiO₂, eluting with 50% EtOAc/hexanes) provided nucleoside 93 (3.45 g, 97%) as a white solid.

B) Nucleoside (96)

Phosphorus oxychloride (3.59 mL, 38.5 mmol) was added to a cold (0° C.) suspension of 1,2,4-triazole (11.3 g, 163.9 mmol) in CH₃CN (80 mL). After stirring for 15 minutes triethylamine (27.0 mL, 192.8 mmol) was added to the reaction and the stirring continued for 30 minutes. A solution of nucleoside 93 (3.45 g, 4.82 mmol) in CH₃CN (20 mL) was added to the reaction at 0° C. After stirring for 10 minutes the ice bath was removed and the reaction was stirred at room temperature for 4 hours. The solvent was then removed under vacuum and the residue was partitioned between EtOAc and water. The organic layer was then washed with a saturated solution of NaHCO$_3$ and brine then dried (Na$_2$SO$_4$) and concentrated under vacuum to provide crude 94, which was used without further purification.

Aqueous ammonia (10 mL) was added to a solution of nucleoside 94 (from above) in dioxane (50 mL). After stirring at room temperature for 16 hours the reaction was concentrated under vacuum and dried over high vacuum for 8 hours to provide nucleoside 95, which was used without further purification.

Benzoic anhydride (1.63 g, 7.2 mmol) was added to a solution of nucleoside 95 (from above) in DMF (9 mL). After stirring at room temperature for 16 hours the reaction was poured into EtOAc. The organic layer was extracted with saturated NaHCO$_3$ and brine then dried (Na$_2$SO$_4$) and concentrated under vacuum. Purification by column chromatography (SiO$_2$, eluting with 50% EtOAc/hexanes) provided nucleoside 96 (3.53 g, 89% from 93) as a white solid.

C) Nucleoside (97)

Triethylamine trihydrofluoride (4.20 mL, 25.8 mmol) was added to a solution of nucleoside 96 (3.53 g, 4.3 mmol) and triethylamine (1.43 mL, 10.3 mmol) in THF (43 mL) in a polypropylene tube. After stirring at room temperature for 16 hours the reaction was dried under vacuum and the residue was dissolved in EtOAc. The organic layer was sequentially washed with water, saturated NaHCO$_3$ and brine then dried (Na$_2$SO$_4$) and concentrated under vacuum. Purification by column chromatography (SiO$_2$, eluting with 25% to 40% acetone/CHCl$_3$) provided nucleoside 97 (2.87 g, 95%) as a white solid.

D) (1S,3R,4R,6S,7S)-7-[2-Cyanoethoxy(diisopropylamino)phosphin oxy]-1-(4,4% dimethoxytrityloxymethyl)-3-(4-N-Benzoylcytosin-1-yl)-6-methyl-2,5-dioxa-bicyclo[2.2.1]heptane (98)

2-Cyanoethyl tetraisopropylphosphordiamidite (1.35 mL, 4.3 mmol) was added to a solution of nucleoside 97 (2.0 g, 2.8 mmol), tetrazole (0.16 mg, 2.3 mmol) and N-methylimidazole (58 µL, 0.71 mmol) in DMF (14 mL). After stirring at room temperature for 8 hours the reaction was poured into EtOAc and the organic layer was washed with 90% brine followed with brine then dried (Na$_2$SO$_4$) and concentrated. Purification by column chromatography (SiO$_2$, eluting with 75% to 90% EtOAc/hexanes) provided phosphoramidite 98 as a white solid (2.15 g, 84%). $^{31}$P NMR (CDCl$_3$) δ: 150.33.

Example 13

(1S,3R,4R,6R,7S)-7-[2-Cyanoethoxy(diisopropylamino)phosphin oxy]-1-(4,4'-dimethoxytrityloxymethyl)-3-(6-N-Benzoyladenin-9-yl)-6-methoxymethyl-2,5-dioxa-bicyclo[2.2.1]heptane (105)

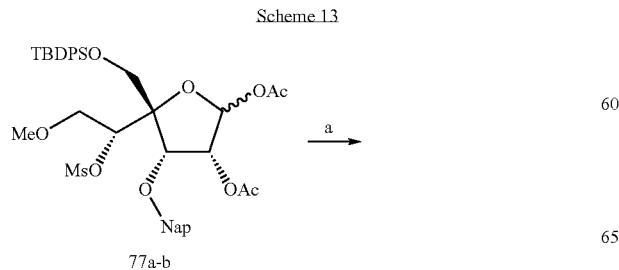

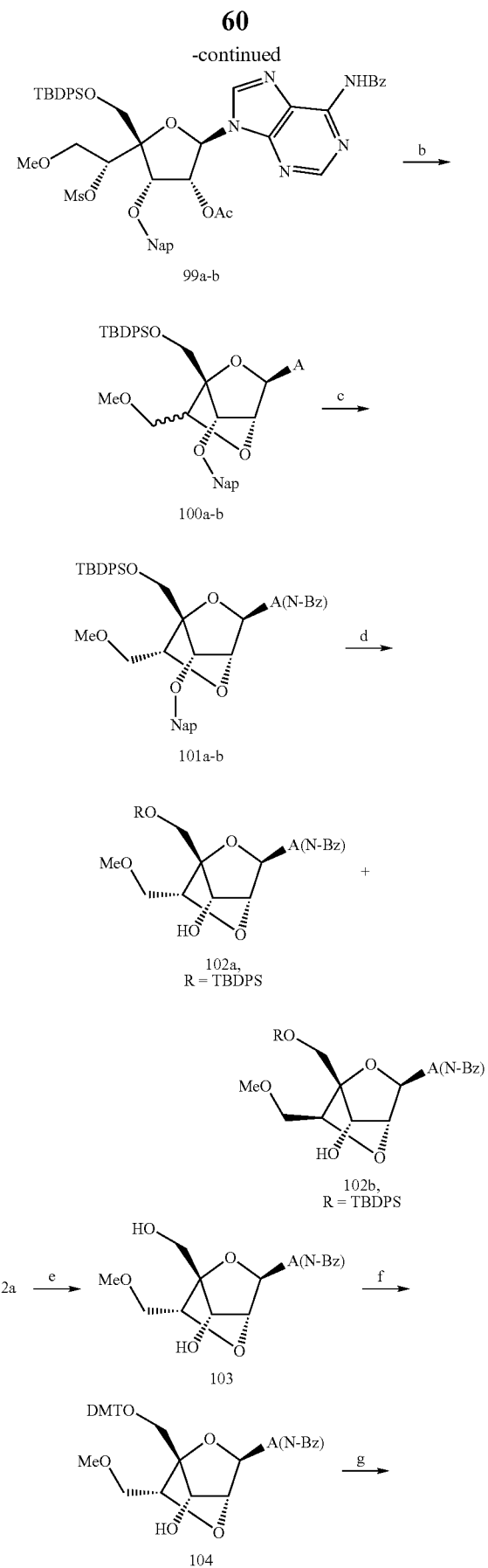

-continued

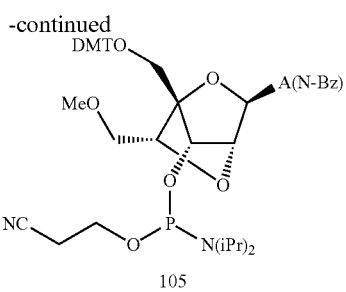
105

(a) 6-N-Benzoyladenine, BSA, TMSOTf, CH₃CN, reflux, 8 h;
(b) K₂CO₃, MeOH, rt, 16 h;
(c) Bz₂O, DMF, rt;
(d) DDQ, CH₂Cl₂, H₂O, rt;
(e) Et₃N.3HF, Et₃N, THF, rt, 16 h;
(f) DMTCl, Pyridine, rt, 16 h;
(g) CNCH₂CH₂OP(N-iPr₂)₂, Tetrazole, NMI, DMF.

Phosphoramidite 105 is prepared from diacetate 77a-b using the procedures illustrated for the synthesis of phosphoramidite 83 from diacetate mixture 77a-b.

Example 14

(1S,3R,4R,6S,7S)-7-[2-Cyanoethoxy(diisopropylamino)phosphin oxy]-1-(4,4'-dimethoxytrityloxymethyl)-3-(6-N-Benzoyladenin-9-yl)-6-methyl-2,5-dioxa-bicyclo[2.2.1]heptane (108)

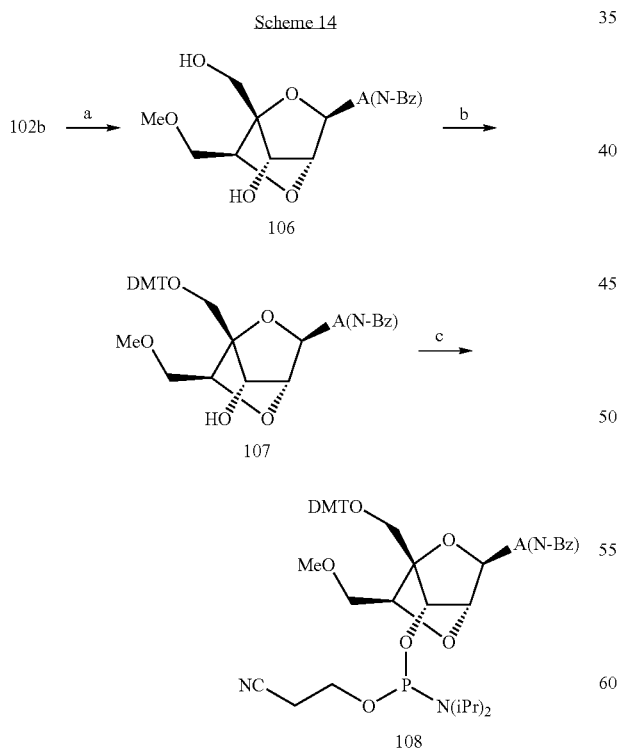

(a) Et₃N.3HF, Et₃N, THF, rt, 16 h;
(b) DMTCl, Pyridine, rt, 16 h;
(c) CNCH₂CH₂OP(N-iPr₂)₂, Tetrazole, NMI, DMF.

Phosphoramidite 108 is prepared from nucleoside 102b using the procedures illustrated for the synthesis of phosphoramidite 86 from 80b.

Example 15

(1S,3R,4R,6R,7S)-7-[2-Cyanoethoxy(diisopropylamino)phosphin oxy]-1-(4,4'-dimethoxytrityloxymethyl)-3-(2-N-Isobutyrylguanin-9-yl)-6-methoxymethyl-2,5-dioxa-bicyclo[2.2.1]heptane (114)

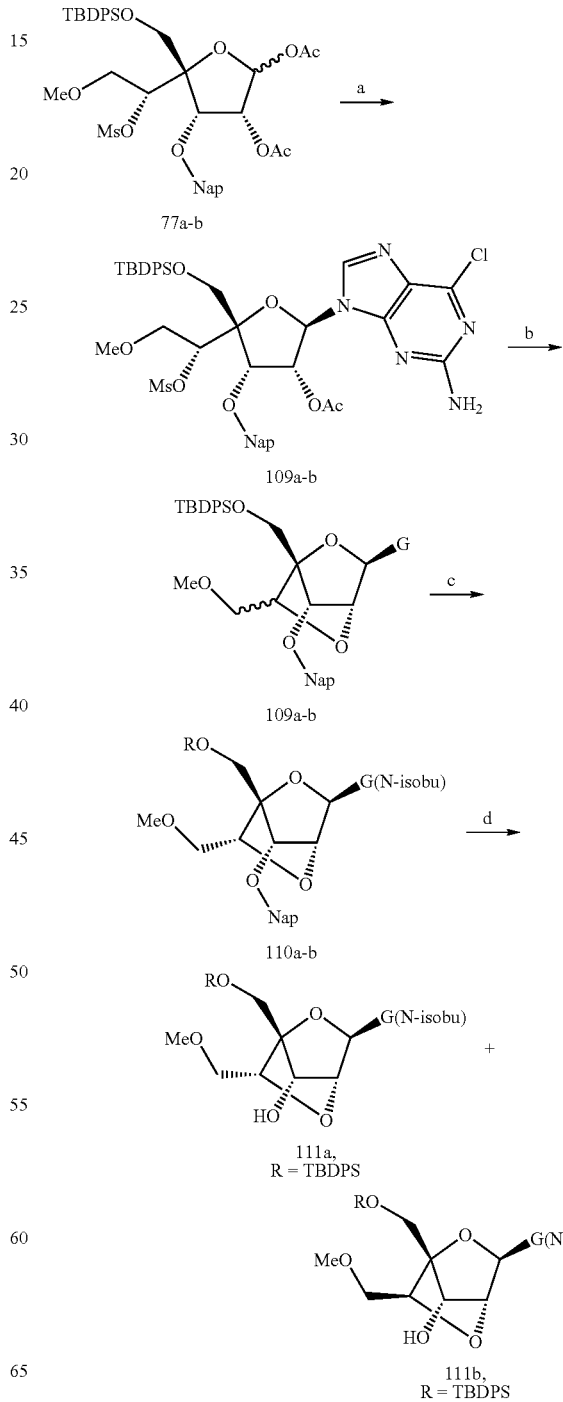

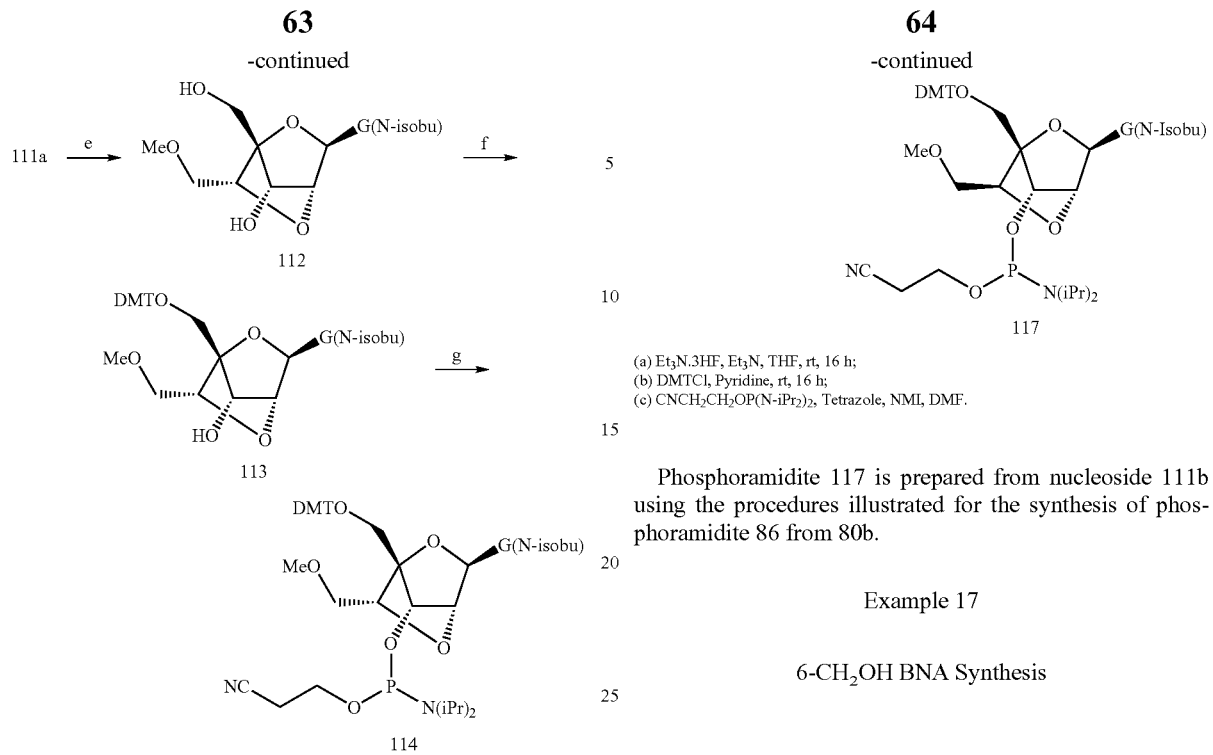

(a) 2-amino-6-chloropurine, BSA, TMSOTf, CH₃CN, reflux, 2 h;
(b) 3-Hydroxypropionitrile, NaH, THF, 4 h;
(c) Isobutyric anhydride, DMAP, DMF 60° C., 24 h;
(d) DDQ, CH₂Cl₂, H₂O, rt, 16 h;
(e) Et₃N.3HF, Et₃N, THF, rt;
(f) DMTCl, Pyridine, rt;
(g) CNCH₂CH₂OP(N-iPr₂)₂, Tetrazole, NMI, DMF.

Phosphoramidite 114 is prepared from diacetate 77a-b using the procedures illustrated for the synthesis of phosphoramidite 83 from diacetate mixture 77a-b.

Example 16

(1S,3R,4R,6S,7S)-7-[2-Cyanoethoxy(diisopropylamino)phosphin oxy]-1-(4,4'-dimethoxytrityloxymethyl)-3-(2-N-Isobutyrylguanin-9-yl)-6-methoxymethyl-2,5-dioxa-bicyclo[2.2.1]heptane (117)

Scheme 16

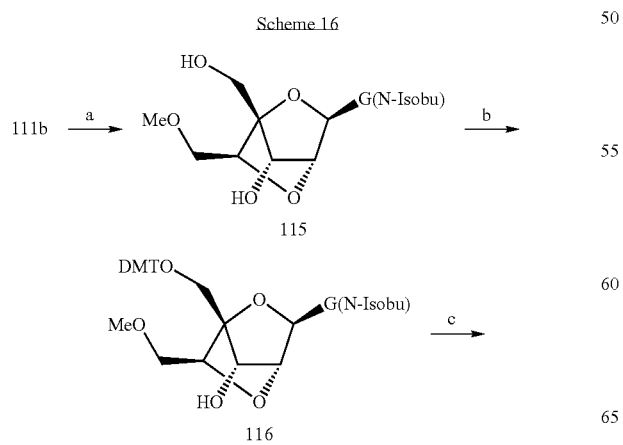

(a) Et₃N.3HF, Et₃N, THF, rt, 16 h;
(b) DMTCl, Pyridine, rt, 16 h;
(c) CNCH₂CH₂OP(N-iPr₂)₂, Tetrazole, NMI, DMF.

Phosphoramidite 117 is prepared from nucleoside 111b using the procedures illustrated for the synthesis of phosphoramidite 86 from 80b.

Example 17

6-CH₂OH BNA Synthesis

Scheme 17

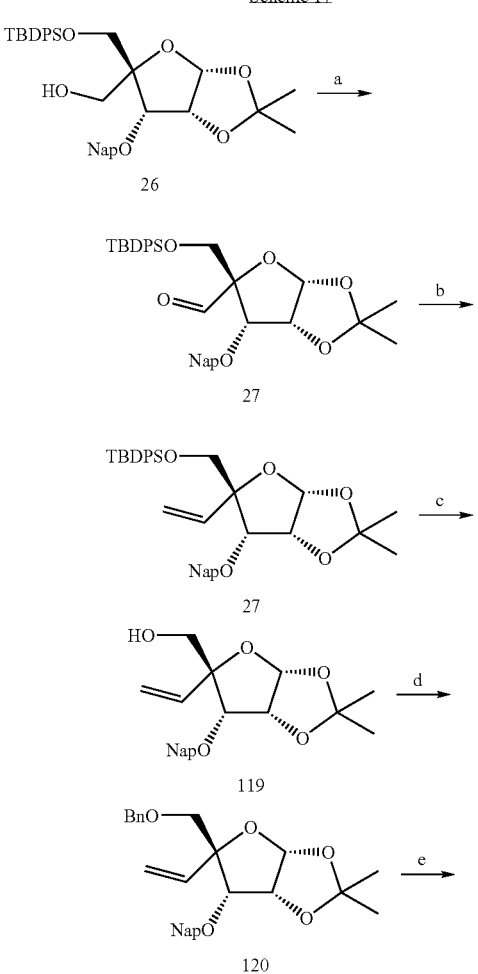

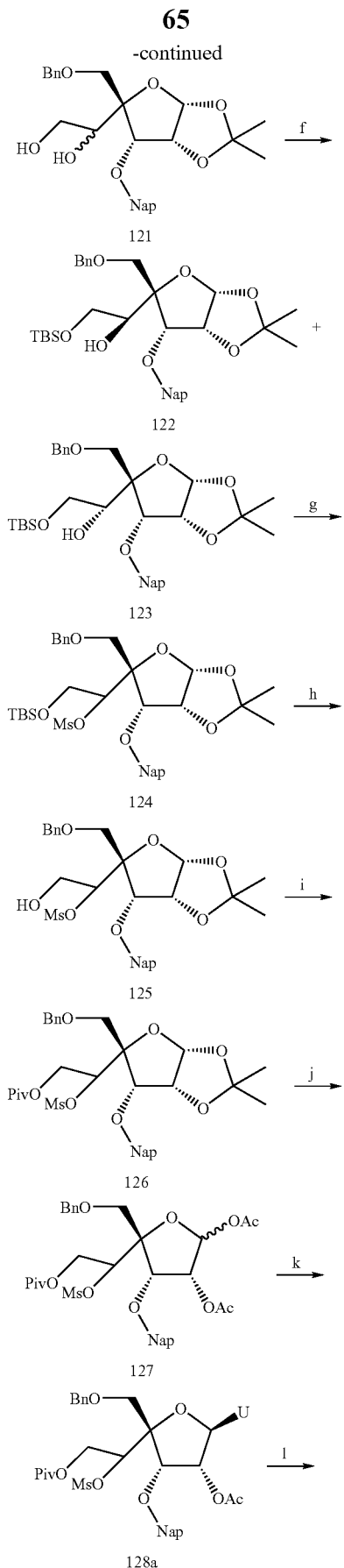

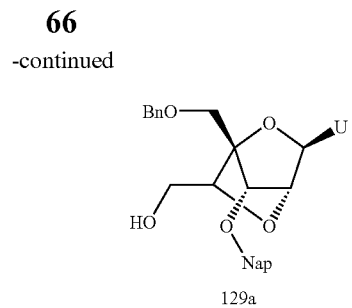

(a) Oxalyl Chloride, DMSO, Et$_3$N, CH$_2$Cl$_2$, -78 to 0° C.;
(b) Ph$_3$PCH$_2$Br, nBuLi, THF, -78° C. to rt, 97% from 26;
(c) TBAF, THF, rt, 16 h, 97%;
(d) NaH, BnBr, DMF, rt, 1 h quantitative;
(e) OsO$_4$, NMO, 95% aq. acetone, rt, 48 h, 87%;
(f) TBSCl, pyridine, 0° C., 4 h, quantitative;
(g) MsCl, Et$_3$N, DMAP, CH$_2$Cl$_2$, rt, 16 h, 44% and 40% recovered sm;
(h) Et$_3$N.3HF, Et$_3$N, THF, quantitative;
(i) PivCl, DIPEA, DMAP, CH$_2$Cl$_2$, rt, 16 h;
(j) AcOH, Ac$_2$O, catalytic H$_2$SO$_4$, 92% from 125;
(k) BSA, Uracil, TMSOTf, CH$_3$C, reflux 2 h;
(l) K$_2$CO$_3$, MeOH, 74% from 127.

A) Nucleoside 118

Dimethylsulfoxide (1.77 mL, 25.0 mmol) was added dropwise to a cold (-78° C.) solution of oxalyl chloride (1.10 mL, 12.5 mmol) in dichloromethane (60 mL). After stirring for 30 minutes, a solution of alcohol 26 (5.0 g, 8.4 mmol) in dichloromethane (20 mL) was added to the reaction. The stirring was continued at -78° C. for another 45 minutes after which, triethylamine (5.05 mL, 37.5 mmol) was added dropwise to the reaction. After stirring for 10 minutes, the ice bath was removed and the reaction was allowed to warm gradually to ca. 0° C. at which time, TLC analysis indicated no starting alcohol. The reaction was diluted with dichloromethane and the organic layer was sequentially washed with 10% HCl, saturated NaHCO$_3$, brine, dried (Na$_2$SO$_4$) and concentrate to provide aldehyde 27, which was used for the next step without any purification.

B) Nucleoside 118 nBuLi (2.5 M, 4.34 mL, 10.9 mmol) was added dropwise to a cold (0° C.) stirring solution of triphenylphosphonium bromide (3.88 g, 10.9 mmol) in dry THF (60 mL). After stirring for 1 hour, the red solution was cooled to -78° C. and a solution of aldehyde 27 from above (8.4 mmol) in dry THF (15 mL) was added dropwise to the reaction. The reaction was gradually allowed to warm to room temperature and the stirring was continued for another 16 hours. The reaction was then carefully quenched using saturated NH$_4$Cl and partitioned between EtOAc and water. The organic layer was sequentially washed with brine, dried (Na$_2$SO$_4$) and concentrated. Purification by column chromatography (SiO$_2$, eluting with 10% EtOAc in hexanes) provided olefin 118 (4.84 g, 97% from 26) as a colorless oil.

C) Nucleoside 119

Tetrabutylammonium fluoride (1M in THF, 10.00 mL, 10.0 mmol) was added to a solution of olefin 118 (4.83 g, 8.1 mmol) in THF (35 mL). The reaction was stirred at room temperature for 16 hours after which the solvent was removed under vacuum and the residue was dissolved in EtOAc. The organic layer was washed with water, brine, dried ($Na_2SO_4$) and concentrated. Purification by column chromatography ($SiO_2$, eluting with 40% EtOAc in hexanes) provided alcohol 119 (2.79 g, 97%) as a colorless oil.

D) Nucleoside 120

Sodium hydride (60% w/w in mineral oil, 0.4 g, 10 mmol) was added to a cold (0° C.) solution of alcohol 119 (1.44 g, 4.1 mmol) and benzyl bromide (0.71 mL, 6.0 mmol) in DMF (16 mL). After stirring for 1 hour at 0° C., the reaction was carefully quenched with water and partitioned between EtOAc and water. The organic layer was separated and washed with brine, dried ($Na_2SO_4$) and concentrated. Purification by column chromatography ($SiO_2$, eluting with 10 to 25% EtOAc in hexanes) provided olefin 120 (1.84 g, quantitative) as a colorless oil.

E) Nucleoside 121

Osmium Tetroxide ($OsO_4$, 25% solution in iPrOH, 1 mL) was added to a solution of olefin 120 (1.80 g, 4.0 mmol) and N-methylmorpholine-N-oxide (NMO, 0.94 g, 8.0 mmol) in 95% acetone/water (25 mL). After stirring for 16 h at room temperature, additional $OsO_4$ solution (0.5 mL) and NMO (0.40 g) were added to the reaction. After stirring for a total 48 hours, the reaction was diluted with EtOAc and washed with 10% $NaHSO_3$, brine, dried ($Na_2SO_4$) and concentrated. Purification by column chromatography ($SiO_2$, eluting with 40 to 50% EtOAc in hexanes) provided diol 121 (1.68 g, 87%, ca. 1:1 mixture of isomers) as a colorless oil.

F) Nucleosides 122 and 123

TBSCl (0.66 g, 4.4 mmol) was added to a cold (0° C.) solution of diol 121 (1.63 g, 3.4 mmol) in pyridine (17 mL). After stirring for 4 h at 0° C., the reaction was diluted with EtOAc and the organic layer was washed with water, brine, dried and concentrated. Purification by column chromatography ($SiO_2$, eluting with 10 to 20% EtOAc in hexanes) provided alcohols 122 and 123 (0.90 g and 1.17 g, absolute stereochemistry not assigned) as colorless oils.

G) Nucleoside 124

Methanesulfonyl chloride (0.24 mL, 3.0 mmol) was added dropwise to a cold (0° C.) solution of alcohol 123 (absolute stereochemistry not assigned, 0.9 g, 1.5 mmol), triethylamine (0.46 mL, 3.3 mmol) and dimethylaminopyridine (37 mg, 0.3 mmol) in dichloromethane (5 mL). After 7 hours at room temperature, additional methansulfonyl chloride (0.12 mL) and triethylamine (0.23 mL) were added to the reaction. After stirring for another 9 hours at room temperature, the reaction was poured into EtOAc and the organic layer was washed with 10% HCl, saturated $NaHCO_3$, brine, dried ($Na_2SO_4$) and concentrated. Purification by column chromatography ($SiO_2$, eluting with 10 to 15% EtOAc in hexanes) provided mesylate 124 (0.44 g, 44%) and starting diol 123 (0.32 g, 40%).

H) Nucleoside 125

Triethylamine trihydroflouride (0.64 mL, 4.0 mmol) was added to a solution of mesylate 124 (0.44 g, 0.6 mmol) and triethylamine (0.23 mL, 1.7 mmol) in THF (7 mL). After stirring for 16 hours at room temperature, the reaction was diluted with EtOAc and the organic phase was washed with saturated $NaHCO_3$, brine, dried ($Na_2SO_4$) and concentrated. Purification by column chromatography ($SiO_2$, eluting with 50% EtOAc in hexanes) provided alcohol 125 (0.40 g, quantitative).

I) Nucleoside 127

Pivaloyl chloride (0.12 mL, 1.0 mmol) was added dropwise to a cold (0° C.) solution of alcohol 125 (0.72 mmol, 0.4 g), diisopropylethylamine (DIPEA, 0.17 mL, 1.0 mmol) and dimethylaminopyridine (12 mg, 0.1 mmol) in dichloromethane (2 mL). The ice bath was then removed and the reaction was stirred at room temperature for 2 hours after which additional DIPEA (0.17 mL) and pivaloyl chloride (0.12 mL) was added and the reaction was stirred at room temperature for 16 hours. The reaction was then diluted with EtOAc and the organic layer was washed with 10% HCl, saturated $NaHCO_3$, brine, dried ($Na_2SO_4$) and concentrated to provide crude pivaloate 126, which was used without any further purification.

Concentrated sulfuric acid (2 drops) was added to a solution of crude pivaloate 126 (from above) in glacial acetic acid (2.5 mL) and acetic anhydride (0.5 mL). After stirring at room temperature for 2 hours, the solvent was removed under high vacuum and the residue was dissolved in EtOAc and the organic layer was washed with saturated $NaHCO_3$, brine, dried ($Na_2SO_4$) and concentrated. Purification by column chromatography ($SiO_2$, eluting with 10 to 15% EtOAc in hexanes) provided diacetate 127 (0.45 g, 92% from 125) as a colorless oil (mixture of anomers).

J) Nucleoside 129a

N,O-Bis(trimethylsilyl)acetamide (0.8 mL, 3.3 mmol) was added to a suspension of diacetate 127 (0.45 g, 0.65 mmol) and uracil (0.15 g, 1.3 mmol) in $CH_3CN$ (3.5 mL). After heating at 40° C. for 15 min to get a clear solution, trimethylsilyl triflate (0.24 mL, 1.3 mmol) was added to the reaction. After refluxing for 2 hours, the reaction was cooled to room temperature and poured into EtOAc. The organic layer was washed with saturated $NaHCO_3$, brine, dried ($Na_2SO_4$) and concentrated under vacuum to provide crude nucleoside 128a, which was used without any purification.

$K_2CO_3$ (40 mg, 0.3 mmol) was added to a solution of nucleoside 128a (0.11 g, 0.15 mmol) in MeOH (1.5 mL). After stirring for 16 h at room temperature, the solvent was removed under vacuum and the residue was partitioned between EtOAc and brine. The organic phase was collected, dried ($Na_2SO_4$) and concentrated under vacuum to provide 129a (absolute stereochemistry not determined). Purification by column chromatography ($SiO_2$, eluting with 35% acetone in $CHCl_3$) provided nucleoside 129a (57 mg, 74% from 127). $^1H$ NMR ($CDCl_3$): δ 9.37 (s, 1H), 7.92-7.61 (m, 5H), 7.55-7.23 (m, 9H), 5.58 (s, 1H), 5.43 (d, 1H, J=8.1), 4.79 (d, 1H, J=11.7), 4.66 (d, 1H, J=11.7), 4.58 (m, 2H), 4.51 (s, 1H), 4.44 (m, 1H), 4.05 (s, 1H), 3.95-3.72 (m, 4H). LCMS: retention time 3.34 min; M+H calcd. 517.19, found 517.1.

Example 18

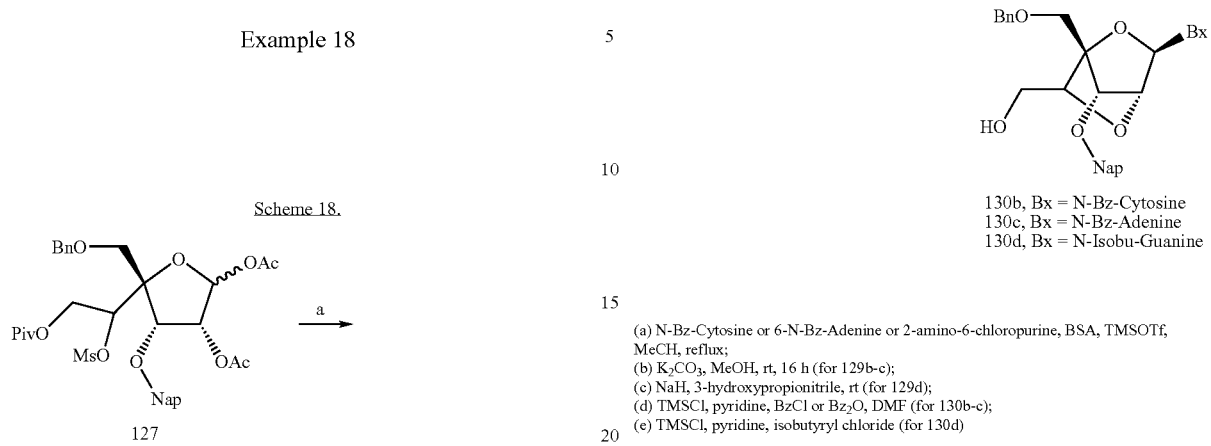

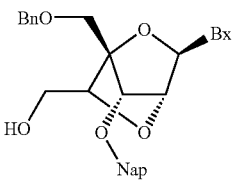

130b, Bx = N-Bz-Cytosine
130c, Bx = N-Bz-Adenine
130d, Bx = N-Isobu-Guanine (a) N-Bz-Cytosine or 6-N-Bz-Adenine or 2-amino-6-chloropurine, BSA, TMSOTf, MeCH, reflux;
(b) K$_2$CO$_3$, MeOH, rt, 16 h (for 129b-c);
(c) NaH, 3-hydroxypropionitrile, rt (for 129d);
(d) TMSCl, pyridine, BzCl or Bz$_2$O, DMF (for 130b-c);
(e) TMSCl, pyridine, isobutyryl chloride (for 130d)

Nucleosides 128b, 128c and 128d are prepared from sugar precursor 127 by a Vorbrugen reaction using N-Bz-cytosine, 6-N-Bz-adenine and 2-amino-6-chloropurine respectively (Scheme 18). Treatment of 128b and 128c with K$_2$CO$_3$ and MeOH provides nucleosides 129b and 129c respectively. Treatment of 128d with sodium hydride and 3-hydroxypropionitrile provides nucleoside 129d. Transient protection of the hydroxyl group with TMSCl followed by reaction with benzoyl chloride provides nucleosides 130b and 130c respectively. Alternatively the above transformation can also be accomplished by reacting nucleosides 129b and 129c with benzoic anhydride using DMF as the solvent. Nucleoside 130d is prepared by transient protection with excess TMSCl in pyridine followed by reaction with isobutyryl chloride.

Example 19

Preparation of 6'-Substituted Analogs

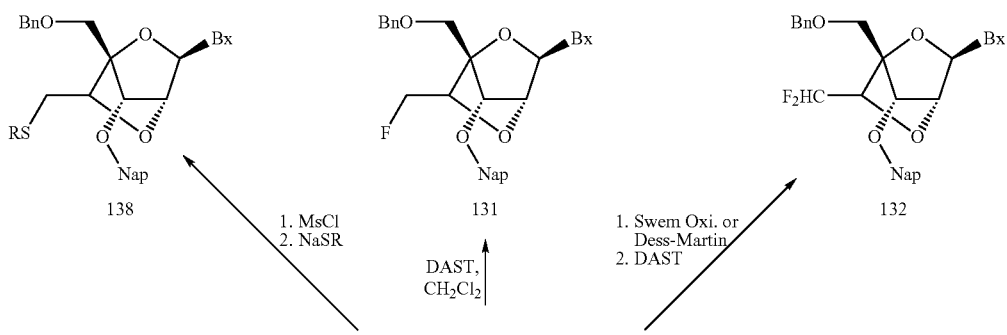

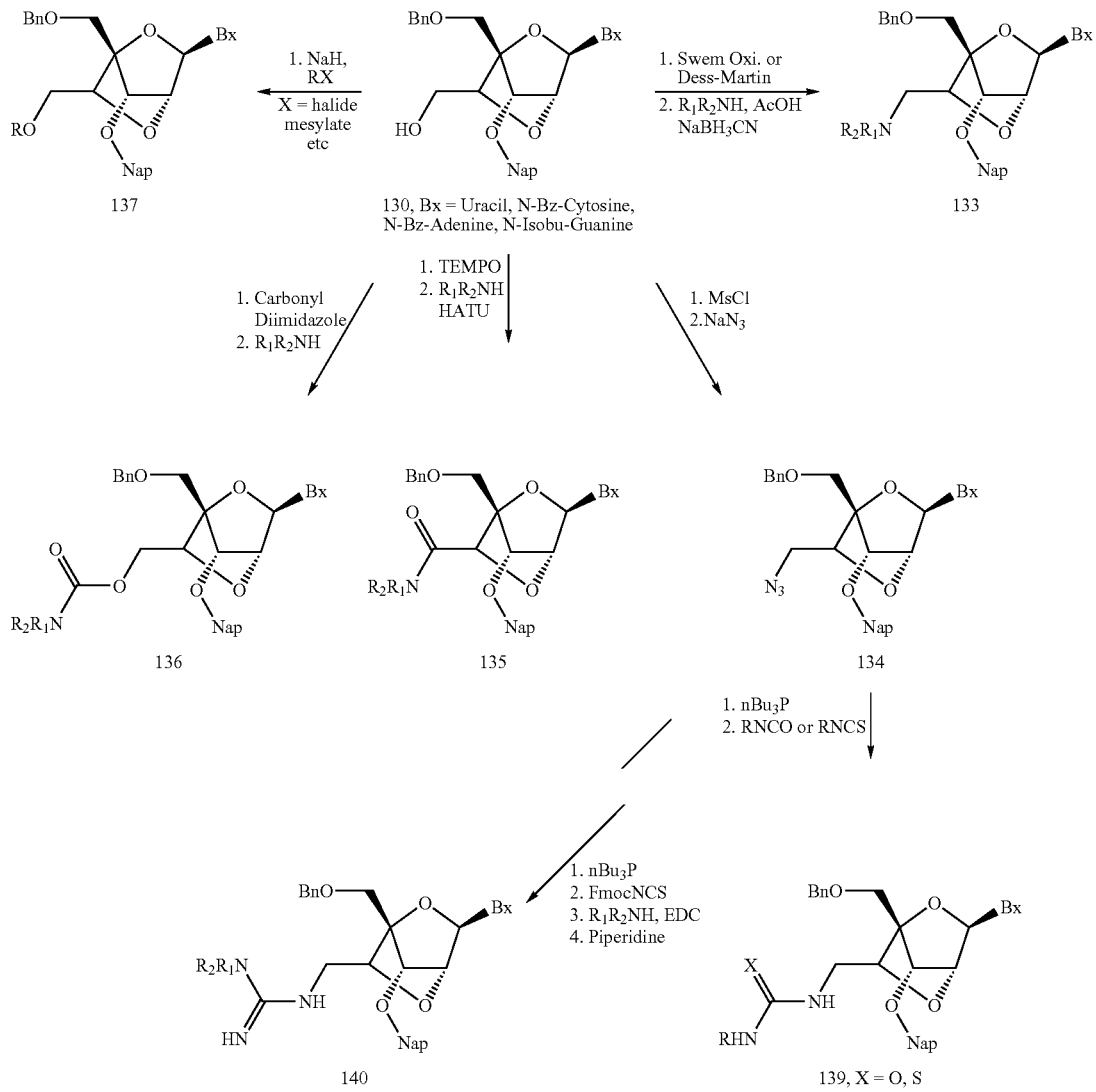

R, $R_1$ and $R_2$ are each independently H, alkyl, alkenyl, alkynyl, substituted alkyl, substituted alkenyl, substituted alkynyl, or a protecting group Nucleoside 131 is prepared from nucleoside 130 by treatment with a fluorinating agent such as DAST using dichloromethane as the solvent. Nucleoside 132 is prepared from 130 by first oxidizing the primary hydroxyl group with Dess-Martin periodinane or under Swern conditions followed by treatment of the resulting aldehyde with DAST. Nucleoside 133 is prepared from 130 by first oxidizing the primary hydroxyl group with Dess-Martin periodinane or under Swern conditions followed by reductive amination of the resulting aldehyde with a primary or a secondary amine in the presence of glacial acetic acid and a reducing agent such as sodium cyanoborohydride. Nucleoside 134 is prepared from 130 by converting the hydroxyl group to a leaving group (mesylate, tosylate, halide) followed by heating with excess sodium azide. Nucleoside 135 is prepared from 130 by oxidation of the primary alcohol to a carboxylic acid followed by reaction with a amine in the presence of HATU or any other peptide coupling reagent. Nucleoside 136 is prepared from 130 by activating the hydroxyl group with carbonyl dimimdazole followed by reaction with a amine. Nucleoside 137 is prepared from 130 by deprotonating the hydroxyl group with an appropriate base followed by quenching the anion with an alkylating reagent. Nucleoside 138 is prepared from 130 by converting the hydroxyl group to a leaving group followed by displacement with a thiol nucleophile. Nucleoside 139 is prepared from 134 by reduction of the azide group followed by reaction with an isocyanate or an isothiocyanate. Nucleoside 140 is prepared from 134 by reduction of the azido group and reaction with FmocNCS to provide an activated thiourea. Further reaction of the fmoc activated thiourea with an amine in the presence of EDC provides the substituted guanidine. Removal of the fmoc protecting group liberates nucleoside 140.

Example 20

Preparation of 6-Substituted BNA Phosphoramidite Nucleosides

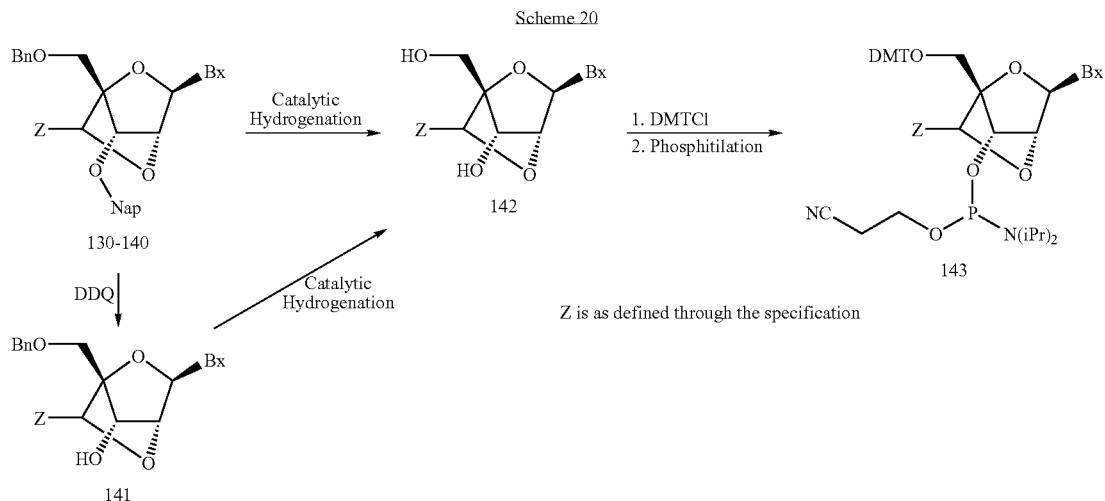

Scheme 20

Z is as defined through the specification

Nucleoside 142 is prepared from nucleoside 130-140 by catalytic hydrogenation to remove the 3'- and 5'-O protecting groups. Alternatively, 142 can be prepared from 130-140 by first removing the 3'O-Nap group with DDQ followed by a catalytic hydrogenation to remove the 5'O-benzyl group. Subsequent protection of the 5' hydroxyl group as the dimethoxytrityl ether followed by a phosphitilation reaction provides phosphoramidite 143.

Example 21

Preparation of 6-CH₂F Nucleoside

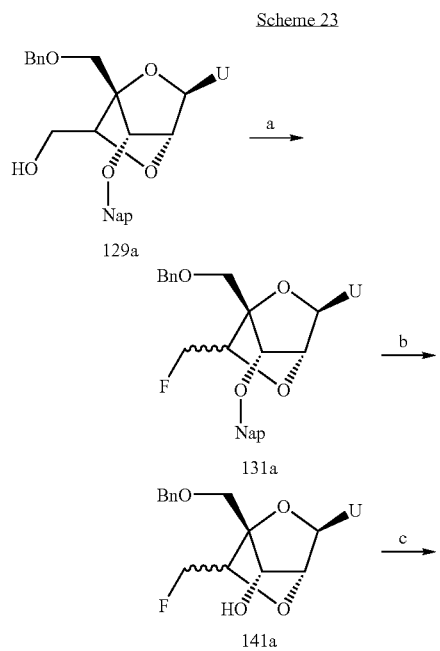

Scheme 23

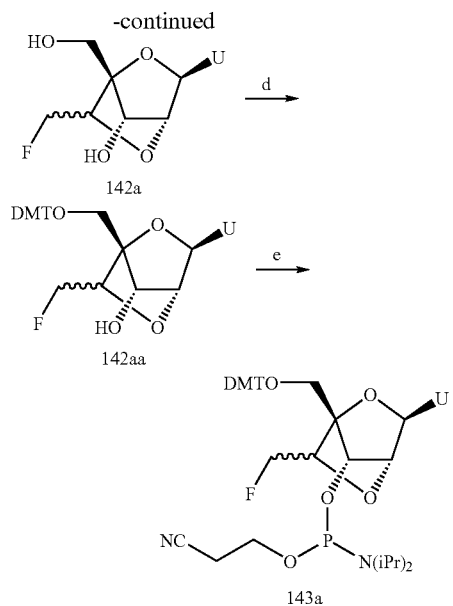

(a) DAST, CH$_2$Cl$_2$, -78° C. to rt, 16 h, 52%
(b) DDQ CH$_2$Cl$_2$, H$_2$O, rt, 8 h, quant.
(c) 10% Pd/C, H$_2$ balloon, 50%
(d) DMTCl, pyridine, 55%
(e) (iPr$_2$)$_2$NPOCH$_2$CH$_2$CN, tetrazole, NMI, DMF

A) Nucleoside (131a)

Diethylaminosulfurtrifluoride (DAST, 0.16 mL, 1.4 mmol) was added to a cold (−50° C.) solution of nucleoside 129a (0.1 g, 0.2 mmol) in dichloromethane (2 mL). The reaction was gradually warmed to room temperature and stirred 16 hours after which, it was carefully quenched with saturated NaHCO$_3$ solution. The reaction was then partitioned between EtOAc and brine, dried (Na$_2$SO$_4$) and concentrated. Purification by column chromatography (SiO$_2$, 33% EtOAc in hexanes) provided nucleoside 131a (51 mg, 52%, contaminated with 15-20% of a ring opened impurity) as a mixture of isomers). $^{19}$F NMR (CDCl$_3$): δ –227.98 (m) and –231.07 (m). LCMS: retention time 3.84 min; M+H calcd. 519.19, found 519.1 and 3.89 min; M+H calcd. 519.19, found 519.1.

B) Nucleoside (141a)

DDQ (44 mg, 0.2 mmol) was added to a solution of nucleoside 131a (51 mg, 0.1 mmol) in dichloromethane (1 mL) and water (2 drops). After stirring at room temperature for 8 hours, the reaction was diluted with EtOAc and the organic phase was washed with 10% NaHSO$_3$ solution, saturated NaHCO$_3$ solution, brine, dried (Na$_2$SO$_4$) and concentrated. Purification by column chromatography (SiO$_2$, 30% acetone in chloroform) provided nucleoside 141a (41 mg, quantitative as a mixture of isomers). $^{19}$F NMR (CDCl$_3$): δ –229.3 (t) and –230.97 (dt). LCMS: retention time 2.66 min; M+H calcd. 379.12, found 379.0

C) Nucleoside (142a)

A mixture of nucleoside 141a (41 mg, from above) and 10% palladium on charcoal (10 mg) in methanol (2 mL) was hydrogenated using a hydrogen balloon. After 3 hours, all starting nucleoside 141a was consumed (as indicated by LCMS analysis of the reaction mixture). The reaction was filtered through celite and the filtrate concentrated under reduced pressure. Purification by column chromatography (SiO$_2$, 10 to 20% methanol in chloroform) provided nucleoside 142a (14 mg, 50%) as a mixture of isomers. $^{19}$F NMR (CDCl$_3$): δ –231.45 (t) and –232.88 (dt). LCMS: retention time 1.72 min; M+Na calcd. 311.08, found 311.0.

D) Nucleoside (142aa)

DMTCl (24 mg, 0.07 mmol) was added to a solution of nucleoside 142a (14 mg, 0.049 mmol) in pyridine (0.25 mL). After stirring at room temperature for 3 hours, the reaction was concentrated under reduced pressure. Purification by column chromatography (SiO$_2$, 20 to 30% acetone in chloroform) provided nucleoside 142aa (16 mg, 55%) as a mixture of isomers. $^{19}$F NMR (CDCl$_3$): δ –228.6 (t) and –230.91 (dt). LCMS: retention time 3.56 min; M+Na calcd. 613.21, found 613.1.

E) Amidite (143a)

Amidite 143a is prepared from nucleoside 142aa using a phosphitilation reaction as described in example 1.

Example 22

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 23

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH$_4$OAc solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleo-sides, as well as mixed backbone oligomeric compounds having, for instance, alternating MMI and P=O or P=S linkages can be prepared as described in U.S. Pat. Nos. 5,378,825; 5,386,023; 5,489,677; 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Example 24

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

Example 25

Oligonucleotide Synthesis—96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 26

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 27

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTINT™

When cells reached 65-75% confluency, they are treated with oligonucleotide. Oligonucleotide is mixed with LIPOFECTINT™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTINT™, LIPOFECTAMINE™, OLIGOFECTAMINE™, and FUGENE™. Other suitable transfection methods known in the art include, but are not limited to, electroporation.

Example 28

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of Monoclonal Antibodies is Taught in, for Example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 29

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 30

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µl, of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 31

Real-Time Quantitative PCR Analysis of Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 μL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Example 32

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
AATGGCTAAGTGAAGATGACAATCAT      (SEQ ID NO: 2)

Reverse primer:
TGCACATATCATTACACCAGTTCGT       (SEQ ID NO: 3)
```

And the PCR probe:

```
                                           (SEQ ID NO: 4)
    FAM-TTGCAGCAATTCACTGTAAAGCTGGAAAGG-TAMRA,
``` where FAM is the fluorescent dye and TAMRA is the quencher dye.

Example 33

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 34

6-(R or S)—$CH_3$ and 6-(R or S)—$CH_2$—O—$CH_3$ BNA 2-10-2 Gapped Oligomers Targeted to PTEN: In Vitro Study In accordance with the present invention, oligomeric compounds were synthesized and tested for their ability to reduce PTEN expression over a range of doses. b.END cells were treated with the 6-(R or S)—$CH_3$—BNA (392748 and 392749 respectively) and 6-(R or S)—$CH_2$—O—$CH_3$ (396004 and 396005 respectively) modified oligomers at concentrations of 0.3125, 0.0625, 1.25, 2.5, 5, 10 or 20 nM using methods described herein. Expression levels of PTEN were determined using real-time PCR and normalized to RIBOGREEN™ as described in other examples herein. Resulting dose-response curves were used to determine the EC50 as shown below. Tm's were assessed in 100 mM phosphate buffer, 0.1 mM EDTA, pH 7, at 260 nm using 4 µM 6-(R or S)—$CH_3$—BNA or 6-(R or S)—$CH_2$—O—$CH_3$ modified oligomers and 4 µM complementary RNA.

| SEQ ID NO./ ISIS NO. | Composition (5' to 3') | $EC_{50}$ | Tm °C. |
|---|---|---|---|
| 05/392748 | $C_RU_R$TAGCACTGGC $C_RU_R$ | 10.3 | 58.9 |
| 05/392749 | $C_sU_s$TAGCACTGGC $C_sU_s$ | 6.4 | 59.1 |
| 05/396004 | <u>$C_sU_s$</u>TAGCACTGGC<u>$C_sU_s$</u> | 6.0 | 56.9 |
| 05/396005 | <u>$C_sU_s$</u>TAGCACTGGC<u>$C_sU_s$</u> | 5.0 | 57.6 |
| 05/392745 | $C_lU_l$TAGCACTGGC $C_lU_l$ | 7.5 | 58.6 |

All internucleoside linkages are phosphorothioate, bolded nucleosides are 6-(R or S)—$CH_3$ BNA nucleosides, underlined and bolded nucleosides are 6-(R or S)—$CH_2$—O—$CH_3$ BNA nucleosides and subscripts R and S indicate the configuration at the 6 carbon atom. It is notable that the 6-modified BNA oligomeric compounds exhibited greater potency despite the slight decrease in Tm.

Example 35

6-(S)—$CH_3$—BNA and 6-(R)—$CH_3$—BNA 2-10-2 Gapped Oligomers Targeted to PTEN: In Vivo Study Six week old Balb/c mice (Jackson Laboratory, Bar Harbor, Me.) were injected twice weekly for 3 weeks with a 6-$CH_3$—BNA modified oligomers (either 6-(S) or 6-(R)) targeted to PTEN at a dose of 0.5 or 2 µmol/kg. The mice were sacrificed 48 hours following the final administration. Liver tissues were homogenized and mRNA levels were quantitated using real-time PCR as described herein for comparison to untreated control levels (% UTC).

| SEQ ID NO./ ISIS NO. | Composition (5' to 3') | dose (µmol/kg) | % UTC |
|---|---|---|---|
| saline | | | 100 |
| 05/392748 | $C_RU_R$TAGCACTGGC $C_RU_R$ | 2.0 | 31 |
| 05/392748 | $C_RU_R$TAGCACTGGC $C_RU_R$ | 0.5 | 81 |
| 05/392749 | $C_sU_s$TAGCACTGGC $C_sU_s$ | 2.0 | 23 |
| 05/392749 | $C_sU_s$TAGCACTGGC $C_sU_s$ | 0.5 | 73 |

All internucleoside linkages are phosphorothioate, bolded nucleosides are 6-$CH_3$—BNA nucleosides and subscripts R and S indicate the configuration at the 6 carbon atom.

Example 36

6-(S)—$CH_3$—BNA and 6-(R)—$CH_3$—BNA 2-10-2 Gapped Oligomers Targeted to PTEN: In Vivo Study Six week old Balb/c mice (Jackson Laboratory, Bar Harbor, Me.) were injected once with 6-$CH_3$—BNA modified oligomers (either 6-(S) or 6-(R)) targeted to PTEN at a dose of 1, 2, 4 or 8 µmol/kg. The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | dose (µmol/kg) | % UTC |
|---|---|---|---|
| saline | | | 100 |
| 05/392748 | $C_RU_R$TAGCACTGGC $C_RU_R$ | 1 | 89 |
| 05/392748 | $C_RU_R$TAGCACTGGC $C_RU_R$ | 2 | 66 |
| 05/392748 | $C_RU_R$TAGCACTGGC $C_RU_R$ | 4 | 35 |
| 05/392748 | $C_RU_R$TAGCACTGGC $C_RU_R$ | 8 | 11 |
| 05/392749 | $C_sU_s$TAGCACTGGC $C_sU_s$ | 1 | 75 |
| 05/392749 | $C_sU_s$TAGCACTGGC $C_sU_s$ | 2 | 51 |
| 05/392749 | $C_sU_s$TAGCACTGGC $C_sU_s$ | 4 | 25 |
| 09/392749 | $C_sU_s$TAGCACTGGC $C_sU_s$ | 8 | 9 |

All internucleoside linkages are phosphorothioate, bolded nucleosides are 6-$CH_3$—BNA nucleosides and subscripts S and R indicate the configuration at the 6 carbon atom.

Example 37

6-(S)—$CH_3$—O—$CH_2$—BNA and 6-(R)—$CH_3$—O—$CH_2$—BNA 2-10-2 Gapped Oligomers Targeted to PTEN: In Vivo Study Six week old Balb/c mice (Jackson Laboratory, Bar Harbor, Me.) were injected once with 6-$CH_3$—BNA modified oligomers (either 6-(S) or 6-(R)) targeted to PTEN at a dose of 1, 2, 4 or 8 µmol/kg (only the 8 µmol/kg data is shown below). The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | dose (µmol/kg) | % UTC |
|---|---|---|---|
| saline | | | 100 |
| 05/396004 | C<sub>R</sub>U<sub>R</sub>TAGCACTGGC C<sub>R</sub>U<sub>R</sub> | 8 | 37 |
| 05/396005 | C<sub>S</sub>U<sub>S</sub>TAGCACTGGC C<sub>S</sub>U<sub>S</sub> | 8 | 37 |

All internucleoside linkages are phosphorothioate, bolded and underlined nucleosides are 6-$CH_3$—O—$CH_2$—BNA nucleosides and subscripts S and R indicate the configuration at the 6 carbon atom.

Example 38

Nuclease Stability of 6-(R or S)—$CH_3$—BNA Modified Oligomers Treated with SVPD The nuclease stability of 6-(R or S)—$CH_3$—BNA (392748 and 392749 respectively) modified oligomers was determined using snake venom phosphodiesterase (SVPD). The study included a the respective 6-unsubstituted gapmer (4'-$CH_2$—O-2' bridged BNA, 392745, subscript 1) and the 2'-O-MOE gapmer (2'-O—$(CH_2)_2$—$OCH_3$, 392753, subscript e) for comparison. Each oligomer is prepared as a 500 µL mixture containing: 5 µL 100 µM oligomer, 50 µL phosphodiesterase I @ 0.5 Units/mL in SVPD buffer (50 mM Tris-HcL, pH 7.5, 8 mM $MgCl_2$) final concentration 0.05 Units/mL, 445 µL SVP buffer. Samples were incubated at 37° C. in a water bath. Aliquats (100 µL) were taken at 0, 1, 2 and 4 days with fresh enzyme added at days 1 and 2. EDTA was added to aliquats immediately after removal to quench enzyme activity. Samples were analized on IP HPLC/MS.

| SEQ ID NO./ ISIS NO. | Composition (5' to 3') | % full length at day 4 |
|---|---|---|
| 05/392748 | C<sub>R</sub>U<sub>R</sub>TAGCACTGGC C<sub>R</sub>U<sub>R</sub> | >90 |
| 05/392749 | C<sub>S</sub>U<sub>S</sub>TAGCACTGGC C<sub>S</sub>U<sub>S</sub> | >70 |
| 05/392745 | C<sub>l</sub>U<sub>l</sub>TAGCACTGGC C<sub>l</sub>U<sub>l</sub> | >40 |
| 05/392753 | C<sub>e</sub>U<sub>e</sub>TAGCACTGGC C<sub>e</sub>U<sub>e</sub> | >30 |

| SEQ ID NO./ ISIS NO. | % Composition at 24 hours | % Composition at 48 hours | % Composition at 96 hours |
|---|---|---|---|
| 05/392748 | 100% | 89% | 92% |
| 05/392749 | 96% | 84% | 74% |
| 05/392745 | 67% | 56% | 48% |
| 05/392753 | 58% | 46% | 36% |

All internucleoside linkages are phosphorothioate, bolded nucleosides are modified nucleosides, subscript R and S indicate the configuration at the 6 carbon atom for 6-$CH_3$—BNA nucleosides, subscript e indicates 2'-O-MOE nucleosides and subscript 1 indicates 4'-$CH_2$—O-2' modified nucleosides. The 6-methyl substituted BNA-containing compounds (392748 and 392749) had a marked improvement over the unsubstituted BNA-containing compound (392745).

Example 39

Nuclease Stability of 6-(R or S)—$CH_3$—BNA, 4'-$CH_2$—O-2' BNA and 2'-O-MOE Modified Oligomers Treated with SVPD The nuclease stability of 6-$CH_3$—BNA modified oligomers was determined using snake venom phosphodiesterase (SVPD). Each oligomer is prepared as a 90 µL mixture containing 5 µL oligomer (2 µL of 5 µM oligomer and 3 µL of 5' $^{32}$P-labeled oligomer) 75 µL $H_2O$, and 10 µL 10× buffer (500 mM Tris-HCl, 700 mM NaCl, and 140 mM $MgCl_2$ at pH 8.6). At time equals 0 min, 9 µL were removed from the oligomer sample prepared above and added to 10 µL stop buffer (6.67 M urea, 16.67% formamide and 83.3 mM EDTA) followed by 1 µL of $H_2O$ and heated at 100° C. for 2.5 to 3 min. The kinetics of the assay began by the addition of 9 µL of SVPD (0.5 Units/mL). Final enzyme concentration was 0.05 Units/mL. Each aliquot of 10 µL of oligomer kinetics solution were added to 10 µL of stop buffer and heat deactivated as described above. Kinetic time points were taken at 1, 3, 9, 27, 80, 240 and 1290 min. Samples were analyzed by 12% acrylomide PAGE run for 2 hours at 45 Watts/gel.

| SEQ ID NO./ ISIS NO. | Composition (5' to 3') | modification |
|---|---|---|
| 06/395421 | TTTTTTTTTT T<sub>e</sub>T<sub>e</sub> | Bold 2'-O-MOE |
| 07/395423 | TTTTTTTTTT U<sub>I</sub>U<sub>I</sub> | Bold 4'-$CH_2$-O-2' |
| 07/395424 | TTTTTTTTTT U<sub>R</sub>U<sub>R</sub> | Bold 6-(R)-$CH_3$ |
| 07/395425 | TTTTTTTTTT U<sub>S</sub>U<sub>S</sub> | Bold 6-(S)-CH |
| 06/7157 | TTTTTTTTTTTT | unmodified (2'-H) |

All internucleoside linkages are phosphorothioate, bolded nucleosides are modified nucleosides, subscript R and S indicate the configuration at the 6 carbon atom for 6-$CH_3$—BNA nucleosides, subscript e indicates 2'-O-MOE nucleosides and subscript 1 indicates 4'-$CH_2$—O-2' modified nucleosides.

| SEQ ID NO. ISIS No. | % Comp. at 3 min. | % Comp. at 27 min. | % Comp. at 80 min. | % Comp. at 240 min. | % Comp. at 1290 min. |
|---|---|---|---|---|---|
| 06/395421 | 68.7 | 27.9 | 17.2 | 11.6 | 9.0 |
| 07/395423 | 32.6 | 4.7 | 2.5 | 2.2 | 2.2 |
| 07/395424 | 96.4 | 89.1 | 83.2 | 79.0 | 72.0 |
| 07/395425 | 96.0 | 86.3 | 83.7 | 82.3 | 82.7 |
| 06/7157 | 5.2 | 1.2 | 2.0 | 1.7 | 0.9. |

Example 40

6-(S)—$CH_3$—BNA, 4'-$CH_2$—O-2-BNA, and 2'-O-MOE Gapped Oligomers Targeted to PTEN in a Three-Week, Multiple Dose In Vivo Study Six week old Balb/c mice (Jackson Laboratory, Bar Harbor, Me.) were injected twice weekly for three weeks with 6-(S)—CH$_3$—BNA (2-10-2,14-mer), 4'-CH$_2$—O-2'-BNA (2-10-2,14-mer) and 2'-O-MOE (5-10-5,20-mer) modified oligomers targeted to PTEN at a dose of 3.2, 1.0, 0.32 and 0.1 μmol/kg (only the 3.2 and 1 μmol/kg data is shown below). The mice were sacrificed 48 hrs following last administration. Liver tissues were homogenized and mRNA levels were quantitated using real-time PCR as described herein for comparison to untreated control levels (% UTC). Plasma chemistries and liver weights were determined after sacrifice.

| SEQ ID NO./ ISIS NO. | Composition (5' to 3') | dose (μmol/kg) | % UTC | ALT |
|---|---|---|---|---|
| saline | | | 100 | 41.3 |
| 05/392749 | C$_s$U$_s$TAGCACTGGCC$_s$U$_s$ | 3.2 | 4.3 | 29.8 |
| 05/392749 | C$_s$U$_s$TAGCACTGGCC$_s$U$_s$ | 1 | 36 | 24.5 |
| 05/392063 | C$_I$U$_I$TAGCACTGGCC$_I$U$_I$ | 3.2 | 4.2 | 279.3 |
| 08/392063 | $^{Me}$C$_I$T$_I$TAGCACTGGC$^{Me}$C$_I$T$_I$ | 1 | 26 | 41.0 |
| 09/116847 | C$_e$T$_e$G$_e$C$_e$T$_e$AGCCTCTGGAT$_e$T$_e$T$_e$G$_e$A$_e$ | 1 | 53 | 41.3 |

All internucleoside linkages are phosphorothioate, bolded nucleosides are modified positions, subscript s indicates 6-(S)—CH$_3$—BNA, subscript 1 indicates a 4'-CH$_2$—O-2' BNA, subscript e indicates a 2'-O-MOE and $^{Me}$C indicates a 5'-methyl cytosine nucleoside.

At the culmination of the study, animals in the high dose group showed significant increase in liver weights for the 4'-CH$_2$—O-2' BNA (392063, 3.2 μmol/Kg dose group) containing oligomers (153% relative to saline). In contrast, the liver weights for 6-(S)—CH$_3$ BNA (392749, 3.2 μmol/Kg dose group) containing oligomers were 117% relative to saline. Liver weights for 2'O-MOE containing oligomers (116847, 1.0 μmol/Kg dose group) were 116% relative to saline. This example demonstrates that the 6-(S)—CH$_3$—BNA modification allows for the design of antisense oligomers which maintain the potency conferred by the 4'-CH$_2$—O-2' BNA with a dramatic improvement in the ALT levels over the 4'-CH$_2$—O-2' BNA modified compounds.

Example 41

6-(R or S)—CH$_3$, 6-(R or S)—CH$_2$—OCH$_3$, 4'-CH$_2$—O-2' BNA 2-10-2 Gapped Oligomers Targeted to PTEN: In Vivo Study Six week old Balb/c mice (Jackson Laboratory, Bar Harbor, Me.) were injected once with modified 6-(R or S)—CH$_3$ (396568 and 396024 respectively), 6-(R or S)—CH$_2$—OCH$_3$ (396007 and 396008 respectively), 4'-CH$_2$—O-2' BNA 2-10-2 gapped oligomers targeted to PTEN at a dose of 2.5, 5, 10 and 20 μmol/kg (only 5 and 10 μmol/Kg data shown). The mice were sacrificed 66 hrs following administration. Liver tissues were homogenized.

| SEQ ID NO./ ISIS NO. | Composition (5' to 3') | dose (μmol/kg) | ALT |
|---|---|---|---|
| saline | | | 41.3 |
| 05/396024 | C$_s$U$_s$TAGCACTGGCC$_s$U$_s$ | 10 | 250.5 |
| 05/396024 | C$_s$U$_s$TAGCACTGGCC$_s$U$_s$ | 5 | 72.0 |
| 05/396568 | C$_R$U$_R$TAGCACTGGCC$_R$U$_R$ | 10 | 234.3 |
| 05/396568 | C$_R$U$_R$TAGCACTGGCC$_R$U$_R$ | 5 | 62.0 |
| 05/396008 | C$_s$U$_s$TAGCACTGGCC$_s$U$_s$ | 10 | 129.5 |
| 05/396008 | C$_s$U$_s$TAGCACTGGCC$_s$U$_s$ | 5 | 49.0 |
| 05/396007 | C$_R$U$_R$TAGCACTGGCC$_R$U$_R$ | 10 | 49.0 |
| 05/396007 | C$_R$U$_R$TAGCACTGGCC$_R$U$_R$ | 5 | 36.3 |
| 08/392063 | $^{Me}$C$_I$T$_I$TAGCACTGGC$^{Me}$C$_I$T$_I$ | 10 | 925.0 |
| 08/392063 | $^{Me}$C$_I$T$_I$TAGCACTGGC$^{Me}$C$_I$T$_I$ | 5 | 373.0 |

All internucleoside linkages are phosphorothioate, bolded nucleosides are modified nucleosides, subscript R and S indicate the configuration at the 6 carbon atom for 6-CH$_3$—BNA (bolded only) and 6-CH$_2$—O—CH$_3$—BNA (bolded an underlined) nucleosides as indicated, subscript 1 indicates 4'-CH$_2$—O-2' nucleosides and $^{Me}$C indicates a 5'-methyl cytosine nucleoside.

For the above oligonucleosides, one (Isis No. 392063) does not include a nucleoside that is chiral at the 6 carbon atom, wherein the other four (Isis Nos. 396024, 396568, 396008 and 396007) do. Specifically, those four include one such nucleoside at the 1, 2, 13 and 14 positions. The one that does not has a relatively higher toxicity in the liver compared to the four oligonucleosides that do.

Example 42

2-14-2 Gapped Oligomers Targeted to PTEN: In Vivo Study

Six week old Balb/c mice (Jackson Laboratory, Bar Harbor, Me.) were injected once with 6-CH$_3$—BNA modified oligomers targeted to PTEN at a dose of 2 or 10 μmol/kg. The mice were sacrificed 72 hrs following administration. Liver tissues were homogenized and mRNA levels were quantitated using real-time PCR as described herein for comparison to untreated control levels (% UTC).

| SEQ ID NO./ ISIS NO. | Composition (5' to 3') | modification |
|---|---|---|
| 10/394420 | $^m$C$_e$T$_e$GCTAGCCTCTGGATT$_e$T$_e$ | Bold 2'-O-MOE |
| 11/400522 | $^m$C$_R$U$_R$GCTAGCCTCTGGATU$_R$U$_R$ | Bold 6-(R)—CH$_3$ |
| 11/400523 | $^m$C$_S$U$_S$GCTAGCCTCTGGATU$_S$U$_S$ | Bold 6-(S)—CH$_3$ |
| 11/400524 | $^m$C$_R$U$_R$GCTAGCCTCTGGATU$_R$U$_R$ | Bold 6-(R)—CH$_2$—O—CH$_3$ |
| 11/400525 | $^m$C$_S$U$_S$GCTAGCCTCTGGATU$_S$U$_S$ | Bold 6-(S)—CH$_2$—O—CH$_3$ |

| ISIS NO. | dose (μmol/kg) | % UTC | Standard deviation |
|---|---|---|---|
| saline | | 100% | 12% |
| 394420 | 2 | 79% | 2% |
| 394420 | 10 | 26% | 11% |
| 400522 | 2 | 18% | 3% |
| 400522 | 10 | 4% | 0% |
| 400523 | 2 | 17% | 2% |
| 400523 | 10 | 4% | 1% |
| 400524 | 2 | 23% | 7% |
| 400524 | 10 | 4% | 0% |
| 400525 | 2 | 21% | 3% |
| 400525 | 10 | 3% | 0% |

All internucleoside linkages are phosphorothioate, bolded nucleosides are modified nucleosides, subscript R and S indicate the configuration at the 6 carbon atom for 6-CH$_3$—BNA and 6-CH$_2$—O—CH$_3$—BNA nucleosides as indicated, subscript e indicates 2'-O-MOE nucleosides and $^{Me}$C indicates a 5'-methyl cytosine nucleoside.

All publications, patents, and patent applications referenced herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An oligomeric compound comprising at least one monomer having Formula IX:

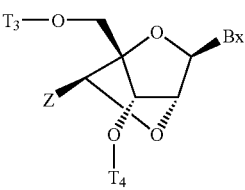

IX wherein independently for each of said monomers having Formula IX:
- Bx is a heterocyclic base moiety;
- $T_3$ and $T_4$ are each, independently, an internucleoside linking group linking the monomer to the oligomeric compound or one of $T_3$ and $T_4$ is an internucleoside linking group linking the monomer to the oligomeric compound and the other of $T_3$ and $T_4$ is H, a hydroxyl protecting group or a linked conjugate group;
- Z is $C_1$-$C_6$ alkyl or substituted $C_1$-$C_6$ alkyl;
- each substituted group is, independently, mono or poly substituted with optionally protected substituent groups independently selected from fluoro, $OJ_1$, $NJ_1J_2$, $SJ_1$ and CN, wherein each $J_1$ and $J_2$ is, independently, H, $C_1$-$C_6$ alkyl or a protecting group; and
- wherein said oligomeric compound comprises from about 8 to about 40 nucleosides and/or modified nucleosides or mimetics in length.

2. The oligomeric compound of claim 1 wherein each Z is methyl.

3. The oligomeric compound of claim 1 wherein each Z is $CH_2OCH_3$.

4. The oligomeric compound of claim 1 wherein each Z is $CH_2F$, $CHF_2$ or $CF_3$.

5. The oligomeric compound of claim 1 including at least one modified nucleoside wherein each modified nucleoside independently comprises a modified sugar moiety selected from a 4'-S modified sugar, a bicyclic modified sugar or a substituted sugar.

6. The oligomeric compound of claim 5 wherein each modified nucleoside comprises a modified sugar moiety independently selected from a 2'-F, 2'-$OCH_3$, 2'-O—$(CH_2)_2$—$OCH_3$ or a 2'-O—$CH_2$-4' modified sugar moiety.

7. The oligomeric compound of claim 1 comprising from about 8 to about 20 nucleosides and/or modified nucleosides or mimetics in length.

8. The oligomeric compound of claim 1 wherein essentially each internucleoside linkage is a phosphorothioate internucleoside linkage.

9. The oligomeric compound of claim 1 wherein essentially each internucleoside linkage is a phosphodiester internucleoside linkage.

10. An oligomeric compound having the formula:

$$G\text{-}[T\text{-}L]_j\text{-}[R\text{-}L]_q\text{-}R\text{-}[L\text{-}T]_r\text{-}E \qquad \text{III}$$

wherein:
- each R is a β-D-2'-deoxyribonucleoside;
- each L is, independently, a phosphodiester or phosphorothioate internucleoside linking group;
- G and E are each, independently, H, a hydroxyl protecting group or a linked conjugate group;
- each T is a monomer of the Formula VIII:

VIII wherein independently for each monomer having Formula VIII:
- Bx is a heterocyclic base moiety;
- Z is $C_1$-$C_6$ alkyl or substituted $C_1$-$C_6$ alkyl;
- each substituted group is, independently, mono or poly substituted with optionally protected substituent groups independently selected from fluoro, $OJ_1$, $NJ_1J_2$, $SJ_1$ and CN, wherein each $J_1$ and $J_2$ is, independently, H, $C_1$-$C_6$ alkyl or a protecting group;
- q is from 8 to about 14;
- j is 0 or from 1 to 5;
- r is 0 or from 1 to 5; and
- the sum of j and r is at least 1.

11. The oligomeric compound of claim 10 wherein each Z is methyl.

12. The oligomeric compound of claim 10 wherein each Z is $CH_2OCH_3$.

13. The oligomeric compound of claim 10 wherein each Z is $CH_2F$, $CHF_2$ or $CF_3$.

14. The oligomeric compound of claim 10 wherein j is 0.

15. The oligomeric compound of claim 10 wherein r is 0.

16. The oligomeric compound of claim 10 wherein j and r are each other than 0.

17. The oligomeric compound of claim 10 wherein j and r are each 2, q is 9 and G and H are each H.

18. The oligomeric compound of claim 10 wherein each L is a phosphodiester internucleoside linkage.

19. The oligomeric compound of claim 10 wherein each L is a phosphorothioate internucleoside linkage.

* * * * *

SEQUENCE LISTING

<160> NUMBER OF SEQ ID NOS: 11

<210> SEQ ID NO 1
<211> LENGTH: 3160
<212> TYPE: DNA
<213> ORGANISM: Homo sapiens

<400> SEQUENCE: 1

```
cctcccctcg cccggcgcgg tcccgtccgc ctctcgctcg cctcccgcct cccctcggtc      60
ttccgaggcg cccgggctcc cggcgcggcg gcggaggggg cgggcaggcc ggcgggcggt     120
gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300
gcccctctca gcgcctgtga gcagccgcgg gggcagcgcc ctcggggagc cggccggcct     360
gcggcggcgg cagcggcggc gtttctcgcc tcctcttcgt cttttctaac cgtgcagcct     420
cttcctcggc ttctcctgaa agggaaggtg gaagccgtgg gctcggcggg gagccggctg     480
aggcgcggcg gcggcggcgg cggcacctcc cgctcctgga gcggggggga gaagcggcgg     540
cggcggcggc cgcggcggct gcagctccag ggaggggggtc tgagtcgcct gtcaccattt     600
ccagggctgg gaacgccgga gagttggtct ctccccttct actgcctcca acacggcggc     660
ggcggcggcg gcacatccag ggacccgggc cggttttaaa cctcccgtcc gccgccgccg     720
cacccccccgt ggcccgggct ccggaggccg ccggcggagg cagccgttcg gaggattatt     780
cgtcttctcc ccattccgct gccgccgctg ccaggcctct ggctgctgag gagaagcagg     840
cccagtcgct gcaaccatcc agcagccgcc gcagcagcca ttacccggct gcggtccaga     900
gccaagcggc ggcagagcga ggggcatcag ctaccgccaa gtccagagcc atttccatcc     960
tgcagaagaa gccccgccac cagcagcttc tgccatctct ctcctccttt tcttcagcc     1020
acaggctccc agacatgaca gccatcatca aagagatcgt tagcagaaac aaaaggagat    1080
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataaccccac   1320
cacagctaga acttatcaaa ccctttttgtg aagatcttga ccaatggcta agtgaagatg    1380
acaatcatgt tgcagcaatt cactgtaaag ctggaaaggg acgaactggt gtaatgatat    1440
```

```
gtgcatattt attacatcgg ggcaaatttt taaaggcaca agaggccta gatttctatg    1500 gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa acaccatga    2280 aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatatccctt tttgtgtcaa aaggacattt aaaattcaat taggattaat aaagatggca    2520 cttttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc taccccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160

<210> SEQ ID NO 2
<211> LENGTH: 26
<212> TYPE: DNA
<213> ORGANISM: Homo sapiens

<400> SEQUENCE: 2
aatggctaag tgaagatgac aatcat                                         26

<210> SEQ ID NO 3
<211> LENGTH: 25
<212> TYPE: DNA
<213> ORGANISM: Homo sapiens

<400> SEQUENCE: 3
tgcacatatc attacaccag ttcgt                                          25

<210> SEQ ID NO 4
```

```
<211> LENGTH: 30
<212> TYPE: DNA
<213> ORGANISM: Homo sapiens

<400> SEQUENCE: 4
ttgcagcaat tcactgtaaa gctggaaagg                                    30

<210> SEQ ID NO 5
<211> LENGTH: 14
<212> TYPE: DNA
<213> ORGANISM: Artificial Sequence
<220> FEATURE:
<223> OTHER INFORMATION: A synthetic oligomer

<400> SEQUENCE: 5
cutagcactg gccu                                                     14

<210> SEQ ID NO 6
<211> LENGTH: 12
<212> TYPE: DNA
<213> ORGANISM: Artificial Sequence
<220> FEATURE:
<223> OTHER INFORMATION: A synthetic oligomer

<400> SEQUENCE: 6
tttttttttt tt                                                       12

<210> SEQ ID NO 7
<211> LENGTH: 12
<212> TYPE: DNA
<213> ORGANISM: Artificial Sequence
<220> FEATURE:
<223> OTHER INFORMATION: A synthetic oligomer

<400> SEQUENCE: 7
tttttttttt uu                                                       12

<210> SEQ ID NO 8
<211> LENGTH: 14
<212> TYPE: DNA
<213> ORGANISM: Artificial Sequence
<220> FEATURE:
<223> OTHER INFORMATION: A synthetic oligomer

<400> SEQUENCE: 8
cttagcactg gcct                                                     14

<210> SEQ ID NO 9
<211> LENGTH: 20
<212> TYPE: DNA
<213> ORGANISM: Artificial Sequence
<220> FEATURE:
<223> OTHER INFORMATION: A synthetic oligomer

<400> SEQUENCE: 9
ctgctagcct ctggatttga                                               20

<210> SEQ ID NO 10
<211> LENGTH: 18
<212> TYPE: DNA
<213> ORGANISM: Artificial Sequence
<220> FEATURE:
<223> OTHER INFORMATION: A synthetic oligomer

<400> SEQUENCE: 10
ctgctagcct ctggattt                                                 18
```

```
<210> SEQ ID NO 11
<211> LENGTH: 18
<212> TYPE: DNA
<213> ORGANISM: Artificial Sequence
<220> FEATURE:
<223> OTHER INFORMATION: A synthetic oligomer

<400> SEQUENCE: 11
cugctagcct ctggatuu                                               18
```